US009110086B2

(12) United States Patent  
Meikle et al.

(10) Patent No.: US 9,110,086 B2  
(45) Date of Patent: Aug. 18, 2015

(54) LIPID BIOMARKERS FOR STABLE AND UNSTABLE HEART DISEASE

(75) Inventors: Peter John Meikle, Lower Plenty (AU); Izhak Haviv, Caulfield (AU); Bronwyn Anne Kingwell, Melbourne (AU); Justin Bedo, Docklands (AU); Benjamin Goudey, Sassafras (AU)

(73) Assignee: BAKER IDI HEART AND DIABETES INSTITUTE HOLDINGS LIMITED, Melbourne (AU)

( * ) Notice: Subject to any disclaimer, the term of this patent is extended or adjusted under 35 U.S.C. 154(b) by 80 days.

(21) Appl. No.: 13/512,308

(22) PCT Filed: Nov. 26, 2010

(86) PCT No.: PCT/AU2010/001596  
§ 371 (c)(1),  
(2), (4) Date: Sep. 26, 2012

(87) PCT Pub. No.: WO2011/063470  
PCT Pub. Date: Jun. 3, 2011

(65) Prior Publication Data  
US 2013/0023054 A1 Jan. 24, 2013

Related U.S. Application Data

(60) Provisional application No. 61/264,767, filed on Nov. 27, 2009.

(51) Int. Cl.  
*G01N 33/92* (2006.01)  
*G01N 33/68* (2006.01)

(52) U.S. Cl.  
CPC ............ *G01N 33/92* (2013.01); *G01N 33/6893* (2013.01); *G01N 2800/323* (2013.01); *G01N 2800/50* (2013.01); *G01N 2800/52* (2013.01); *G01N 2800/56* (2013.01)

(58) Field of Classification Search  
CPC ................. G01N 2800/323; G01N 2800/324; G01N 2800/50; G01N 2800/52; G01N 2800/56; G01N 33/6893; G01N 33/92  
USPC .......................... 436/63, 71, 161, 173; 435/29  
See application file for complete search history.

(56) References Cited

U.S. PATENT DOCUMENTS

| | | | |
|---|---|---|---|
| 6,816,743 B2 * | 11/2004 | Moreno et al. | 600/473 |
| 7,361,473 B2 * | 4/2008 | Valkirs et al. | 435/7.1 |
| 7,459,286 B1 * | 12/2008 | Hazen et al. | 435/28 |
| 2005/0181386 A1 | 8/2005 | Diamond et al. | |
| 2006/0099608 A1 * | 5/2006 | Epstein et al. | 435/6 |
| 2007/0042438 A1 * | 2/2007 | Zeiher et al. | 435/7.5 |
| 2007/0207507 A1 * | 9/2007 | Kim et al. | 435/7.23 |
| 2010/0105088 A1 * | 4/2010 | Handberg et al. | 435/7.92 |

FOREIGN PATENT DOCUMENTS

| | | | |
|---|---|---|---|
| WO | 03/040691 A2 | 5/2003 | |
| WO | 2008/118413 | * 10/2008 | |
| WO | 2008/118413 A2 | 10/2008 | |

OTHER PUBLICATIONS

Chen et al. American Journal of Cardiology, vol. 100, 2007, pp. 1341-1346.*  
Gronholdt, et al., American Heart Association, Inc., 97: 34-40, 1998.  
Lavi, et al., Local Production of Lipoprotein-Associated Phospholipase A2 and Lysophosphatidylcholine in the Coronary Circulation. Circulation 115, 2715-2721, 2007.  
Mas, et al., Local Non-Esterified Fatty Acids Correlate With Inflammation in Atheroma Plaques of Patients With Type 2 Diabetes. Diabetes 59, 1292-1301, 2010.  
Meikle, et al., Plasma lipidomic analysis of stable and unstable coronary artery disease. Arterioscler Thromb Vasc Biol 31, 2723-2732, 2011.  
Messner, et al., Identification of Lysophosphatidylcholine—Chlorohydrin in Human Atherosclerotic Lesions. Lipids 43, 243-249, 2008.  
Pettinella, et al., Targeted quantitative analysis of fatty acids in atherosclerotic plaques by high sensitivity liquid chromatography/tandem mass spectrometry. Journal of Chromatography B 850, 168-176, 2007.  
Quehenberger, et al., Lipidomics reveals a remarkable diversity of lipids in human plasma. Journal of Lipid Research 51, 3299-3305, 2010.  
Roussel, et al., NMR-based prediction of cardiovascular risk in diabetes. Nat Med 13, 399-400, 2007.  
Stegemann, et al., Comparative Lipidomics Profiling of Human Atherosclerotic Plaques / Clinical Perspective. Circulation: Cardiovascular Genetics 4, 232-242, 2011.  
Thomas, et al., Mass spectrometry for the evaluation of cardiovascular disease based on proteomics and lipidomics. Thrombosis and Haemostatis 106.1, 20-33, 2011.  
Thukkani, et al., Identification of α-Chloro Fatty Aldehydes and Unsaturated Lysophosphatidylcholine Molecular Species in Human Atherosclerotic Lesions. Circulation 108, 3128-3133, 2003.  
Wurtz, et al., High-throughput quantification of circulating metabolites improves prediction of subclinical atherosclerosis. Eur Heart J In press, 2012.  
Wurtz, et al., Characterization of systemic metabolic phenotypes associated with subclinical atherosclerosis. Mol Biosyst 7, 385-393, 2011.  
Davies, Michael J., "Stability and Instability: Two Faces of Coronary Atherosclerosis", 1996, Circulation, 94:2013-2020.  
White et al., "Matrix metalloproteinase-3 and coronary remodelling: Implications for unstable coronary disease", Cardiovascular Research, 2007, 75: 813-820.

(Continued)

*Primary Examiner* — Maureen Wallenhorst  
(74) *Attorney, Agent, or Firm* — MH2 Technology Law Group, LLP

(57) ABSTRACT

The present invention relates generally to the field of diagnostic and prognostic assays for heart disease. More particular, the present invention provides an assay for diagnosing the presence or extent of development of heart disease or its classification or state thereof. The assay of the present invention is also useful in the stratification of a subject with respect to a risk of developing heart disease. The assay of the present invention is also capable of integration into pathology architecture to provide a diagnostic and reporting system.

7 Claims, 7 Drawing Sheets

(56) References Cited

OTHER PUBLICATIONS

Little et al., "Can coronary angiography predict the site of a subsequent myocardial infarction in patients with mild-to-moderate coronary artery disease?", Circulation, 1988, 78:1157-1166.
Burke et al., "Morphological Predictors of Arterial Remodeling in Coronary Atherosclerosis", Circulation, 2002, 105:297-303.
Finn et al., "Concept of Vulnerable/Unstable Plaque," Arterioscler. Thromb. Vasc. Biol,, 2010, 30:1282-1292.
Maurovich-Horvat et al., "Comprehensive plaque assessment by coronary CT angiography," Nat. Rev. Cardiol., 2014, 11:390-402.
Glagov et al., "Compensatory Enlargement of Human Atherosclerotic Coronary Arteries," N. Engl. J. Med., 1987, 316(22): 1371-1375.
Meikle, et al., "Plasma lipidomic analysis of stable and unstable coronary artery disease", Atherosclerosis Supplements, 2010, vol. 11, No. 2, p. 24.
Thomas, et al., "High-throughput phospholipidic fingerprinting by online desorption of dried spots and quadrupole-linear ion trap mass spectrometry: Evaluation of atherosclerosis biomarkers in mouse plasma", Analytical Chemistry, 2010, vol. 82, pp. 6687-6694.
Gaziano, et al., "Fasting triglycerides, high-density lipoprotein, and risk of myocardial infarction", Circulation, 1997, vol. 96, pp. 2520-2525.
Milionis, et al., "Lipid abnormalities and cardiovascular risk in the elderly", Current Medical Research and Opinion, 2008, vol. 24, No. 3, pp. 653-657.
Ekroos, et al., "Lipidomics: A tool for studies of Atherosclerosis", Current Atherosclerosis Report, 2010, vol. 12, pp. 273-281.
International Search Report issued on Feb. 14, 2011 for International Application No. PCT/AU2010/001596.

* cited by examiner

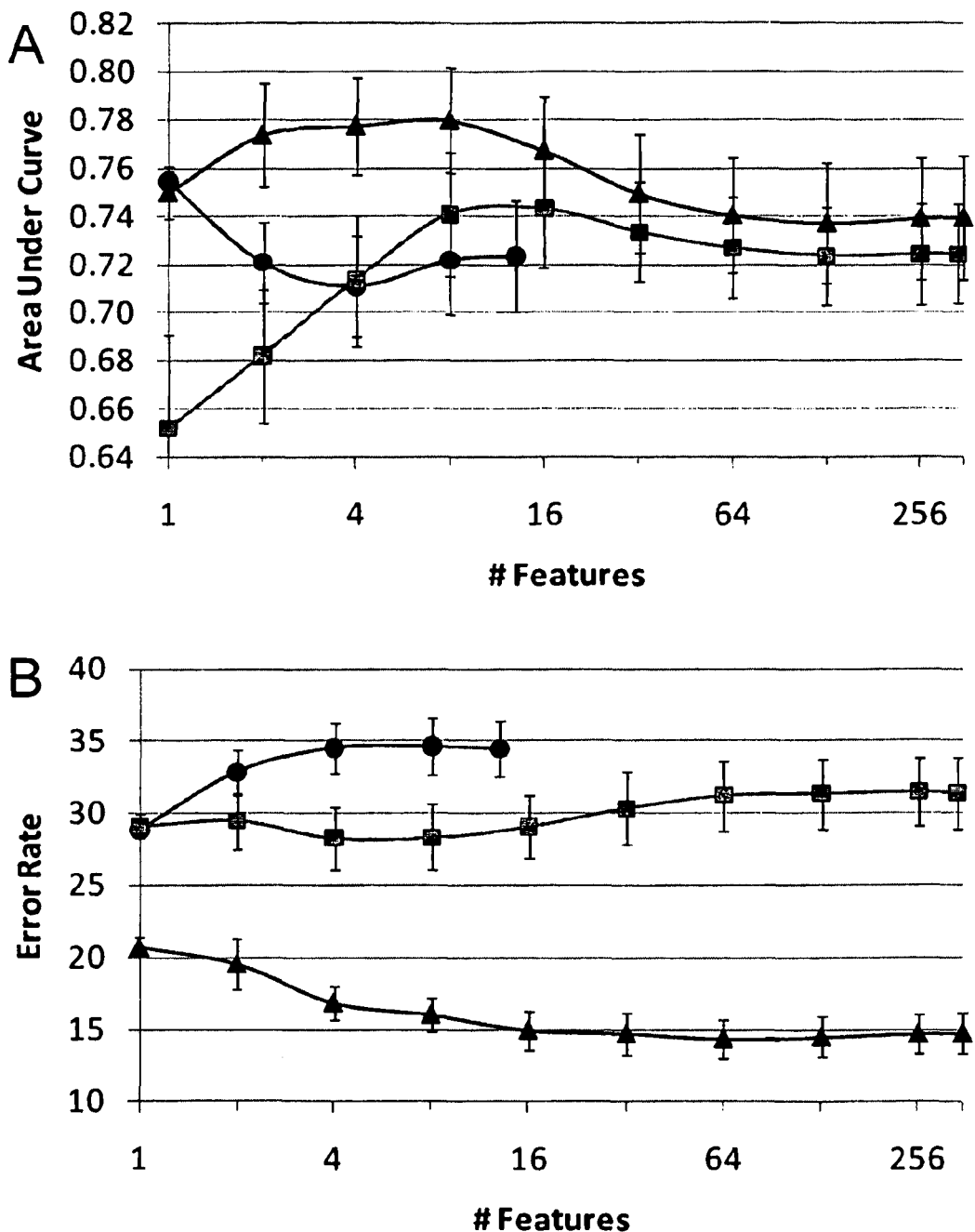
Figures 1(A) and (B)

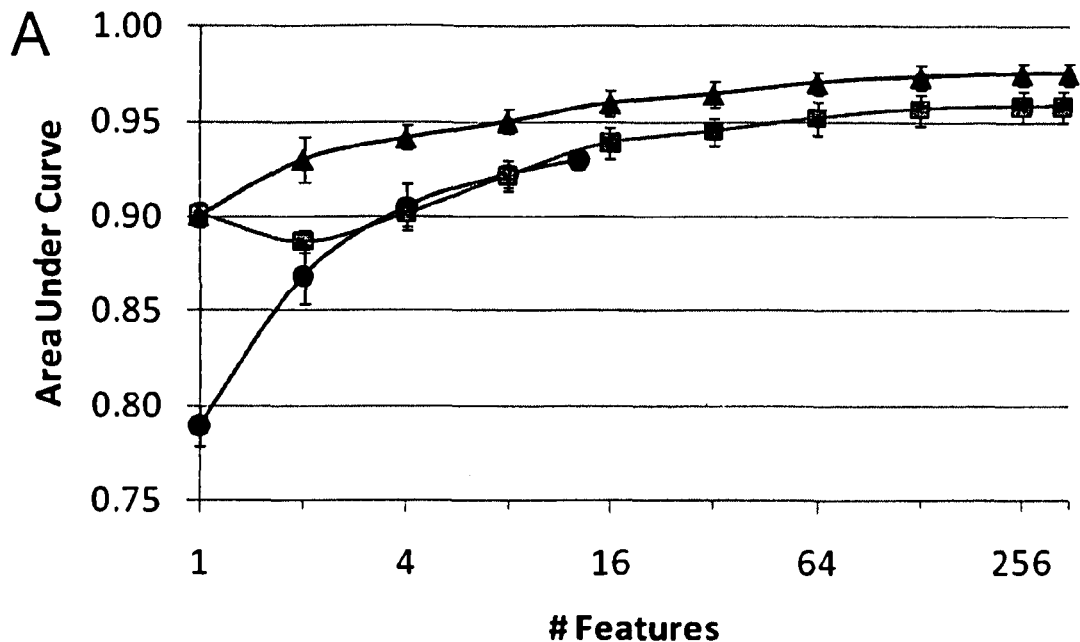
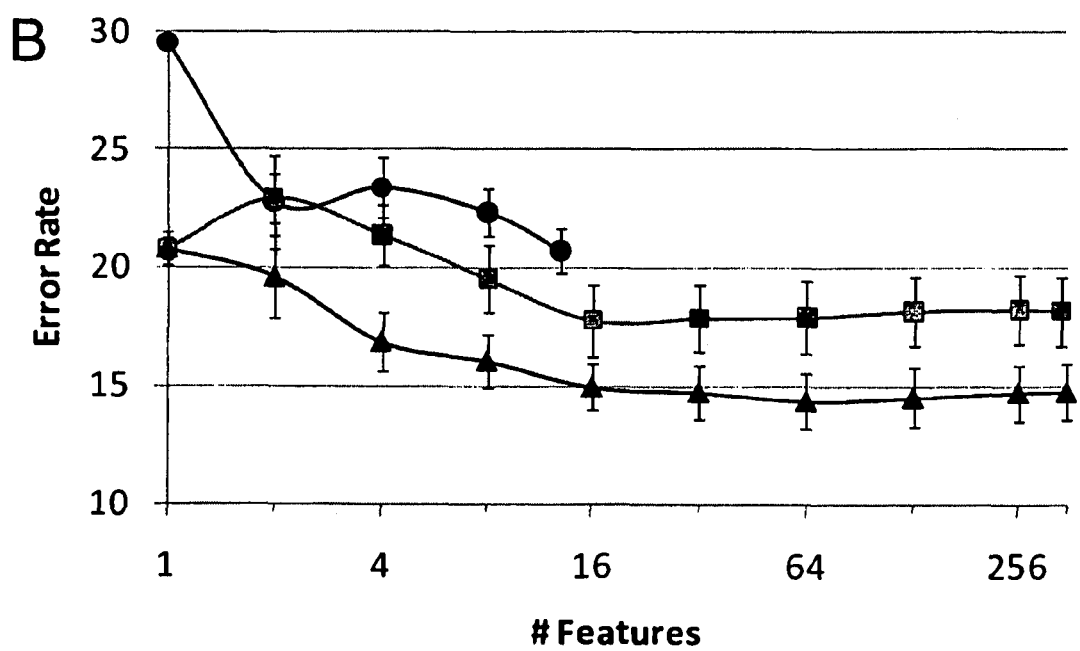
Figures 2(A) and (B)

A
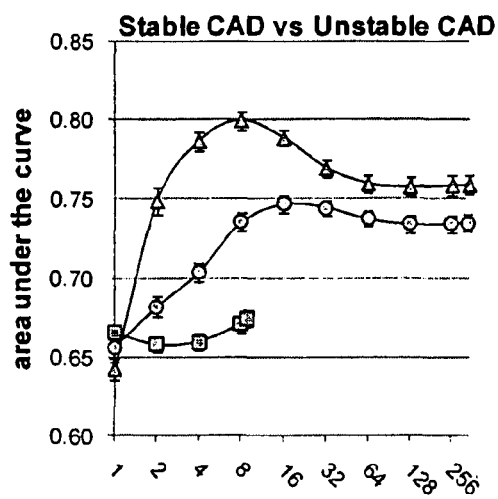
B
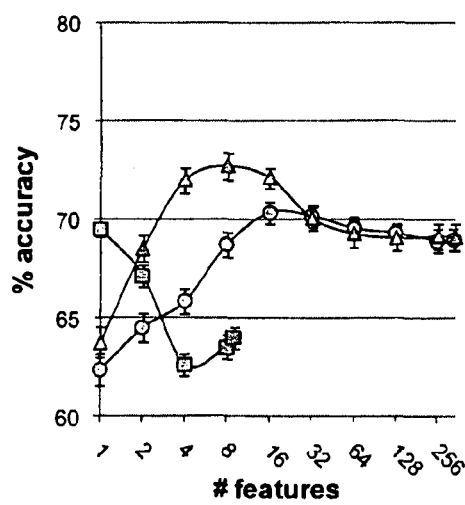
C
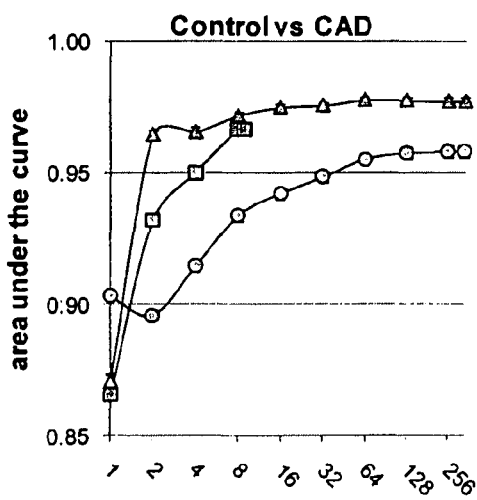
D
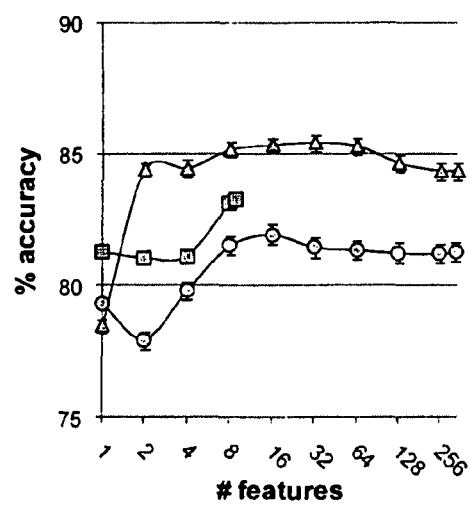
Figure 5

LIPID BIOMARKERS FOR STABLE AND UNSTABLE HEART DISEASE

RELATED APPLICATIONS

This application is a U.S. National Phase of International Application No. PCT/AU2010/001596, filed Nov. 26, 2010, designating the U.S., and published as WO 2011/063470 on Jun. 3, 2011 which claims the benefit of U.S. Provisional Application No. 61/264,767 filed Nov. 27, 2009.

FIELD

The present invention relates generally to the field of diagnostic and prognostic assays for heart disease. More particularly, the present invention provides an assay for diagnosing the presence or extent of development of heart disease or its classification or state thereof. The assay of the present invention is also useful in the stratification of a subject with respect to a risk of developing heart disease. The assay of the present invention is also capable of integration into pathology architecture to provide a diagnostic and reporting system.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Atherosclerosis (AS) is the single most common cause of heart disease and is the major contributor to the development of angina, heart attacks and stroke. Despite the introduction of statin-based therapy to reduce levels of plasma low density lipoprotein (LDL) cholesterol, the epidemic of heart disease is claiming tens of thousands of lives each year, particularly in Western countries and costs the health system over billions of dollars per year (National Health Survey: Summary of Results, Australia, 2004-05, cat. no. 4364.0, ABS, Can berra, Vol: Australian Bureau of Statistics, 2006, (AIHW) AIoHaW. Health system expenditure on disease and injury in Australia, 2000-01. Health and Welfare Expenditure Series No. 19, 2004; HWE 26).

Atherosclerosis begins to develop early in life and progresses with time. However, the rate of progression is, to a large extent, unpredictable and differs markedly amongst seemingly comparable individuals. One of the early events leading to Atherosclerosis is the formation of "fatty streaks", deposits of monocytes, macrophages, foam cells and lipids within the intima of the arterial wall. Fatty streaks exist in most adults and can remain as fatty streaks for years or decades, having little or no adverse clinical effects. Some, but not all, fatty steaks progress into fibriolipid plaques which are distinguished by the presence of smooth muscle cells and increased extracellular fibres within the intima. Cell death within the plaque leads to the formation of a necrotic core, the accumulation of extracellular material and the formation of the complex plaque. At this stage, the plaque may severely restrict blood flow leading to a range of clinical complications; however, many individuals will be unaware of the problem and show no symptoms.

Complex plaques can become unstable (a "vulnerable" plaque) as a result of the thinning of the smooth muscle cell layer over the plaque. Unstable plaques may rupture leading to thrombosis, myocardial infarction and stroke with the associated morbidity and mortality (the "vulnerable" patient).

Although plaque accumulation and development is progressive throughout life, the switch from stable to unstable plaque can occur earlier or later in the disease process. Thus a 45 year old with relatively low levels of plaque can become unstable leading to a coronary event.

Despite our detailed knowledge of plaque pathology and progression many individuals have no clinical symptoms and so are unaware of their risk. In 30 to 50% of these individuals, the first indicator of Atherosclerosis is an acute heart attack which is often fatal (Heart Disease and Stroke Statistics-2006 Update, Dallas Tex.: American Heart Association, 2006. Available at http://www.americanheart.org/downloadable/heart/1198257493273HS_Stats%202008.pdf)

A non-invasive assay is required to identify and monitor heart disease.

SUMMARY

Each embodiments described herein is to be applied mutatis mutandis to each any every embodiment unless specifically stated otherwise.

The present invention applies a lipidomic approach to identifying the presence, development, stage or severity of heart disease or its various manifestations.

An association is therefore identified between the level of lipidomic analytes in a subject and heart disease. The term "analyte" includes biomarker and indicator. By "heart disease" is meant an individual condition as well as a collection of conditions within the clinical spectrum of symptomatic or asymptomatic heart disease. The lipidomic biomarkers provide a range of risk indicators of the severity of disease and rate of progression and a classification of the disease such as stable or unstable in relation to plaques. This risk ranges from minor to extreme. Knowledge of the level of risk enables intervention to mitigate further development of heart disease. The ability to monitor and identify markers of heart disease including diagnosing it in asymptomatic subjects further enables decisions on the type of medical intervention required from behavioural modification and medicaments to surgical intervention. The lipidomic biomarkers are also instructive as to the level of risk for an individual developing more severe symptomology associated with heart disease. The lipidomic profile also defines a desired state of health in subjects. Hence, monitoring changing levels of lipid analytes is a useful tool in pharmacotranslational studies and clinical management of patients.

Reference to "heart disease" includes conditions such as coronary heart disease (including coronary artery disease, angina pectoris and myocardial infarction), atherosclerosis, cardiomyopathy (including that associated with arrhythmia), cardiovascular disease, ischaemic heart disease, heart failure (including cor pulmonale), hypertensive heart disease (including left ventricular hypertrophy and congestive heart failure), inflammatory heart disease (including endocarditis, inflammatory cardiomegaly and myocarditis) and valvular heart disease (including aortic valve stenosis and mitral valve prolapse). Heart disease spectrum also includes associated conditions such as aortic aneurysm, hypertension, thrombosis and pericarditis. Heart disease is a spectrum of clinical manifestations.

The present invention is predicated in part on the determination that subjects with heart disease or at risk of developing heart disease exhibit altered lipid metabolism. The levels of particular lipidomic analytes correlate with the state, stage and/or classification of heart disease and its progression in symptomatic and asymptomatic subjects. By "classification" includes identifying subjects with stable and unstable plaques and hence, individuals can be classified as vulnerable or non-vulnerable subjects. Hence, the present invention enables stratification of subjects into risk categories, treatment categories and likely progression outcomes.

Twenty-three different lipid classes and three hundred and twenty-nine lipid analytes were analysed. Ten different lipid classes comprising thirty lipid analytes were particularly useful for distinguishing between vulnerable and non-vulnerable subjects. Further, eighteen lipid classes comprising ninety-five lipid analytes were useful for distinguishing between control normal subjects and subjects with coronary artery disease. Furthermore, as summarised in Table 16, phosphatidylinositol lipids including seventeen lipid analytes in this class were on average significantly reduced in vulnerable subjects; thirteen lipid classes were reduced on average in coronary artery disease subjects and one lipid class, the diacylglycerols, was increased in coronary artery disease subjects.

The lipidomic approach uses one or more of three groups of lipid analytes:
(i) modified ceramides (modCER), modified phosphatidylcholines (modPC) and, modified cholesterol esters (modCE) selected from those listed in Table 1;
(ii) two or more non-modified lipid analytes selected from the list in Table 1; and/or
(iii) two or more lipid analytes wherein at least one is a modified lipid analyte (modCER, modPC and/or modCE) and at least one is a non-modified lipid analyte selected from the list in Table 1.

The levels or ratios of levels the lipidomic analytes are determined relative to a control. The assay may also be automated or semi-automated. In particular, the levels or ratios of, levels may be used as input data for multivariate or univariate analysis leading to an algorithm which can be used to generate an index of probability of having or progressing with heart disease.

The levels of the lipid biomarkers may also be used in combination with other standard indicators of heart disease, whether biochemical markers, symptoms or electrocardial techniques.

Accordingly, one aspect of the present invention is directed to an assay to stratify a subject as a vulnerable or non-vulnerable subject with respect to plaques, the assay comprising determining the levels of a lipid analyte selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
wherein the level or ratio of the lipid analyte or analytes relative to a control identifies the subject as being vulnerable or non-vulnerable.

Yet another aspect of the present invention contemplates an assay to stratify a subject with respect to heart disease, the assay comprising determining the levels of a lipid analyte selected from the list consisting of:
(i) one or more modified lipid analytes listed in Table 1;
(ii) two or more non-modified lipid analytes listed in Table 1, and/or
(iii) two or more lipid analytes wherein at least one is a modified lipid analyte listed in Table 1 and at least one is a non-modified lipid analyte listed in Table 1;
wherein the level or ratio of the lipid analyte or analytes relative to a control provides a correlation as to the presence, state, classification or progression of heart disease.

In some embodiments, the assays comprise determining the levels of at least two lipid analytes.

Still another aspect of the present invention contemplates the use of a panel of lipid analytes selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
in the manufacture of an assay to identify the presence, state, classification or progression of heart disease in a subject. In particular embodiments, the assay is used to identify vulnerable or non-vulnerable subjects.

Even yet another aspect of the present invention relates to a method of treatment or prophylaxis of a subject comprising assaying the subject with respect to heart disease by determining the levels of a lipid analyte selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
wherein the level or ratio of the lipid analyte or analytes relative to a control provides a correlation to the presence, state, classification or progression of heart disease and then providing therapeutic and/or behavioural modification to the subject.

The "stratification" is in effect a level of risk that a subject has heart disease or is developing heart disease or is likely to develop symptoms of heart disease.

The determination of the levels or ratios of the lipid biomarkers may be used in combination with other indicators of heart disease and may be used to monitor efficacy of treatment. In addition, the assay may be useful in determining the most effective therapeutic or behavioural intervention to treat heart disease in symptomatic or asymptomatic subjects.

The assay may also be used in a personalized medicine approach in the management of heart disease and/or as part of a pathology architecture platform.

The above summary is not and should not be seen in any way as an exhaustive recitation of all embodiments of the present invention.

TABLE 1

| \multicolumn{2}{c}{Lipid Analytes (Biomarkers)} | |
| --- | --- |
| No. (#) | Analyte |
| 1 | Cer 16:0 |
| S1 | Cer 17:0 (IS) |
| 2 | Cer 18:1 |
| 3 | Cer 18:0 |
| 4 | Cer 20:0 |
| 5 | Cer 22:0 |
| 6 | Cer 24:1 |
| 7 | Cer 24:0 |
| 8 | MHC 16:0 |
| S2 | MHC 16:0d3 (IS) |
| 9 | MHC 18:1 |
| 10 | MHC 18:0 |
| 11 | MHC 20:0 |
| 12 | MHC 22:0 |
| 13 | MHC 24:1 |
| 14 | MHC 24:0 |
| 15 | DHC 16:0 |

TABLE 1-continued

Lipid Analytes (Biomarkers)

| No. (#) | Analyte |
|---|---|
| S3 | DHC 16:0d3 (IS) |
| 16 | DHC 18:1 |
| 17 | DHC 18:0 |
| 18 | DHC 20:0 |
| 19 | DHC 22:0 |
| 20 | DHC 24:1 |
| 21 | DHC 24:0 |
| 22 | THC 16:0 |
| S4 | THC 17:0 (IS) |
| 23 | THC 18:1 |
| 24 | THC 18:0 |
| 25 | THC 20:0 |
| 26 | THC 22:0 |
| 27 | THC 24:1 |
| 28 | THC 24:0 |
| 29 | GM3 16:0 |
| 30 | GM3 18:0 |
| 31 | GM3 20:0 |
| 32 | GM3 22:0 |
| 33 | GM3 24:1 |
| 34 | GM3 24:0 |
| 35 | modCer 576.5/7.68 |
| 36 | modCer 614.6/5.72 |
| 37 | modCer 632.6/9.22 |
| 38 | modCer 651.6/7.56 |
| 39 | modCer 703.6/5.87 |
| 40 | modCer 731.6/6.22 |
| 41 | modCer 766.6/7.17 |
| 42 | modCer 769.6/8.01 |
| 43 | modCer 798.7/7.29 |
| S5 | Acyl Cer 17:0 18:1 (IS) |
| 44 | modCer 875.7/9.23 |
| 45 | modCer 883.8/7.75 |
| 46 | modCer 886.8/9.06 |
| 47 | modCer 910.8/8.98 |
| 48 | modCer 921.8/9.05 |
| S6 | SM 12:0 (IS) |
| S6 | SM 12:0 (IS) |
| S6 | SM 12:0 (IS) |
| 49 | SM 14:0 |
| 50 | SM 15:0 |
| 51 | SM 16:1 |
| 52 | SM 16:0 |
| 53 | SM 18:1 |
| 54 | SM 18:0 |
| 55 | SM 20:1 |
| 56 | SM 22:1 |
| 57 | SM 22:0 |
| 58 | SM 24:2 |
| 59 | SM 24:1 |
| 60 | SM 24:0 |
| 61 | PG 16:1 18:1 |
| 62 | PG 16:0 18:1 |
| S7 | PG 17:0 17:0 (IS) |
| 63 | PG 18:1 18:1 |
| 64 | PG 18:0 18:1 |
| S8 | BMP 14:0 14:0 (IS) |
| 65 | BMP 18:1 18:1 |
| S9 | PS 17:0/17:0 |
| 66 | PS 36:2 |
| 67 | PS 36:1 |
| 68 | PS 38:5 |
| 69 | PS 38:4 |
| 70 | PS 38:3 |
| 71 | PS 40:6 |
| 72 | PS 40:5 |
| 73 | PE 32:1 |
| 74 | PE 32:0 |
| 75 | PE 34:2 |
| 76 | PE 34:1 |
| S10 | PE 17:0/17:0 (IS) |
| 77 | PE 36:5 |
| 78 | PE 36:4 |
| 79 | PE 36:3 |
| 80 | PE 36:2 |
| 81 | PE 36:1 |
| 82 | PE 36:0 |
| 83 | PE 38:6 |
| 84 | PE 38:5 |
| 85 | PE38:4 |
| 86 | PE 38:3 |
| 87 | PE 38:2 |
| 88 | PE 38:1 |
| 89 | PE 40:7 |
| 90 | PE 40:6 |
| 91 | PI 32:1 |
| 92 | PI 32:0 |
| 93 | PI 34:1 |
| 94 | PI 34:0 |
| 95 | PI 36:4 |
| 96 | PI 36:3 |
| 97 | PI 36:2 |
| 98 | PI 36:1 |
| 99 | PI 36:0 |
| 100 | PI 38:6 |
| 101 | PI 38:5 |
| 102 | PI 38:4 |
| 103 | PI 38:3 |
| 104 | PI 38:2 |
| 105 | PI 40:6 |
| 106 | PI 40:5 |
| 107 | PI 40:4 |
| S11 | LPC 13:0 (IS) |
| 108 | LPC 14:0 |
| 109 | LPC 15:0 |
| 110 | LPC 16:1 |
| 111 | LPC 16:0 |
| 112 | LPC 18:2 |
| 113 | LPC 18:1 |
| 114 | LPC 18:0 |
| 115 | LPC 20:5 |
| 116 | LPC 20:4 |
| 117 | LPC 20:3 |
| 118 | LPC 20:2 |
| 119 | LPC 20:1 |
| 120 | LPC 20:0 |
| 121 | LPC 22:6 |
| 122 | LPAF 16:0 |
| 123 | LPAF 18:1 |
| 124 | LPAF 18:0 |
| S12 | PC 13:0/13:0 |
| S12 | PC 13:0/13:0 |
| 125 | PC 30:2 |
| 126 | PC 32:2 |
| 127 | PC 32:1 |
| 128 | PC 32:0 |
| 129 | PC 34:3 |
| 130 | PC 34:2 |
| 131 | PC 34:1 |
| 132 | PC 34:0 |
| 133 | PC 36:5 |
| 134 | PC 36:4 |
| 135 | PC 36:3 |
| 136 | PC 36:2 |
| 137 | PC 38:6 |
| 138 | PC 38:5 |
| 139 | PC 38:4 |
| 140 | PC 40:7 |
| 141 | PC 40:6 |
| 142 | PC 40:5 |
| S13 | PC 21:0 21:0 (IS) |
| S13 | PC 21:0 21:0 (IS) |
| S13 | PC 21:0 21:0 (IS) |
| 143 | PC 44:12 |
| 144 | oddPC 31:1 |
| 145 | oddPC 31:0 |
| 146 | oddPC 33:0 |
| 147 | oddPC 33:1 |
| 148 | oddPC 33:2 |
| 149 | oddPC 35:4 |
| 150 | oddPC 35:3 |
| 151 | oddPC 35:2 |

TABLE 1-continued

Lipid Analytes (Biomarkers)

| No. (#) | Analyte |
|---|---|
| 152 | oddPC 35:1 |
| 153 | oddPC 35:0 |
| 154 | oddPC 37:6 |
| 155 | oddPC 37:5 |
| 156 | oddPC 37:4 |
| 157 | oddPC 37:3 |
| 158 | oddPC 37:2 |
| 159 | APC 32:1 |
| 160 | APC 32:0 |
| 161 | APC 34:2 |
| 162 | APC 34:1 |
| 163 | APC 34:0 |
| 164 | APC 36:5 |
| 165 | APC 36:4 |
| 166 | APC 36:3 |
| 167 | APC 36:2 |
| 168 | APC 36:1 |
| 169 | APC 36:0 |
| 170 | APC 38:6 |
| 171 | APC 38:5 |
| 172 | APC 38:4 |
| 173 | APC 38:3 |
| 174 | APC 38:2 |
| 175 | modPC 506.3/3.50 |
| 176 | modPC 508.3/3.30 (LPAF 18:1) |
| 177 | modPC 510.3/4.00 (LPAF 18:0) |
| 178 | modPC 512.3/1.70 |
| 179 | modPC 536.3/3.50 |
| 180 | modPC 538.3/4.10 |
| 181 | modPC 552.4/3.90 (LPC 20:0) |
| 182 | modPC 564.4/4.70 (LPAF 22:1) |
| 183 | modPC 566.4/5.10 (LPAF 22:0) |
| 184 | modPC 580.4/4.84 (LPC 22:0) |
| 187 | modPC 594.4/3.26 |
| 189 | modPC 608.4/3.84 |
| 190 | modPC 610.4/2.03 |
| 191 | modPC 622.4/4.54.(PC 24:0) |
| 192 | modPC 633.4/4.51 |
| 193 | modPC 636.4/3.37 |
| 194 | modPC 645.4/4.49 |
| 195 | modPC 650.4/3.24 |
| 196 | modPC 650.4/4.44 |
| 197 | modPC 650.4/3.94 |
| 198 | modPC 664.4/4.22 |
| 199 | modPC 666.4/2.99 |
| 200 | modPC 678.4/4.37 |
| 201 | modPC 678.4/4.94 |
| 202 | modPC 678.4/5.51 (PC 28:0) |
| 203 | modPC 690.4/4.11 |
| 204 | modPC 690.4/4.90 |
| 205 | modPC 690.4/6.00 |
| 206 | modPC 692.4/5.05 |
| 207 | modPC 692.4/5.52 (APC 30:0) |
| 208 | modPC 692.4/6.10 |
| 209 | modPC 694.4/6.20 |
| 210 | modPC 703.5/4.09 |
| 211 | modPC 704.5/3.81 |
| 212 | modPC 706.5/3.79 |
| 213 | modPC 720.5/4.52 |
| 214 | modPC 736.5/5.38 |
| 215 | modPC 743.5/5.91 |
| 217 | modPC 752.5/5.58 (PC34:5) |
| 220 | modPC 772.5/5.37 |
| 221 | modPC 773.6/6.47 |
| 222 | modPC 788.6/5.19 |
| 223 | modPC 801.6/6.70 |
| 224 | modPC 816.6/5.58 |
| 225 | modPC 818.6/6.10 |
| 226 | modPC 818.6/6.48 (APC 40:7) |
| 227 | modPC 828.6/6.03 |
| 228 | modPC 843.6/7.10 |
| 229 | modPC 866.6/7.24 |
| 230 | modPC 878.6/5.98 (modPC877.6/7.1) |
| 231 | modPC 881.6/6.05 (modPC879.6/6.1) |
| 232 | COH |
| S14 | COH d7 (IS) |
| 233 | CE 14:0 |
| 234 | CE 15:0 |
| 235 | CE 16:2 |
| 236 | CE 16:1 |
| 237 | CE 16:0 |
| 238 | CE 17:1 |
| 239 | CE 17:0 |
| 240 | CE 18:3 |
| 241 | CE 18:2 |
| 242 | CE 18:1 |
| 243 | CE 18:0 |
| S15 | CE 18:0 d6 (IS) |
| S15 | CE 18:0 d6 (IS) |
| S15 | CE 18:0 d6 (IS) |
| 244 | CE 20:5 |
| 245 | CE 20:4 |
| 246 | CE 20:3 |
| 247 | CE 20:2 |
| 248 | CE 20:1 |
| 249 | CE 22:6 |
| 250 | CE 22:5 |
| 251 | CE 22:4 |
| 252 | CE 22:3 |
| 253 | CE 22:2 |
| 254 | CE 22:1 |
| 255 | CE 22:0 |
| 256 | CE 24:6 |
| 257 | CE 24:5 |
| 258 | CE 24:4 |
| 259 | CE 24:3 |
| 260 | CE 24:2 |
| 261 | CE 24:1 |
| 262 | CE 24:0 |
| 263 | modCE 558.5/7.74 |
| 264 | modCE 588.5/7.94 |
| 265 | modCE 682.7/8.76 |
| 266 | modCE 790.8/6.57 |
| 267 | DG 14:0 14:0 |
| 268 | DG 14:1 16:0 |
| 269 | DG 14:0 16:0 |
| S16 | DG 15:0 15:0 (IS) |
| 270 | DG 14:0 18:2 |
| 271 | DG 14:0 18:1 |
| 272 | DG 16:0 16:0 |
| 273 | DG 16:0 18:2 |
| 274 | DG 16:1 18:1 |
| 275 | DG 16:0 18:1 |
| 276 | DG 18:0 16:1 |
| 277 | DG 16:0 18:0 |
| 278 | DG 16:0 20:4 |
| 279 | DG 18:1 18:3 |
| 280 | DG 18:2 18:2 |
| 281 | DG 16:0 20:3 |
| 282 | DG 18:1 18:2 |
| 283 | DG 18:0 18:2 |
| 284 | DG 18:1 18:1 |
| 285 | DG 18:0 18:1 |
| 286 | DG 16:0 20:0 |
| 287 | DG 18:0 18:0 |
| 288 | DG 16:0 22:6 |
| 289 | DG 16:0 22:5 |
| 290 | DG 18:1 20:4 |
| 291 | DG 18:0 20:4 |
| 292 | DG 18:1 20:3 |
| 293 | DG 18:1 20:0 |
| 294 | TG 14:0 16:1 18:2 |
| 295 | TG 16:1 16:1 16:1 |
| 296 | TG 14:0 16:0 18:2 |
| 297 | TG 14:0 16:1 18:1 |
| 298 | TG 14:1 16:0 18:1 |
| 299 | TG 14:1 16:1 18:0 |
| 300 | TG 18:1 14:0 16:0 |
| 301 | TG 16:0 16:0 16:0 |
| 302 | TG 15:0 18:1 16:0 |
| 303 | TG 17:0 16:0 16:1 |
| 304 | TG 17:0 18:1 14:0 |

TABLE 1-continued

Lipid Analytes (Biomarkers)

| No. (#) | Analyte |
|---|---|
| 305 | TG 14:0 18:2 18:2 |
| 306 | TG 14:1 18:0 18:2 |
| 307 | TG 14:1 18:1 18:1 |
| 308 | TG 16:1 16:1 18:1 |
| 309 | TG 16:0 16:0 18:2 |
| 310 | TG 16:1 16:1 18:0 |
| 311 | TG 16:0 16:1 18:1 |
| 312 | TG 14:0 18:0 18:1 |
| 313 | TG 16:0 16:0 18:1 |
| 314 | TG 16:0 16:0 18:0 |
| 315 | TG 15:0 18:1 18:1 |
| 316 | TG 17:0 18:1 16:1 |
| 317 | TG 17:0 18:2 16:0 |
| 318 | TG 17:0 18:1 16:0 |
| 319 | TG 17:0 16:0 18:0 |
| S17 | TG 17:0 17:0 17:0 (IS) |
| S17 | TG 17:0 17:0 17:0 (IS) |
| 320 | TG 16:0 18:2 18:2 |
| 321 | TG 16:1 18:1 18:2 |
| 322 | TG 16:1 18:1 18:1 |
| 323 | TG 16:0 18:1 18:2 |
| 324 | TG 16:0 18:1 18:1 |
| 325 | TG 16:0 18:0 18:1 |
| 326 | TG 17:0 18:1 18:1 |
| 327 | TG 18:2 18:2 18:2 |
| 328 | TG 18:1 18:2 18:2 |
| 329 | TG 18:0 18:2 18:2 |
| 330 | TG 18:1 18:1 18:2 |
| 331 | TG 18:1 18:1 18:1 |
| 332 | TG 18:0 18:1 18:1 |
| 333 | TG 18:0 18:0 18:1 |
| 334 | TG 18:0 18:0 18:0 |
| 335 | TG 18:2 18:2 20:4 |
| 336 | TG 18:1 18:1 20:4 |
| 337 | TG 18:1 18:1 22:6 |

List of Abbreviations

| | |
|---|---|
| acCer | acylceramide |
| APC | alkylphosphatidylcholine |
| BMP | bis(monoacylglycero)phosphate |
| CE | cholesterol ester |
| Cer | ceramide |
| COH | cholesterol |
| DG | diacylglycerol |
| DHC | dihexosylceramide |
| GM3 | $G_{M3}$ ganglioside |
| LPAF | lysoplatelet activating factor |
| LPC | lysophosphatidylcholine |
| MHC | monohexosylceramide |
| modCE | modified cholesterol ester |
| modCer | modified ceramide |
| modPC | modified phosphatidylcholine |
| oddPC | odd chain phosphatidylcholine |
| PC | phosphatidylcholine |
| PE | phosphatidylethanolamine |
| PG | phosphatidylglycerol |
| PI | phosphatidylinositol |
| PS | phosphatidylserine |
| SM | sphingomyelin |
| TG | triaclyglycerol |
| THC | trihexosylcermide |

BRIEF DESCRIPTION OF THE FIGURES

Some figures contain color representations or entities. Color photographs are available from the Patentee upon request or from an appropriate Patent Office. A fee may be imposed if obtained from a Patent Office.

FIGS. 1(A) and (B) are graphical representations of the area under the curve and error rate resulting from stable CAD vs unstable CAD models. Recursive feature elimination (RFE) with three-fold cross validation (repeated 100 times) was used to develop multivariate models using support vector machine learning. This was done for models of varying feature size (e.g., 1, 2, 4, 8, 16, 32 and 64) and for models that included either traditional risk factors alone (blue circles) lipids alone (green squares) or lipids with traditional risk factors (red triangles). ROC analysis was performed to give area under the curve (panel A) and error rates (panel B). Error bars represent 95% confidence limits.

FIGS. 2(A) and (B) are graphical representations of the area under the curve and error rate resulting from control vs CAD models. Recursive feature elimination (RFE) with three-fold cross validation (repeated 100 times) was used to develop multivariate models using support vector machine learning. This was done for models of varying feature size (e.g., 1, 2, 4, 8, 16, 32 and 64) and for models that included either traditional risk factors alone (blue circles) lipids alone (green squares) or lipids with traditional risk factors (red triangles). ROC analysis was performed to give area under the curve (panel A) and error rates (panel B). Error bars represent 95% confidence limits.

FIGS. 5A-5D provide graphical representations of data showing recursive feature elimination analysis of CAD. Multivariate models containing different numbers of lipids alone (circles) or traditional risk factors (squares) or combined lipids and risk factors (triangles) were created to discriminate between control and CAD (left panels) and between stable and unstable CAD (right panels). C-statistics (top panels) and % accuracy (lower panels) with 95% confidence intervals for each model are plotted against the number of variables in the model.

BRIEF DESCRIPTION OF THE TABLES

Figure 3:
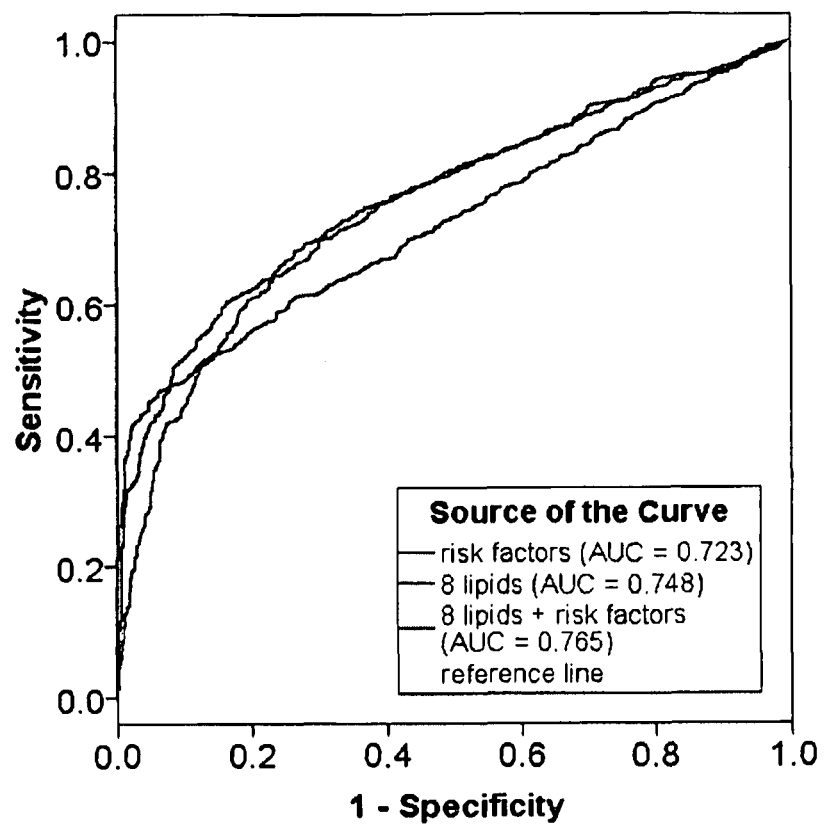
FIG. 3 is a graphical representation of ROC analysis of classification models of stable CAD vs unstable CAD. Multivariate models created with either the 13 traditional risk factors (Table 5), the 8 highest tanked lipids (Table 13) or a combination of both were validated by three-fold cross validation repeated 10 times and the results combined in a ROC analyses.

Table 1 provides a numbered list of 331 lipid analytes (biomarkers) identified in predetermined control vulnerable or non-vulnerable subjects, normal (healthy) subjects or heart disease subjects. Numbers prefaced by "s" identify internal standards used as internal controls for lipid analysis as described in the Examples.

Table 2 provides a description of the internal standard mix composition and concentration.

Table 3 provides mass spectrometer settings used for precursor ion scans.

Table 4 tabulates the scan methods used to create MRM acquisition methods for plasma lipid profiling for each lipid class.

Table 5 provides clinical and biochemical characteristics of patients.

Table 6 provides the medication of stable and unstable CAD cohorts.

Table 7 provides details of lipid analytes measured in MRM experiment 1 as described in the Examples.

Table 8 provides details of lipid analytes measured in MRM experiment 2 as described in the Examples.

Table 9 provides details of lipid analyte levels in stable and unstable cohorts.

Table 9a provides details of lipid analyte levels in control and CAD cohorts (continued).

Table 10 provides a summary of the univariate analysis of plasma lipids in control, stable CAD and unstable CAD cohorts.

Table 11 provides an analysis of variance of stable vs unstable cohorts.

Table 12 provides an analysis of variance of control vs CAD cohorts.

Table 13 provides ranked list of analytes based on recursive feature elimination of stable and unstable CAD cohorts.

Table 14 provides a ranked list of analytes based on recursive feature elimination of control vs CAD.

Table 15 provides final conditions for precursor ion scan and MRM acquisition methods for lipid identification and quantification.

Table 16 provides a final summary of univariate analysis of plasma lipids in control, CAD, stable CAD and unstable CAD groups.

Table 17 provides logistic regression models of stable CAD vs unstable CAD and logistic regression models of control vs CAD.

Table 18 provides ranked lipids in the stable CAD vs unstable CAD logistic model.

Table 19 provides ranked risk factors in the stable CAD vs unstable CAD logistic models.

Table 20 provides ranked features in the stable CAD vs unstable CAD logistic model.

Table 21 provides ranked lipids in the control vs CAD logistic model.

Table 22 provides ranked risk factors in the control vs CAD logistic model.

Table 23 provides ranked features in the control vs CAD logistic model.

Table 24 provides ranked features in the stable CAD vs unstable CAD recursive feature elimination models.

Table 25 provides ranked features in the control vs CAD recursive feature elimination models.

Table 26 provides a description of the lipid species affected by statin use.

Table 27 provides the medication of stable and unstable CAD cohorts.

DETAILED DESCRIPTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in the subject specification, the singular forms "a", "an" and "the" include plural aspects unless the context clearly dictates otherwise. Thus, for example, reference to "a biomarker" includes a single biomarker, as well as two or more biomarkers; reference to "an analyte" includes a single analyte or two or more analytes; reference to "the invention" includes single and multiple aspects of the invention; and so forth.

The use of numerical values in the various ranges specified in this application, unless expressly indicated otherwise, are stated as approximations as though the minimum and maximum values within the stated ranges were both preceded by the word "about". In this manner, slight variations above and below the stated ranges can be used to achieve substantially the same results as values within the ranges. Also, the disclosure of these ranges is intended as a continuous range including every value between the minimum and maximum values. In addition, the present invention extends to ratios of two or more markers providing a numerical value associated with a level of risk of heart disease development or presence.

A rapid, efficient and sensitive assay is provided for the stratification of heart disease in symptomatic and asymptomatic subject.

"Stratification" includes identification, diagnosing, clarification, monitoring and/or determination of the presence, level, severity, state and/or classification of heart disease. Generally, this is based on comparing a knowledge base of levels or ratios of lipid analytes in body fluid or tissue extract to another knowledge base of predetermined levels, statistically correlated to heart disease or a condition or symptom within the spectrum of heart disease.

Hence, the present invention identifies a correlation between the level or ratios of particular lipid analytes in a subject and heart disease. The term "heart disease" as used herein is to be considered as an individual condition as well as a spectrum of conditions including a range of risk indicators of the level of disease progression. This risk ranges from minor to extreme. The ability to monitor and identify markers of heart disease enables decisions on the type of medical intervention required from behavioural modification and medicaments to surgical intervention. This is particularly the case with asymptomatic individuals or those having a family history of heart disease.

The present invention extends to any or all conditions within the clinical spectrum of "heart disease".

Such conditions include, without being limited to, cardiomyopathies, such as, alcoholic cardiomyopathy, coronary artery disease, congenital heart disease, nutritional diseases affecting the heart, ischemic (or ischaemic) cardiomyopathy, hypertensive cardiomyopathy, valvular cardiomyopathy, inflammatory cardiomyopathy, cardiovascular disease, such as atherosclerosis, ischaemic heart disease, heart failure, hypertensive heart disease, such as, left ventricular hypertrophy, coronary heart disease, (congestive) heart failure, hypertensive cardiomyopathy, cardiac arrhythmias, inflammatory heart disease, such as, endocarditis, inflammatory cardiomegaly, myocarditis, valvular heart disease, such as, aortic valve stenosis, mitral valve prolapse and valvular cardiomyopathy Reference herein to a "subject" includes a human which may also be considered an individual, patient, host, recipient or target. The subject may also be an animal or an animal model. The term "analyte" includes a biomarker, marker, indicator, risk factor and the like.

The lipidomic approach uses one or more of three groups of lipid analytes:
  (i) modified ceramides (modCER), modified phosphatidylcholines (modPC) and modified cholesterol esters (modCE) selected from those listed in Table 1;
  (ii) two or more non-modified lipid analytes selected from the list in Table 1; and/or
  (iii) two or more lipid analytes wherein at least one is a modified lipid analyte (modCER, modPC and/or modCE) and at least one is a non-modified lipid analyte selected from the list in Table 1.

Accordingly, one aspect of the present invention is directed to an assay to stratify a subject as a vulnerable or non-vulnerable subject with respect to plaques, the assay comprising determining the levels of a lipid analyte selected from the list consisting of:
  (i) one or more modified lipid analytes listed in Table 1;
  (ii) two or more non-modified lipid analytes listed in Table 1, and
  (iii) two or more lipid analytes wherein at least one is a modified lipid analyte listed in Table 1 and at least one is a non-modified lipid analyte listed in Table 1;
wherein the level or ratio of the lipid analyte or analytes relative to a control identifies the subject as being vulnerable or non-vulnerable.

The present invention enables, therefore, a risk profile to be determined for a subject based on a lipidomic profile. The stratification or profiling enables early diagnosis, conformation of a clinical diagnosis, treatment monitoring and treatment selection.

In a particular embodiment, the lipidomic profile is associated with heart disease, the predisposition of development and/or the risk level for severity and progression.

In, a particular embodiment, the invention provides an assay to stratify a subject as a vulnerable or non-vulnerable subject with respect to plaques, the assay comprising determining the levels of at least two lipid analytes selected from the list consisting of:
  (i) one or more modified lipid analytes listed in Table 1;
  (ii) two or more non-modified lipid analytes listed in Table 1; and/or
  (iii) two or more lipid analytes wherein at least one is a modified lipid analyte listed in Table 1 and at least one is a non-modified lipid analyte listed in Table 1;
wherein the level of an individual lipid analyte listed in Table 1 is different between vulnerable subjects and non-vulnerable subjects and wherein the level of the lipid analytes in the subject relative to a control identifies the subject as being vulnerable or non-vulnerable.

In another embodiment, the assays comprise comparing the level of the at least two lipid analytes in the subject to the respective levels of the same lipid analytes in at least one control subject selected from a vulnerable subject and a non-vulnerable subject, wherein a similarity in the respective levels of the at least two lipid analytes between the subject and the non-vulnerable subject identifies the subject as being non-vulnerable, and wherein a similarity in the respective levels of the at least two lipid analytes between the subject and the vulnerable subject identifies the subject as being vulnerable.

Reference to a "control" broadly includes data that the skilled person would use to facilitate the accurate interpretation of technical data. In an illustrative example, the level or levels of lipid analyte(s) from a subject are compared to the respective level or levels of the same lipid analyte(s) in one or more cohorts (populations/groups) of control subjects selected from a vulnerable subject cohort wherein the subjects have been diagnosed with unstable heart disease, a non-vulnerable subject cohort wherein the subjects have been diagnosed with stable heart disease, a normal subject cohort wherein the subjects have been predetermined not to have heart disease, and a heart disease subject cohort that comprises the members of the vulnerable and non-vulnerable cohorts. In some embodiments, the control may be the level or ratio of one or more lipid analytes in a sample from the test subject taken at an earlier time point. Thus, a temporal change in analyte levels can be used to identify vulnerability or provide a correlation as to the state of heart diseases. In some embodiments, the relative levels of two or more lipid analytes provides a useful control.

In some embodiments, a control subject is a group of control subjects. The level of analytes in a control subject group may be a mean value or a preselected level, threshold or range of levels that define, characterise or distinguish a particular group. Thresholds may be selected that provide an acceptable ability to predict diagnostic or prognostic risk, treatment success, etc. In illustrative examples, receiver operating characteristic (ROC) curves are calculated by plotting the value of one or more variables versus its relative frequency in two populations (called arbitrarily "disease" and "normal" or "low risk" and "high risk" groups for example). For any particular lipid analyte(s) or class(es), a distribution of level(s) for subjects in the two populations will likely overlap. Under such conditions, a test level does not absolutely distinguish "disease" and "normal" or "vulnerable" and "non-vulnerable" with 100% accuracy, and the area of overlap indicates where the test cannot distinguish between groups. Accordingly, in some embodiments, a threshold or range is selected, above which (or below which, depending on how a lipid analyte level changes with heart disease or prognosis) the test is considered to be "positive" and below which the test is considered to be "negative". As described in Example 4, non-parametric tests were used to establish the statistical significance of differences between different analyte levels in the different control groups (See Table 16). Linear regression analysis was also used to identify lipid analytes that are independent predictors of group assignment. Several lipid analytes were found to be independent predictor of stable or unstable CAD, specifically PI 34:0, DHC 18:1, modCer 703.6.5.87, SM 22:1 and GM3 18:0. Similarly, twenty one lipid analytes were able to distinguish individually between control and CAD patients (Table 12, Model 6). Multivariate analysis is particularly suitable for developing a predictive model based on plasma lipid profiles. A range of models including different numbers of lipid analytes (1, 2, 4, 8, 16, 22, 64 . . . 329) either alone or with traditional risk factors were examined for their ability to distinguish a particular group (Tables 18 to 20). The values from these models were used to perform ROC analyses to determine the severity and specificity of the models (see Example 6, FIG. 6). Accordingly it is possible, as demonstrated, herein to use the full range of lipid analytes or to select particular subsets of lipid analytes capable of distinguishing between particular groups.

Alternatively, or in addition, thresholds may be established by obtaining an analyte level from the same patient, to which later results may be compared. In these embodiments, the individual in effect acts as their own "control group." In markers that increase with disease severity or prognostic risk, an increase over time in the same patient can indicate a worsening or development of disease or risk of disease or a failure of a treatment regimen, while a decrease over time can indicate remission of disease or success of a treatment regimen. Various further controls will be routinely applied by the skilled artisan. In an illustrative example, the levels of a range or panel of lipid analytes within one or more lipid class are determined and compared to predetermined levels in one or more control subject groups. Lipid analytes determined herein not to be correlated with heart disease or unstable plaques can be included as internal controls and are therefore also useful in some embodiments.

In some embodiments, lipid analyte levels in control groups are used to generate a profile of lipid analyte levels reflecting difference between levels in two control groups. Thus, a particular lipid analyte may be more abundant or less abundant in one control group compared to another control group. The data may be represented as an overall signature score or the profile may be represented as a barcode or other graphical representation. The lipid analyte levels from a test subject may be represented in the same way and similarity with the signature scope or level of "fit" to a signature barcode or other graphical representation may be determined. In other embodiments, the levels of a particular lipid analyte or lipid class are analysed and a downward or an upward trend in analyte level determined. Thus, for example, as shown in the Examples, the total PI species were 13.8% lower in unstable vs stable CAD, over and above a 13.5% decrease in the CAD group compared to control groups. In another Example, lower levels of LPC species (except LPC 20:4 and LPC 20:2) were found to be predictive of disease severity/unstable CAD, e.g. LPC 16:1 and LPC 14:0. In another example, SM1 018:0 was over represented in the unstable CAD group.

In another embodiment, the assays further comprise comparing the level of the at least two lipid analytes in the subject to the respective levels of the same lipid analytes in at least one normal subject, wherein a similarity in the respective levels of the at least two lipid analytes between the subject and the normal subject identifies the subject as being normal with respect to plaques.

In yet another embodiment, the assays comprise determining or determining and comparing the level of at least 2, 4, 6, 8, 10, 12, 14, 16, 18, 20, 22, 24, 26, 28, 30 or more lipid analytes including 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, or 331 biomarkers (lipid analytes).

In some embodiments, the lipid analytes are selected that fall within a single lipid class. Thus, in some embodiments, the level of two or more lipid analytes in one or more lipid classes are determined and compared.

In some particular embodiments, the assays further comprise determining the levels of at least two lipid analytes selected from the list consisting of:
  (i) one or more modified lipid analytes listed in Table 1;
  (ii) two or more non-modified lipid analytes listed in Table 1; and/or
  (iii) two or more lipid analytes wherein at least one is a modified lipid analytes listed in Table 1 and at least one is a non-modified lipid analyte listed in Table 1;
wherein the level of an individual lipid analyte listed in Table 1 is different between normal subjects and heart disease subjects and wherein the level of the lipid analytes in the subject relative to a control identifies the subject as being a normal subject or a heart disease subject.

In some embodiments, the or each modified lipid analyte in (i) is selected from a modified ceramide (modCER) and a modified phosphatidylcholine (modPC).

In other embodiments, the non-modified lipid analytes in (ii) are selected from a dihexosylceramide (DHC), a sphingomyelin (SM), a phosphatidylinositol (PI), a lysophosphatidylcholine (LPC), a phosphatidylcholine (PC), an alkylphosphatidylcholine (APC), a cholesterol ester (CE), a diacylglycerol (DG) and a triacylglycerol (TG).

In still further embodiments of the assay, the or each modified lipid analyte in (iii) is selected from a modified ceramide (modCER) and a modified phosphatidylcholine (modPC) and the or each non-modified lipid in (iii) is selected from a dihexosylceramide (DHC), a sphingomyelin (SM), a phosphatidylinositol (PI), a lysophosphatidylcholine (LPC), a alkylphosphatidylcholine (APC), a cholesterol ester (CE), a diacylglycerol (DG) and a triacylglycerol (TG).

In another embodiment, the assays comprise determining the levels of at least two lipid analytes selected from modCer 731.6, GM3 18:0, PC34:5, DHC 18:1, APC 34:2, SM 18:0, Cer 18:1, PI 36:1, APC 36:0, DG 18:1 20:0, LPC 14:0, LPC 16:1, PC 24:0, Cer 18:0, PI 36:3, PI 38:2, modPC.622.4/40, LPC 18:2, LPC 24:0, PC 34:3, modPC 752.6/5.58, PI 34:0, modCer 703.6/5.87 and SM 22:1.

In another embodiment, the assays comprise determining the levels of at least four, six, eight or sixteen lipid analytes selected from the group consisting of modCer 731.6, GM3 18:0, PC34:5, DHC 18:1, APC 34:2, SM 18:0, Cer 18:1, PI 36:1, APC 36:0, DG 18:1 20:0, LPC 14:0, LPC 16:1, PC 24:0, Cer 18:0, PI 36:3, PI 38:2, modPC.622.4/40, LPC 18:2, LPC 24:0, PC 34:3, modPC 752.6/5.58, PI 34:0, modCer 703.6/5.87 and SM 22:1.

In particular embodiments, the assayed levels of lipid analytes are used in combination with one or more traditional risk factors selected from age, sex, smoker, diabetes, hypertension, CAD family history, BMI, total cholesterol, LDL, HDL, triglycerides, glucose and hsCRP to thereby identify the subject as being vulnerable or non-vulnerable.

Suitably, the assays comprise, in some embodiments, comparing the level of the at least two lipid analytes in the subject to the respective levels of the same lipid analytes in at least one control subject selected from a normal subject and a heart disease subject, wherein a similarity in the respective levels of the at least two lipid analytes between the subject and the heart disease subject identifies the subject as having heart disease, and wherein a similarity in the respective levels of the at least two lipid analytes between the subject and the normal subject identifies the subject as being normal with respect to heart disease.

In yet another embodiment, the assays comprise determining or determining and comparing the levels of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 lipid analytes, preferably 8, 9, 10, 11, 12, 13, 14, 15 or 16 lipid analytes in Table 1 wherein the level of an individual lipid analyte listed in Table 1 is different between normal subjects and heart disease subjects. In some embodiments, any number between 2 and 331 lipid analytes include but 2 and 18 lipid analytes or any number between 2 and 18 lipid classes including 2, 3, 4, 5, 6, 7, 8, 9, 10, 11, 12, 13, 14, 15, 16, 17 or 18 lipid classes are analysed.

In some embodiments, the modified lipid analyte in (i) is one or more of a modified ceramide (modCER) and a modified phosphatidylcholine (modPC).

In other embodiments, the non-modified lipid analyte in (ii) is two or more of a ceramide (CER), monohexosylceramide (MHC), dihexosylceramide (DHC), trihexosylceramide (THC), GM3 Ganglioside (GM3), modified ceramides (modCer), sphingomyelin (SM), phosphatidylserine (PS), phosphatidylinositol (PI), lysophosphatidylcholine (LPC), lysoplatelet activating factor (LPAF), phosphatidylcholine (PC), odd-chain phosphatidylcholine (oddPC), alkylphosphatidylcholine (APC), modified phosphatidylcholine (modPC), cholesterol esters (CE), diacylglycerol (DG), and triacylglycerol (TG).

In still further embodiments, the or each modified lipid analyte in (iii) is one or more of a modified ceramide (modCER) and a modified phosphatidylcholine (modPC) and the or each non-modified lipid in (iii) is selected from a ceramide (CER), a monohexosylceramide (MHC), a dihexosylceramide (DHC), trihexosylceramide (THC), GM3 Ganglioside (GM3), modified ceramides (modCer), sphingomyelin (SM), phosphatidylserine (PS), phosphatidylinositol (PI), lysophosphatidylcholine (LPC), lysoplatelet activating factor (LPAF), phosphatidylcholine (PC), odd-chain phosphatidylcholine (oddPC), alkylphosphatidylcholine (APC), modified phosphatidylcholine (modPC), cholesterol esters (CE), diacylglycerol (DG) and a triacylglycerol (TG).

In an illustrative example, the lipid analytes are two or more of LPC 22:0, PS 40:6, PI 34:0, Cer 20:0, Cer 18:0, APC 34:2, PC 34:5, LPC 20:3, PC 28:0, modPC 692.4/5.8, APC 30:0, modPC 736.5/5.7, LPC 20:4, APC 38:6, modPC 720.5.4.5, PI 36:0, LPC 24:0, PS 40:5, LPC 20:0, modPC 877.6/6.0 and CE 22:4.

In a further illustrative example, the lipid analytes are two or more of LPC 22:0, PS 40:6, PI 34:0, Cer 20:0, Cer 18:0, APC 34:2, PC 34:5, LPC 20:3, PC 28:0, modPC 692.4/5.8, APC 30:0, modPC 736.5/5.7, LPC 20:4, APC 38:6, modPC 720.5.4.5, PI 36:0, LPC 24:0, PS 40:5, LPC 20:0, modPC 877.6/6.0, CE 22:4, ModPC 580.4/4.84, PS 40:6, modPC 752.6/5.58, APC 32:1, oddPC 37:3, GM3 24:1, oddPC 33:0, APC 36:0, CE 24:3, SM 20:1, SM 18:0, LPC 20:0, modCE 682.7/8.76, COH, Cer 20:0, LPC 16:1, TG 16:1 16:1 16:1, modPC 564.4/4.70, modPC 720.6/4.52, modPC 608.4/5.33, PE 38:3, PE 38:1, modPC 580.4/4.84, PS 40:6, GM3 22:0, PC 37:3, PC 33:0, modPC 788.6/5.19, C24:3, C24:4, modPC 666.4/2.99, modPC 678.4/4.37, modCer 731.6/6.22, SM 18:1, APC 36:5, modPC 769.6/6.25, APC 36:3, oddPC 35:4, PG 18:1 18:1, TG 18:1 18:1 18:2, modPC 881.7/6.05, CE 17:0 and PI 38:5.

In another illustrative example, the lipid analytes are four or more, six or more, eight or more or sixteen or more of LPC 22:0, PS 40:6, PI 34:0, Cer 20:0, Cer 18:0, APC 34:2, PC 34:5, LPC 20:3, PC 28:0, modPC 692.4/5.8, APC 30:0, modPC 736.5/5.7, LPC 20:4, APC 38:6, modPC 720.5.4.5, PI 36:0, LPC 24:0, PS 40:5, LPC 20:0, modPC 877.6/6.0, CE 22:4, ModPC 580.4/4.84, PS 40:6, modPC 752.6/5.58, APC 32:1, oddPC 37:3, GM3 24:1, oddPC 33:0, APC 36:0, CE 24:3, SM 20:1, SM 18:0, LPC 20:0, modCE 682.7/8.76, COH, Cer 20:0, LPC 16:1, TG 16:1 16:1 16:1, modPC 564.4/4.70, modPC 720.6/4.52, modPC 608.4/5.33, PE 38:3, PE 38:1, modPC 580.4/4.84, PS 40:6, GM3 22:0, PC 37:3, PC 33:0, modPC 788.6/5.19, C24:3, C24:4, modPC 666.4/2.99, modPC 678.4/4.37, modCer 731.6/6.22, SM 18:1, APC 36:5, modPC 769.6/6.25, APC 36:3, oddPC 35:4, PG 18:1 18:1, TG 18:1 18:1 18:2, modPC 881.7/6.05, CE 17:0 and PI 38:5.

In some further embodiments, the assayed levels of lipid analytes are used in combination with one or more traditional risk factors selected from age, sex, smoker, diabetes, hypertension, CAD family history, BMI, total cholesterol, LDL, HDL, triglycerides, glucose and hsCRP to thereby identify the subject as being normal or having heart disease.

In a different embodiment, the present invention contemplates an assay to stratify a subject with respect to heart disease, the assay comprising determining the levels of a lipid analyte selected from the list consisting of:

(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;

wherein the level or ratio of the lipid analyte or analytes relative to a control provides a indication or correlation as to the presence, absence state, classification or progression of heart disease.

In particular embodiments, the invention provides an assay to stratify a subject with respect to heart disease, the assay comprising determining the levels of at least two lipid analytes selected from the list consisting of:

(i) one or more modified lipid analytes listed in Table 1;
(ii) two or more non-modified lipid analytes listed in Table 1, and/or
(iii) two or more lipid analytes wherein at least one is a modified lipid analyte listed in Table 1 and at least one is a non-modified lipid analyte listed in Table 1;

wherein the level of an individual lipid analyte listed in Table 1 is different between normal and heart disease subjects and wherein the level of the lipid analytes in the subject relative to a control provides an indication of the presence or absence of heart disease.

In some embodiments, the assays comprise comparing the level of the at least two lipid analytes in the subject to the respective levels of the same lipid analytes in at least one control subject selected from a normal subject and a heart disease subject, wherein a similarity in the respective levels of the at least two lipid analytes between the subject and the heart disease subject identifies the subject having heart disease, and wherein a similarity in the respective levels of the at least two lipid analytes between the subject and the normal subject identifies the subject as a normal subject with respect to heart disease.

In illustrative embodiments, the assays comprise determining or determining and comparing the levels of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39; 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95, preferably at least 4, 5, 6, 7, 8, 9, 10, 11, 12, 13, 14, 15 or 16 lipid analytes wherein the level of an individual lipid analyte listed in Table 1 is different between normal and heart disease subjects.

In some embodiments, the modified lipid analyte in (i) is one or more of a modified ceramide (modCER) and a modified phosphatidylcholine (modPC).

In other embodiments, the non-modified lipid analyte in (ii) is two or more of a ceramide (CER), monohexosylceramide (MHC), dihexosylceramide (DHC), trihexosylceramide (THC), GM3 Ganglioside (GM3), modified ceramides (modCer), sphingomyelin (SM), phosphatidylserine (PS), phosphatidylinositol (PI), lysophosphatidylcholine (LPC), lysoplatelet activating factor (LPAF), phosphatidylcholine (PC), odd-chain phosphatidylcholine (oddPC), alkylphosphatidylcholine (APC), modified phosphatidylcholine (modPC), cholesterol esters (CE), diacylglycerol (DG), and triacylglycerol (TG).

In still further embodiments, the or each modified lipid analyte in (iii) is one or more of a modified ceramide (modCER) and a modified phosphatidylcholine (modPC) and the or each non-modified lipid in (iii) is selected from a ceramide (CER), a monohexosylceramide (MHC), a dihexosylceramide (DHC), trihexosylceramide (THC), GM3 Ganglioside (GM3), modified ceramides (modCer), sphingomyelin (SM), phosphatidylserine (PS), phosphatidylinositol (PI), lysophosphatidylcholine (LPC), lysoplatelet activating factor (LPAF), phosphatidylcholine (PC), odd-chain phosphatidylcholine (oddPC), alkylphosphatidylcholine (APC), modified phosphatidylcholine (modPC), cholesterol esters (CE), diacylglycerol (DG) and a triacylglycerol (TG).

In an illustrative example, the lipid analytes are two or more of LPC 22:0, PS 40:6, PI 34:0, Cer 20:0, Cer 18:0, APC 34:2, PC 34:5, LPC 20:3, PC 28:0, modPC 692.4/5.8, APC 30:0, modPC 736.5/5.7, LPC 20:4, APC 38:6, modPC 720.5.4.5, PI 36:0, LPC 24:0, PS 40:5, LPC 20:0, modPC 877.6/6.0, CE 22:4, ModPC 580.4/4.84, PS 40:6, modPC 752.6/5.58, APC 32:1, oddPC 37:3, GM3 24:1, oddPC 33:0, APC 36:0, CE 24:3, SM 20:1, SM 18:0, LPC 20:0, modCE 682.7/8.76, COH, Cer 20:0, LPC 16:1, TG 16:1 16:1 16:1, modPC 564.4/4.70, modPC 720.6/4.52, modPC 608.4/5.33, PE 38:3, PE 38:1, modPC 580.4/4.84, PS 40:6, GM3 22:0, PC 37:3, PC 33:0, modPC 788.6/5.19, C24:3, C24:4, modPC 666.4/2.99, modPC 678.4/4.37, modCer 731.6/6.22, SM 18:1, APC 36:5, modPC 769.6/6.25, APC 36:3, oddPC 35:4, PG 18:1 18:1, TG 18:1 18:1 18:2, modPC 881.7/6.05, CE 17:0 and PI 38:5.

In another illustrative example, the lipid analytes are four or more, six or more, eight or more or sixteen or more of LPC 22:0, PS 40:6, PI 34:0, Cer 20:0, Cer 18:0, APC 34:2, PC 34:5, LPC 20:3, PC 28:0, modPC 692.4/5.8, APC 30:0, modPC 736.5/5.7, LPC 20:4, APC 38:6, modPC 720.5.4.5, PI 36:0, LPC 24:0, PS 40:5, LPC 20:0, modPC 877.6/6.0, CE 22:4, ModPC 580.4/4.84, PS 40:6, modPC 752.6/5.58; APC 32:1, oddPC 37:3, GM3 24:1, oddPC 33:0, APC 36:0, CE 24:3, SM 20:1, SM 18:0, LPC 20:0, modCE 682.7/8.76, COH, Cer 20:0, LPC 16:1, TG 16:1 16:1 16:1, modPC 564.4/4.70, modPC 720.6/4.52, modPC 608.4/5.33, PE 38:3, PE 38:1, modPC 580.4/4.84, PS 40:6, GM3 22:0, PC 37:3, PC 33:0, modPC 788.6/5.19, C24:3, C24:4, modPC 666.4/2.99, modPC 678.4/4.37, modCer 731.6/6.22, SM 18:1, APC 36:5, modPC 769.6/6.25, APC 36:3, oddPC 35:4, PG 18:1 18:1, TG 18:1 18:1 18:2, modPC 881.7/6.05, CE 17:0 and PI 38:5.

In some further embodiments, the assayed levels of lipid analytes are used in combination with one or more traditional risk factors selected from age, sex, smoker, diabetes, hypertension, CAD family history, BMI, total cholesterol, LDL, HDL, triglycerides, glucose and hsCRP to thereby identify the subject as being normal or having heart disease.

Still another aspect of the present invention contemplates the use of a panel of lipid analytes selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
in the manufacture of an assay to identify the presence, state, classification or progression of heart disease in a subject.

In some embodiments, lipid analytes are two or more selected from a ceramide (Cer) including Cer 16:0, Cer 18:1, Cer 18:0, Cer 20:0, Cer 22:0, Cer 24:1, Cer 24:0; a monohexosylceramide (MHC) including MHC 16:0, MHC 18:1, MHC 18:0, MHC 20:0, MHC 22:0, MHC 24:1, MHC 24:0; a dihexosylceramide (DHC) including DHC 16:0, DHC 18:1, DHC 18:0, DHC 20:0, DHC 22:0, DHC 24:1, DHC 24:0; a trihexosylcermide (THC) including THC 16:0, THC 18:1, THC 18:0, THC 20:0, THC 22:0, THC 24:1, THC 24:0; a GM3 ganglioside (GM3) including GM3 16:0, GM3 18:0, GM3 20:0, GM3 22:0, GM3 24:1, GM3 24:0; a sphingomyelin (SM) including SM 14:0, SM 15:0, SM 16:1, SM 16:0, SM 18:1, SM 18:0, SM 20:1, SM 22:1, SM 22:0, SM 24:2, SM 24:1, SM 24:0; a phosphatidylglycerol (PG) including PG 16:1 18:1, PG 16:0 18:1, PG 18:1 18:1, PG 18:0 18:1; a bis(monoacylglycerol)phosphate (BMP) including BMP 18:1 18:1; phosphatidylserine (PS) including PS 36:2, PS 36:1, PS 38:5, PS 38:4, PS 38:3, PS 40:6, PS 40:5; phosphatidylethanolamine (PE) including PE 32:1, PE 32:0, PE 34:2, PE 34:1, PE 36:5, PE 36:4, PE 36:3, PE 36:2, PE 36:1, PE 36:0, PE 38:6, PE 38:5, PE 38:4, PE 38:3, PE 38:2, PE 38:1, PE 40:7, PE 40:6; a phosphatidylinositol (PI) including PI 32:1, PI 32:0, PI 34:1, PI 34:0, PI 36:4, PI 36:3, PI 36:2, PI 36:1, PI 36:0, PI 38:6, PI 38:5, PI 38:4, PI 38:3, PI 38:2, PI 40:6, PI 40:5, PI 40:4; a lysophosphatidylcholine (LPC) including LPC 14:0, LPC 15:0, LPC 16:1, LPC 16:0, LPC 18:2, LPC 18:1, LPC 18:0, LPC 20:5 LPC 20:4, LPC 20:3, LPC 20:2, LPC 20:1, LPC 20:0, LPC 22:6; a lysoplatelet activating factor (LPAF) including LPAF 16:0, LPAF 18:1, LPAF 18:0; a phosphatidylcholine (PC) including PC 30:2, PC 32:2, PC 32:1, PC 32:0, PC 34:3, PC 34:2, PC 34:1, PC 34:0, PC 36:5, PC 36:4, PC 36:3, PC 36:2, PC 38:6, PC 38:5, PC 38:4, PC 40:7, PC 40:6, PC 40:5, PC 44:12; an alkylphosphatidylcholine (APC) including APC 32:1, APC 32:0, APC 34:2, APC 34:1, APC 34:0, APC 36:5, APC 36:4, APC 36:3, APC 36:2, APC 36:1, APC 36:0, APC 38:6, APC 38:5, APC 38:4, APC 38:3, APC 38:2; a cholesterol ester (CE) including CE 14:0, CE 15:0, CE 16:2, CE 16:1, CE 16:0, CE 17:1, CE 17:0, CE 18:3, CE 18:2, CE 18:1, CE 18:0, CE 20:5, CE 20:4, CE 20:3, CE 20:2, CE 20:1, CE 22:6, CE 22:5, CE 22:4, CE 22:3, CE 22:2, CE 22:1, CE 22:0, CE 24:6, CE 24:5, CE 24:4, CE 24:3, CE 24:2, CE 24:1, CE 24:0; a diacylglycerol (DG) including DG 14:0 14:0, DG 14:1 16:0, DG 14:0 16:0, DG 14:0 18:2, DG 14:0 18:1, DG 16:0 16:0, DG 16:0 18:2, DG 16:1 18:1, DG 16:0 18:1, DG 18:0 16:1, DG 16:0 18:0, DG 16:0 20:4, DG 18:1 18:3, DG 18:2 18:2, DG 16:0 20:3, DG 18:1 18:2, DG 18:0 18:2, DG 18:1 18:1, DG 18:0 18:1, DG 16:0 20:0, DG 18:0 18:0, DG 16:0 22:6, DG 16:0 22:5, DG 18:1 20:4, DG 18:0 20:4, DG 18:1 20:3, DG 18:1 20:0; and a triaclyglycerol (TG) including TG 14:0 16:1 18:2, TG 16:1 16:1 16:1, TG 14:0 16:0 18:2, TG 14:0 16:1 18:1, TG 14:1 16:0 18:1, TG 14:1 16:1 18:0, TG 18:1 14:0 16:0, TG 16:0 16:0, TG 15:0 18:1 16:0, TG 17:0 16:0 16:1, TG 17:0 18:1 14:0, TG 14:0 18:2 18:2, TG 14:1 18:0 18:2, TG 14:1

18:1 18:1, TG 16:1 16:1 18:1, TG 16:0 16:0 18:2, TG 16:1 16:1 18:0, TG 16:0 16:1 18:1, TG 14:0 18:0 18:1, TG 16:0 16:0 18:1, TG 16:0 16:0 18:0, TG 15:0 18:1 18:1, TG 17:0 18:1 16:1, TG 17:0 18:2 16:0, TG 17:0 18:1 16:0, TG 17:0 16:0 18:0, TG 16:0 18:2 18:2, TG 16:1 18:1 18:2, TG 16:1 18:1 18:1, TG 16:0 18:1 18:2, TG 16:0 18:1 18:1, TG 16:0 18:0 18:1, TG 17:0 18:1 18:1, TG 18:2 18:2 18:2, TG 18:1 18:2 18:2, TG 18:0 18:2 18:2, TG 18:1 18:1 18:2, TG 18:1 18:1 18:1, TG 18:0 18:1 18:1, TG 18:0 18:0 18:1, TG 18:0 18:0 18:0, TG 18:2 18:2 20:4, TG 18:1 18:1 20:4, TG 18:1 18:1 22:6; a modified ceramide (modCer) including modCer 576.5/7.68, modCer 614.6/5.72, modCer 632.6/9.22, modCer 651.6/7.56, modCer 703.6/5.87, modCer 731.6/6.22, modCer 766.6/7.17, modCer 769.6/8.01, modCer 798.7/7.29, modCer 875.7/9.23, modCer 883.8/7.75, modCer 886.8/9.06, modCer 910.8/8.98, modCer 921.8/9.05; phosphatidylcholine (modPC) including modPC 506.3/3.50, modPC 508.3/3.30, modPC 510.3/4.00, modPC 512.3/1.70, modPC 536.3/3.50, modPC 538.3/4.10, modPC 552.4/3.90, modPC 564.4/4.70, modPC 566.4/5.10, modPC 580.4/4.84, modPC 594.4/3.26, modPC 608.4/3.84, modPC 610.4/2.03, modPC 622.4/4.54, modPC 633.4/4.51, modPC 636.4/3.37, modPC 645.4/4.49, modPC 650.4/3.24, modPC 650.4/4.44, modPC 650.4/3.94, modPC 664.4/4.22, modPC 666.4/2.99, modPC 678.4/4.37, modPC 678.4/4.94, modPC 678.4/5.51, modPC 690.4/4.11, modPC 690.4/4.90, modPC 690.4/6.00, modPC 692.4/5.05, modPC 692.4/5.52, modPC 692.4/6.10, modPC 694.4/6.20, modPC 703.5/4.09, modPC 704.5/3.81, modPC 706.5/3.79, modPC 720.5/4.52, modPC 736.5/5.38, modPC 743.5/5.91, modPC 752.5/5.58, modPC 772.5/5.37, modPC 773.6/6.47, modPC 788.6/5.19, modPC 801.6/6.70, modPC 816.6/5.58, modPC 818.6/6.10, modPC 818.6/6.48, modPC 828.6/6.03, modPC 843.6/7.10, modPC 866.6/7.24, modPC 878.6/5.98, modPC 881.6/6.05; and a cholesterol ester (modCE) including modCE 558.5/7.74, modCE 588.5/7.94, modCE 682.7/8.76, modCE 790.8/6.57.

The lipidomic profile further enables determination of endpoints in pharmacotranslational studies. For example, clinical trials can take many months or even years to establish the pharmacological parameters for a medicament to be used in coronary care. However, these parameters may be associated with a lipidomic profile associated with a health state. Hence, the clinical trial can be expedited by first selecting a medicament and pharmaceutical parameters which result in a lipidomic profile associated with the desired health state.

Accordingly, another aspect of the present invention contemplates a method for determining the pharmacoefficacy of a medicament for use in heart disease treatment, the method comprising selecting a medicament and its concentration and/or formulation parameters which provide a lipidomic profile associated or characteristic of a healthy individual, the lipidomic profile identified by determining the levels of a lipid analyte selected from the list consisting of:

(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;

wherein the level or ratio of the lipid analyte or analytes relative to a control provides a correlation as to the presence, state, classification or progression of heart disease.

Another aspect of the present invention provides a method for conducting a clinical trial for a medicament for the treatment or prophylaxis of heart disease, the method comprising conducting the clinical trial using a formulation of the medicament which generates a lipidomic profile associated or characteristic of a healthy individual, the lipidomic profile identified by determining the levels of a lipid analyte selected from the list consisting of:

(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;

wherein the level or ratio of the lipid analyte or analytes relative to a control provides a correlation as to the presence, state, classification or progression of heart disease.

The lipidomic profile, therefore, can be used as a marker to define a desired state of health in an individual. It can be considered, therefore, a defined surrogate endpoint or desired endpoint in clinical management of subjects having heart disease treatment.

There are many methods which may be used to detect lipid analyte levels including mass spectrometry. In a particular, liquid chromatography, electrospray ionization-tandem mass spectrometry is used.

Immunological assays can also be done in any convenient formats known in the art. These include Western blots, immunohistochemical assays and ELISA assays. Any means for detecting a level of a lipid analyte can be used in accordance with the present invention.

The biological sample is any fluid or cell or tissue extract in a subject which comprises lipids. In one embodiment, the biological sample is a tissue of the heart or surrounding the heart. In another embodiment, the biological sample includes blood, plasma, serum, lymph, urine and saliva or cell extracts.

The present invention identifies the presence of a lipidomic profile associated with heart disease or a risk of developing same. In order to detect a lipid analyte, a biological sample is prepared and analyzed for a difference in levels or ratios of levels between the subject being tested and a control. In this context, a "control" includes the levels in a statistically significant normal population.

The identification of the association between the pathophysiology of heart disease and levels of or ratios of lipids permits the early presymptomatic screening of individuals to identify those at risk for developing heart disease or to identify the cause of such a disorder or the risk that any individual will develop same. The subject assay enables practitioners to identify or stratify individuals at risk for certain behavioural states associated with heart disease or its manifestations including an inability to overcome symptoms of heart disease after initial treatment. Certain behavioural or therapeutic or dietary protocols may then be introduced to reduce the risk of developing heart disease. Presymptomatic diagnosis will enable better treatment of heart disease, including the use of existing medical therapies. Lipidotyping of individuals is useful for (a) identifying a form of heart disease which will respond to particular drugs, (b) identifying types of heart disease which responds well to specific medications or medication types with fewer adverse effects and (c) guide new drug discovery and testing.

Even yet another aspect of the present invention relates to a method of treatment or prophylaxis of a subject comprising assaying the subject with respect to heart disease by determining the levels of a lipid analyte selected from the list consisting of:

(i) one or more modified lipid analytes listed in Table 1;
(ii) two or more non-modified lipid analytes listed in Table 1, and (iii) two or more lipid analytes wherein at least one is a modified lipid analyte listed in Table 1 and at least one is a non-modified lipid analyte listed in Table 1;

wherein the level or ratio of the lipid analyte or analytes relative to a control provides a correlation to the presence, state, classification or progression of heart disease and then providing therapeutic and/or behavioural modification to the subject.

The present invention further provides a web-based system where data on expression levels of lipids are provided by a client server to a central processor which analyses and compares to a control and optionally considers other information such as patient age, sex, weight and other medical conditions and then provides a report, such as, for example, a risk factor for disease severity or progression or status or an index of probability of heart disease in symptomatic or asymptomatic individuals.

Hence, knowledge-based computer software and hardware also form part of the present invention.

In particular, the assays of the present invention may be used in existing or newly developed knowledge-based architecture or platforms associated with pathology services. For example, results from the assays are transmitted via a communications network (e.g. the internet) to a processing system in which an algorithm is stored and used to generate a predicted posterior probability value which translates to the index of disease probability which is then forwarded to an end user in the form of a diagnostic or predictive report.

The assay may, therefore, be in the form of a kit or computer-based system which comprises the reagents necessary to detect the concentration of the lipid biomarkers and the computer hardware and/or software to facilitate determination and transmission of reports to a clinician.

The assay of the present invention permits integration into existing or newly developed pathology architecture or platform systems. For example, the present invention contemplates a method of allowing a user to determine the status of a subject with respect to a heart disease or subtype thereof or stage of heart disease, the method including:

(a) receiving data in the form of levels or concentrations of a lipid analyte selected from the list consisting of:
  (i) one or more modified lipid analytes listed in Table 1;
  (ii) two or more non-modified lipid analytes listed in Table 1, and
  (iii) two or more lipid analytes wherein at least one is a modified lipid analyte listed in Table 1 and at least one is a non-modified lipid analyte listed in Table 1;
  wherein the level or ratio of the lipid analyte or analytes relative to a control provides a correlation to the presence, state, classification or progression of heart disease;
  from the user via a communications network;
(b) processing the subject data via multivariate analysis to provide a disease index value;
(c) determining the status of the subject in accordance with the results of the disease index value in comparison with predetermined values; and
(d) transferring an indication of the status of the subject to the user via the communications network reference to the multivariate analysis includes an algorithm which performs the multivariate or univariate analysis function.

Conveniently, the method generally further includes:
(a) having the user determine the data using a remote end station; and
(b) transferring the data from the end station to the base station via the communications network.

The base station can include first and second processing systems, in which case the method can include:
(a) transferring the data to the first processing system;
(b) transferring the data to the second processing system; and
(c) causing the first processing system to perform the multivariate analysis function to generate the disease index value.

The method may also include:
(a) transferring the results of the multivariate analysis function to the first processing system; and
(b) causing the first processing system to determine the status of the subject.

In this case, the method also includes at least one of:
(a) transferring the data between the communications network and the first processing system through a first firewall; and
(b) transferring the data between the first and the second processing systems through a second firewall.

The second processing system may be coupled to a database adapted to store predetermined data and/or the multivariate analysis function, the method include:
(a) querying the database to obtain at least selected predetermined data or access to the multivariate analysis function from the database; and
(b) comparing the selected predetermined data to the subject data or generating a predicted probability index.

The second processing system can be coupled to a database, the method including storing the data in the database.

The method can also include having the user determine the data using a secure array, the secure array of elements capable of determining the level of biomarker and having a number of features each located at respective position(s) on the respective code.

In this case, the method typically includes causing the base station to:
(a) determine the code from the data;
(b) determine a layout indicating the position of each feature on the array; and
(c) determine the parameter values in accordance with the determined layout, and the data.

The method can also include causing the base station to:
(a) determine payment information, the payment information representing the provision of payment by the user; and
(b) perform the comparison in response to the determination of the payment information.

The present invention also provides a base station for determining the status of a subject with respect to a heart disease or a subtype thereof or a stage of heart disease, the base station including:
(a) a store method;
(b) a processing system, the processing system being adapted to:
(c) receive subject data from the user via a communications network, the data including levels or concentrations of a lipid analyte selected from the list consisting of:
  (i) one or more modified lipid analytes listed in Table 1;
  (ii) two or more non-modified lipid analytes listed in Table 1, and
  (iii) two or more lipid analytes wherein at least one is a modified lipid analyte listed in Table 1 and at least one is a non-modified lipid analyte listed in Table 1;
  wherein the level or ratio of the lipid analyte or analytes relative to a control provides a correlation to the presence, state, classification or progression of heart disease;

(d) performing an algorithmic function including comparing the data to predetermined data;
(e) determining the status of the subject in accordance with the results of the algorithmic function including the comparison; and
(f) output an indication of the status of the subject to the user via the communications network.

The processing system can be adapted to receive data from a remote end station adapted to determine the data.

The processing system may include:
(a) a first processing system adapted to:
 (i) receive the data; and
 (ii) determine the status of the subject in accordance with the results of the multivariate analysis function including comparing the data; and
(b) a second processing system adapted to:
 (i) receive the data from the processing system;
 (ii) perform the multivariate or univariate analysis function including the comparison; and
 (iii) transfer the results to the first processing system.

The base station typically includes:
(a) a first firewall for coupling the first processing system to the communications network; and
(b) a second firewall for coupling the first and the second processing systems.

The processing system can be coupled to a database, the processing system being adapted to store the data in the database.

Still another aspect of the present invention contemplates the use of a panel of lipid analytes selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
in the manufacture of an assay to identify the presence, state, classification or progression of heart disease in a subject.

In another embodiment, the present invention contemplates an assay for determining the presence of heart disease in a subject, the assay comprising determining the concentration of a lipid analyte selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
wherein the level or ratio of the lipid analyte or analytes relative to a control provides a correlation to the presence, state, classification or progression of heart disease in a biological sample from the subject wherein an altered concentration in the lipid or lipids is indicative of the subject having heart disease.

In accordance with this embodiment, levels of the lipid(s) may be screened alone or in combination with other biomarkers or heart disease indicators. An "altered" level means an increase or elevation or a decrease or reduction in the concentrations of the lipids.

The determination of the concentrations or levels of the biomarkers enables establishment of a diagnostic rule based on the concentrations relative to controls. Alternatively, the diagnostic rule is based on the application of a statistical and machine learning algorithm. Such an algorithm uses relationships between biomarkers and disease status observed in training data (with known disease status) to infer relationships which are then used to predict the status of patients with unknown status. An algorithm is, employed which provides an index of probability that a patient has heart disease or a state or form or class thereof. The algorithm performs a multivariate analysis function.

Hence, the present invention provides a diagnostic rule based on the application of statistical and machine learning algorithms. Such an algorithm uses the relationships between lipidomic biomarkers and disease status observed in training data (with known disease status) to infer relationships which are then used to predict the status of patients with unknown status. Practitioners skilled in the art of data analysis recognize that many different forms of inferring relationships in the training data may be used without materially changing the present invention.

Hence, the present invention contemplates the use of a knowledge base of training data comprising levels of lipid biomarkers from a subject with a heart condition to generate an algorithm which, upon input of a second knowledge base of data comprising levels of the same biomarkers from a patient with an unknown heart disease condition, provides an index of probability that predicts the nature of the heart disease condition.

The term "training data" includes knowledge of levels of lipid biomarkers relative to a control. A "control" includes a comparison to levels of biomarkers in a subject devoid of the heart disease condition or cured of the condition or may be a statistically determined level based on trials. The term "levels" also encompasses ratios of levels of lipid biomarkers.

Hence, the "training data" includes levels or ratios of one or more of three groups of lipid analytes selected from
(i) modified ceramides (modCER), modified phosphatidylcholines (modPC) and modified cholesterol esters (modCE) selected from those listed in Table 1;
(ii) two or more non-modified lipid analytes selected from the list in Table 1; and/or
(iii) two or more lipid analytes wherein at least one is a modified lipid analyte listed in Table 1 (modCER, modPC and/or modCE) and at least one is a non-modified lipid analyte, selected from the list in Table 1.

The present invention further provides a panel of lipidomic biomarkers useful in the detection of a heart disease, the panel comprising lipid analytes selected from the list consisting of:
(i) one or more modified lipid analytes listed in Table 1;
(ii) two or more non-modified lipid analytes listed in Table 1, and
(iii) two or more lipid analytes wherein at least one is a modified lipid analyte listed in Table 1 and at least one is a non-modified lipid analyte listed in Table 1;
wherein the level or ratio of the lipid analyte or analytes, relative to a control provides a correlation to the presence, state, classification or progression of heart disease.

The lipid biomarkers contemplated herein include from one to 331 biomarkers such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330 or 331 biomarkers. The levels or concentrations of the biomarkers provide the input test data referred to herein as a "second knowledge base of data". The second knowledge base of data either is considered relative to a control or is fed into an algorithm generated by a "first knowledge base of data" which comprise information of the levels of biomarkers in a subject with a known heart disease condition. The second knowledge base of data is from a subject of unknown status with respect to a heart disease condition. The output of the algorithm or the comparison to a control is a probability or risk factor, referred to herein as "an index of probability", of a subject having a particular heart disease condition or not having the condition. This includes determining whether the subject has unstable (vulnerable patient) or stable (non-vulnerable patient) plaques:

Data generated from the levels of a lipid analyte selected from the list consisting of:
 (i) one or more modified lipid analytes listed in Table 1;
 (ii) two or more non-modified lipid analytes listed in Table 1, and
 (iii) two or more lipid analytes wherein at least one is a modified lipid analyte listed in Table 1 and at least one is a non-modified lipid analyte listed in Table 1;
are input data. The input of data comprising the lipid analytes is compared with a control or is put into the algorithm which provides a risk value of the likelihood that the subject has, for example, heart disease. A treatment regime can also be monitored as well as a likelihood of a relapse.

In context of the present disclosure, "fluid" includes any blood fraction, for example serum or plasma, that can be analyzed according to the methods described herein. By measuring blood levels of a particular lipid biomarker(s), it is meant that any appropriate blood fraction can be tested to determine blood levels and that data can be reported as a value present in that fraction. Other fluids contemplated herein include ascites, tissue exudate, urine, lymph fluid, mucus and respiratory fluid.

As described above, methods for diagnosing heart disease by determining levels of specific identified lipid biomarkers as listed in Table 1 and using these levels as second knowledge base data in an algorithm generated with first knowledge base data or levels of the same biomarkers in patents with a known disease. Also provided are methods of detecting symptomatic heart disease comprising determining the presence and/or velocity of specific identified lipid biomarkers in a subject's sample. By "velocity" it is meant the change in the concentration of the biomarker in a patient's sample over time.

The term "sample" as used herein means any sample containing lipid analytes that one wishes to detect including, but not limited to, biological fluids (including blood, plasma, serum, ascites), tissue extracts, freshly harvested cells, and lysates of cells which have been incubated in cell cultures. In a particular embodiment, the sample is heart tissue, one or more plaque, blood, serum, plasma or ascites.

As indicated above, the "subject" can be any mammal, generally human, suspected of having or having heart disease. The subject may be symptomatic or asymptomatic.

The term "control sample" includes any sample that can be used to establish a first knowledge base of data from subjects with a known disease status.

The method of the subject invention may be used in the diagnosis and staging of heart disease. The present invention may also be used to monitor the progression of a condition and to monitor whether a particular treatment is effective or not. In particular, the method can be used to confirm the absence or amelioration of the symptoms of the condition such as following surgery, stents, medication or behavioural change.

In an embodiment, the subject invention contemplates a method for monitoring the progression of heart disease in a patient, comprising:
 (a) providing a sample from a patient;
 (b) determining the level of a lipid analyte selected from the list consisting of:
  (i) one or more modified lipid analytes listed in Table 1;
  (ii) two or more non-modified lipid analytes listed in Table 1, and
  (iii) two or more lipid analytes wherein at least one is a modified lipid analyte listed in Table 1 and at least one is a non-modified lipid analyte listed in Table 1;
 wherein the level or ratio of the lipid analyte or analytes relative to a control provides a correlation to the presence, state, classification or progression of heart disease subjecting the levels to an algorithm to provide an index of probability of the patient having heart disease; and
 (c) repeating steps (a) and (b) at a later point in time and comparing the result of step (b) with the result of step (c) wherein a difference in the index of probability is indicative of the progression of the condition in the patient.

In particular, an increased index of probability of a disease condition at the later time point may indicate that the condition is progressing and that the treatment (if applicable) is not being effective. In contrast, a decreased index of probability at the later time point may indicate that the condition is regressing and that the treatment (if applicable) is effective.

The present invention further provides an algorithm-based screening assay to screen samples from patients. Generally, input data are collected based on levels of one or more lipid biomarkers and subjected to an algorithm to assess the statistical significance of any elevation or reduction in levels which information is then output data. Computer software and hardware for assessing input data are encompassed by the present invention.

Another aspect of the present invention contemplates a method of treating a patient with heart disease the method comprising subjecting the patient to a diagnostic assay to determine an index of probability of the patient having the heart condition, the assay comprising determining the levels of a lipid analyte selected from the list consisting of:
 (i) one or more modified lipid analytes listed in Table 1;
 (ii) two or more non-modified lipid analytes listed in Table 1, and
 (iii) two or more lipid analytes wherein at least one is a modified lipid analyte listed in Table 1 and at least one is a non-modified lipid analyte listed in Table 1;
wherein the level or ratio of the lipid analyte or analytes relative to a control provides a correlation to the presence, state, classification or progression of heart disease and where there is a risk of the patient having the condition, subjecting the patient to surgical intervention, medication and/or behavioural change and then monitoring index of probability over time.

Reference to an "algorithm" or "algorithmic functions" as outlined above includes the performance of a multivariate or univariate analysis function. A range of different architectures and platforms may be implemented in addition to those described above. It will be appreciated that any form of architecture suitable for implementing the present invention may be used. However, one beneficial technique is the use of distributed architectures. In particular, a number of end stations may be provided at respective geographical locations. This can increase the efficiency of the system by reducing data bandwidth costs and requirements, as well as ensuring that if one base station becomes congested or a fault occurs, other end stations could take over. This also allows load sharing or the like, to ensure access to the system is available at all times.

In this case, it would be necessary to ensure that the base station contains the same information and signature such that different end stations can be used.

It will also be appreciated that in one example, the end stations can be hand-held devices, such as PDAs, mobile phones, or the like, which are capable of transferring the subject data to the base station via a communications network such as the Internet, and receiving the reports.

In the above aspects, the term "data" means the levels or concentrations of the biomarkers. The "communications network" includes the internet. When a server is used, it is generally a client server or more particularly a simple object application protocol (SOAP).

A report outlining the likelihood of heart disease by the subject is issued.

The present invention is further described by the following non-limiting Examples. Materials and Methods used in these Examples are provided below.

Materials and Methods

Sample Collection

Plasma samples from the CAD patients used in this study were collected as part of a previous study conducted by White et al. *Cardiovascular Research* 75:813-20, 2007. A total of 202 patients with de novo presentation of CAD who were undergoing coronary angiography were recruited (White et al. supra 2007). Patients who had undergone previous coronary revascularization were excluded. Of the original 202 patients, plasma samples from 143 were available for use in this project. Patients were classified as either stable (n=61) or unstable (n=81) by two independent cardiologists on the basis of their symptoms, 12-lead ECG and cardiac troponin I measurements in accordance with the Braunwald criteria (White et al. supra 2007; Braunwald E. Circulation 80:410-4, 1989). Venous blood samples were collected into EDTA tubes. The plasma was prepared by centrifugation (1000×g, 15 minutes at 4° C.) and stored at −80° C. until required. Biochemical, lipid, and hematological parameters as well as clinical characteristics were measured. These included total cholesterol, LDL, high density lipoprotein (HDL), blood pressure, C reactive protein (CRP), smoking status, medications and body mass index (BMI).

Plasma samples from a cohort of 61 healthy individuals were obtained and used as control samples. Patients were not receiving medication for coronary vascular disease (CVD), diabetes or hypertension and had no history of myocardial infarction (MI). Additionally, patients displayed blood pressure <131/86 mm Hg, fasting total cholesterol <5.6 mmol/L, fasting triglycerides <2.0 mmol/L and fasting plasma glucose <6.1 mmol/L. Plasma was prepared by centrifugation (1500× g, 10 minutes at 4° C.) within 24 hours of collection. The plasma samples had not been thawed prior to this study.

Sample Preparation and Lipid Extraction

Plasma samples (200 µL) were thawed and treated with the antioxidant butylhydroxytoluene (BHT) (1 µL of 100 mM in ethanol) and immediately vortexed. Lipid extraction was performed using a modification of the method of Folch et al. *J Biol Chem* 226:497-509, 1957. A 10 µL aliquot of plasma was transferred to an eppendorf tube with 104 of internal standard mix 1 and 5 µL of internal standard mix 2 (Table 2). CHCl$_3$/MeOH (2:1) (200 µL) was added followed by brief vortexing. Samples were placed on a rotary mixer for ten minutes and then sonicated in a water bath at room temperature for thirty minutes. After sonication, the samples were incubated for twenty minutes at room temperature followed by centrifugation (16,000×g, 10 minutes at room temperature). The supernatant was transferred into a 0.5 mL polypropylene 96 well plate and dried under a stream of nitrogen at 40° C. The samples were resuspended in 50 µL water saturated butanol followed by ten minutes sonication. Then 50 µL of 10 mM ammonium formate in methanol was added. The samples were centrifuged (3,350×g, 5 minutes at room temperature) and the supernatant transferred into 0.2 mL micro-inserts placed into 32×11.6 mm glass vials with Teflon insert caps. Once extracted the samples were immediately subjected to mass spectrometry.

Mass Spectrometry

Lipid analysis was performed by liquid chromatography, electrospray ionisation-tandem mass spectrometry (LC ESI-MS/MS) using a HP 1200 liquid chromatography system combined with a PE Sciex API 4000 Q/TRAP mass spectrometer with a turbo-ionspray source (350° C.) and Analyst 1.5 data system. A Zorbax C18, 1.8 µm, 50×2.1 mm column was used for LC separation. The mobile phase consisted of tetrahydrofuran:methanol:water in the ratios 30:20:50 (Solvent A) and 75:20:5 (Solvent B), both containing 10 mM NH4COOH. The following gradient conditions were employed for all lipids except the DG and TG; 100% A/0% B reducing to 0% A/100% B over eight minutes followed by 2 minutes at 0% A/100% B, a return to 100% A/0% B over 0.5 minute then held for 3.5 minutes at 100% A/0% B prior to the next injection. DG and TG were separated using the same system with an isocratic flow at 15% A/85% B for 6 minutes between injections.

The optimisation of voltages for collision energy (CE), declustering potential (DP), entrance potential (EP) and cell exit potential (CXP) was carried out using the tuning and optimisation feature of the instrument software (Analyst 1.5).

Nomenclature

The nomenclature (both systematic and common names) used in this document has come primarily from the two recent publications on this topic from the Lipid Maps Consortium (See Fahy et al., *J Lipid Res*. 51(6): 1618, 2010 and Fahy et al., *J Lipid Res*. 50: S9-14, 2009).

In addition, a number of terms have been used to define lipid species where the full structure is not known but where characteristic collision induced fragmentation data has provided us with a partial structure of the lipid species. These are as follows modPC xxx.x/yy.y=modified or undefined phosphocholine containing lipid species with mass/charge ratio of the M+H ion denoted by xxx.x and retention time under the presently disclosed defined chromatographic conditions defined as yy.y minutes.

modCer xxx.x/yy.y=modified or undefined sphingosine containing lipid species with mass/charge ratio of the M+H ion denoted by xxx.x and retention time under the presently disclosed defined chromatographic conditions defined as yy.y minutes.

modCE xxx.x/yy.y=modified or undefined cholesterol containing lipid species with mass/charge ratio of the M+H ion denoted by xxx.x and retention time under the presently disclosed defined chromatographic conditions defined as yy.y minutes.

Modified PC species initially referred to as modPC 552.4/3.90, modP C 580.4/4.84, modPC 508.3/3.30, modPC 510.3/4.00, modPC 564.4/4.70, modPC 566.4/5.10, modPC752.5/5.7, modPC692.4/5.8, modPC678.4/5.4, modPC622.4/4.0, modPC878.6/7.1, modPC881.6/6.1 and modPC818.6/6.6, have been reclassified as LPC 20:0, LPC 22:0, LPAF 18:1, LPAF 18:0, LPAF 22:1, LPAF 22:0, PC34:5, APC 30:0, PC 28:0, PC 24:0, modPC877.6/7.1, modPC879.6/6.1 and APC 40:7, respectively. A small number of modPC species have been removed from Table 1, namely modPC 590.4/4.80, modPC 592.4/5.10, modPC 608.4/5.33, modPC 745.5/6.35, modPC 764.5/6.52 and modPC 769.5/6.25.

Identification of Potential Biomarkers:

1-O-acylceramides, oxidized phosphatidylcholine (OxPC) and oxidized cholesterol esters (OxCE) were thought to be potential biomarkers of the presence and progression of CAD. To identify lipid species in each of these classes, precursor ion scans were performed on a subset of 30 individuals (10 healthy controls, 10 stable CAD and 10 unstable CAD) chosen at random from our cohort.

Identification of Modified Ceramides:

Precursor scans were performed to identify 1-O-acylceramide species in plasma. Fragmentation of ceramides by CID in Q2 cleaves the bond between the carbon and the nitrogen at the sphingoid base and, with the loss of water, produces a daughter ion with a m/z 264.3 (Murphy et al. *Chem Rev* 101:479-526, 2001). Thus a precursor ion scan for m/z 264 will identify all modified ceramides including 1-O-acylceramides. These are referred to collectively as modified ceramides (modCer). Two precursor ion scans for m/z 264.3 were performed to cover the m/z ranges 530-760 for low molecular weight modCer and m/z 750-980 for high molecular weight modCer (Table 3).

Identification of Modified Phosphatidylcholines:

OxPC species may include non-truncated OxPCs which involve the addition of oxygen at the double bonds of the polyunsaturated acyl moieties (Davis et al. *J Biol Chem* 283:6428-37, 2008) or truncated oxPCs where the oxidized acyl chains are cleaved to produce lower molecular weight species. A precursor ion scan for m/z 184 will identify all species of lipids containing a phosphocholine head group including oxidized phosphatidylcholines. However other phosphocholine species may also be identified, we have referred to these species as modified PC (modPC). To cover the possible m/z ranges that would cover all OxPCs, three precursor ion scan experiments were performed. The m/z ranges for Q1 for these three experiments were 490-670, 640-820 and 800-980. Fragmentation of phospholipids by CID of PC species produces a daughter ion of 184.1 which was used as the m/z setting in Q3 (Davis et al. supra 2008, Cui and Thomas *Journal of Chromatography B;* 877:2709-15, 2009) (Table 3).

Identification of Oxidized Cholesterol Esters:

As with phosphatidylcholine species, cholesterol esters which contain polyunsaturated fatty acids are susceptible to oxidation. A precursor ion scan of m/z 369 will identify all species of cholesterol ester, those with oxidized fatty acids. These are referred to as modified cholesterol esters (modCE). The mass ranges for the two precursor ion scan experiments aimed at identifying modCEs were m/z 450-650 and m/z 650-850 in Q1 with a m/z setting of 369.3 for Q3 (Table 3).

Plasma Lipid Profiling:

MRM experiments were established for each of the new lipid biomarkers identified from the precursor ion scans. These were then combined with a larger set of MRM experiments that had been developed by identifying the major species of each lipid class in plasma extracts using precursor ion and neutral loss scans (Table 4 and as updated in Table 15).

Plasma lipid profiling using these MRM experiments was performed on each of the 202 plasma samples in the cohort in addition to 14 quality control (QC) plasma samples. Each ion pair was monitored for between 10 and 50 ms (using scheduled MRM mode) with a resolution of 0.7 amu at half-peak height and the area under the resulting chromatogram was calculated. The peak area data was analysed using Applied Biosystems Analyst 1.5. Raw data for each class was normalised against the internal standard and converted into pmol per mL of plasma.

Statistical Analysis

Data Processing and Statistical Analysis of Precursor Ion Scan Data:

Data resulting from the precursor ion scans were analysed using Markerview (version 1.2). Data were normalized against the respective internal standard of the lipid class under investigation.

A Student's t-test was performed to identify which lipid analytes were significantly different between stable and unstable CAD groups and between control and CAD groups (stable and unstable CAD combined). Analytes with a p value <0.1 that did not correspond to known lipid species were then incorporated into the plasma profiling methods, these lipid species were termed modCer, modPC and modCE.

Data Processing and Statistical Analysis of MRM Data:

Non-parametric, Mann-Whitney-U tests were used to determine the analytes that were significantly different between stable vs unstable CAD groups and the control vs CAD groups. Analysis of variance (ANOVA) was performed on linear regression models to determine the relative contribution of the traditional risk factors and lipid analytes to classification models (SPSS version 17.0, SPSS Inc).

Multivariate analysis was applied for the creation of prediction models. This analysis followed a statistical machine learning approach and methodology comprising multiple cross-validation iterations to assess the power of proposed solutions (National ICT Australia). Briefly, recursive feature elimination (RFE) analysis with three-fold cross-validation repeated multiple times (100) was applied to develop multivariate models using support vector machine learning. This was done for models of varying feature size (e.g., 2, 4, 8, 16, 32 and 64). The output of this exercise was a ranked list of the lipids according to the frequency of their recurrent incorporation in generated models. This approach also allowed the removal of those highly correlated variables that did not add significantly to the model. For each set of models with different numbers of analytes Receiver Operator Characteristic (ROC) analysis was performed, calculating Area Under the Curve (AROC).

ROC analysis is used extensively in diagnostic testing to determine the performance of a given model (Fawcett T *Pattern Recogn Lett* 27:861-74, 2006).

EXAMPLE 1

Patient Characteristics

The patients in the stable and unstable cohorts were closely matched, with the exception of smoking status and hsCRP (Table 5). In contrast, most of the clinical and biochemical parameters differed significantly between the control cohort and the CAD cohort (combined stable and unstable CAD patients) (Table 5).

The medication profile of the stable and unstable CAD patients was examined for lipid lowering, antihypertensive, antiplatelet, anticoagulant, anti-anginal anti-arrhythmic and anti-diabetic treatments. $X^2$ revealed that four medications were significantly different between these two cohorts (Table 6). The medications that showed differences were statins for the lipid lowering medications, angiotensin II blockers and intravenous glycerol nitrate from the anti-hypertensive medications and heparin infusion from the anticoagulant medications.

EXAMPLE 2

Identification of Biomarkers

Precursor ion scans were used to identify modCer, modPC and modCE biomarkers using Markerview software (version 1.2).

This software aligns and then tabulates the m/z and retention time for all the peaks (also called features) within the precursor ions scans. It then normalizes the data against the relevant internal standard. A student t-test was then applied to the features to identify which were different between stable and unstable CAD cohorts and between the control and CAD cohorts, at a significance of $p<0.10$. The spectra of these peaks were then examined to remove known lipid species and isotopes.

From this process a total of 75 markers (14 modCer, 57 modPC and 4 modCE) were selected across the three lipid classes, these markers are shown in Table 7.

EXAMPLE 3

Plasma Lipid Profiling of Control, Stable Cad and Unstable CAD Cohorts

Each of the 202 plasma samples in the cohort was analyzed for a total of 331 lipid species by the two scheduled MRM experiments (Tables 7 and 8). From the lipid concentrations in the 14 QC samples the coefficients of variation (% CV) were determined across the entire analytical run. % CV values were less than 20% for 271 of the 331 lipid species. Those lipids which had a % CV greater that 20% were primarily lipid species that were in low abundance (<200 pmol/mL) these did not include the top ranking lipid analytes.

EXAMPLE 4

Univariate Analysis

A Mann Whitney-U test was used to distinguish which lipids showed significant differences between cohorts (stable CAD vs unstable CAD and control vs CAD). This identified 73 lipids that were significantly different between the stable and unstable CAD cohorts ($p<0.05$) and 198 lipids that showed statistical significance ($p<0.05$) between the control and CAD cohorts and (Table 9). A summary of the total number of lipids per lipid class that show differences between these cohorts is shown in Table 10.

Anova

In order to identify lipids that were independent predictors of class assignment linear regression analysis was performed. A number of different models were created to analyse different subsets of the cohort for covariates.

Models 1 to 3 were created with the stable CAD and unstable CAD cohorts. Model one used only the 13 traditional risk factors (age, sex, smoking status, diabetes, hypertension, family history of CAD, BMI, total cholesterol, LDL, HDL, triglycerides, glucose and hsCRP, Table 5). Model 2 was created using only the lipids (see Table 9 and 10) and Model 3 included both the lipids as well as the traditional risk factors. The ANOVA results and covariates that were independent predictors and showed significance ($p<0.05$) are shown in Table 11. The partial correlation values show the relative contribution of the independent variables to the model when the linear effects of the other independent variables in the models have been removed. From the R2 values (measure of the fit of the model) it can be seen that model 3 ($R^2=0.473$) shows the best fit indicating that the combination of the lipid biomarkers and the traditional risk factors provides a better classification of the stable and unstable CAD cohorts than the traditional risk factors or the lipids alone. Whilst CRP is the most significant sources of variation between these two cohorts, the lipids PI 34:0. DHC 18:1, modCer 703.6/5.87, SM 22:1 and GM3 18:0 were also shown to be independent predictors.

Models 4, 5 & 6 represent models created with the control and CAD cohorts using traditional risk factors alone, lipids alone or a combination of both respectively. The fit of these models (R2 values shown in Table 12) parallel that of the stable versus unstable CAD models with the data showing an improvement in the fit to the predictive model when traditional risk factors and lipids were combined. Twenty-one lipids were identified as being able to distinguish between control and CAD patients independently of all other factors (Table 12, model 6).

EXAMPLE 5

Multivariate Analysis

Linear regression modeling was able to create models that examined the influence of traditional risk factors, lipids and a combination of these in classifying between stable and unstable CAD patients, and control and CAD patients. However, given the complexity of the data set and the large number of variables, multivariate modeling is more appropriate to create a predictive model based upon the plasma lipid profile (Bylesjö et al. *Journal of Chemometrics* 20:341-51, 2006).

Recursive feature elimination (RFE) analysis was applied using three-fold cross validation (repeated 100 times) to develop multivariate models using support vector machine learning. This was done for models of varying feature size (e.g., 1, 2, 4, 8, 16, 32 and 64) and for models that included either lipids alone or lipids with traditional risk factors. The output of this exercise was a ranked list of the lipids according to the frequency of their recurrent incorporation in the generated models to distinguish stable CAD from unstable CAD (Table 13) or control from CAD (Table 14). This approach also allowed the removal of those significant but highly correlated variables that did not add significantly to the model.

The Y predictor values from these models were used to perform Receiver Operator Characteristic (ROC) analysis, which measures the sensitivity and specificity of the model and can be used as a measure of the model's ability to correctly classify cases (Stenlund et al. *Analytical Chemistry* 80:6898-906, 2008). The area under the curve (AUC) from these ROC analyses was potted against the number of variables to identify the minimum number required for optimal discrimination (FIGS. 1(A) and (B) and 2(A) and (B)). In the models created to discriminate between stable CAD and unstable CAD increasing the number of lipids in the model increased the AUC which reached a maximum at 8-16 lipid analytes (FIG. 1 panel A). Using a combination of traditional risk factors and lipids gave the best discrimination with a maximum AUC achieved with 8 features. FIG. 2, panel B shows that lipid only models had a lower error rate that the traditional risk factor only models but that the combined traditional risk factor and lipid models had the lowest error rates.

Models created to distinguish control and CAD had higher AUC and continued to show a slight increase up to 256 lipids although 16 lipids was sufficient to produce an AUC of 0.94 (FIG. 2 panel A). Similar to the stable CAD vs unstable CAD models, the combination of traditional risk factors and lipids resulted in the highest AUC with 16 features showing an AUC of 0.96. The combination of traditional risk factors and lipids also resulted in the lowest error rates in the control vs CAD models (FIG. 2, panel B).

The two models created with the 8 and 16 lipids (stable CAD vs unstable CAD and control vs CAD) were compared to the models created with the traditional risk factors and then to models created with a combination of the traditional risk factors and the lipids. These traditional risk factors included age, sex, smoking status, diabetes, hypertension, family history of CAD, BMI, total cholesterol, LDL, HDL, triglycerides, glucose and hsCRP. Whilst CRP is not classified as a traditional risk factor it was included in these models because CRP is a marker of inflammation and has also been used in other risk prediction scores such as the Reynolds Risk Score (Ridker et al. Circulation 109:IV-6-19, 2004; Ridker et al. *JAMA: Journal of the American Medical Association* 297: 611-9, 2007; Shearer et al. *PLoS ONE* 4:e5444, 2009).

Figure 4:
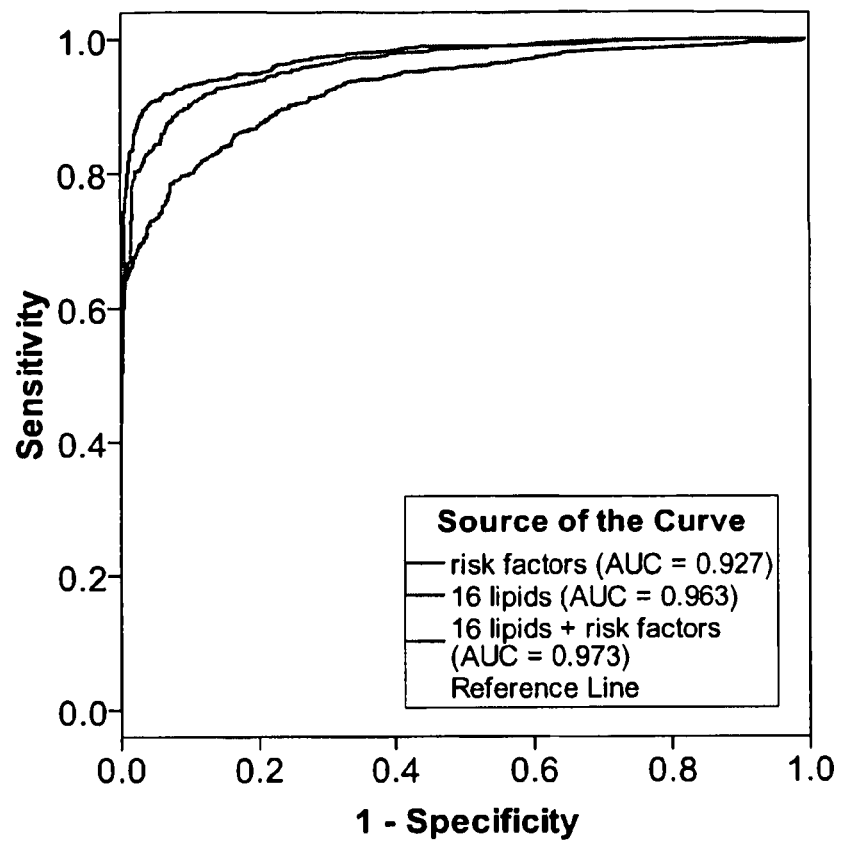
FIG. 4 is a graphical representation of ROC analysis of classification models of control vs CAD. Multivariate models created with either the 13 traditional risk factors (Table 5), the 16 highest ranked lipids (Table 14) or a combination of both were validated by three-fold cross validation repeated 10 times and the results combined in a ROC analyses.

Models were validated by three-fold cross validation repeated 10 times and the results combined in a ROC analyses. In the stable CAD vs unstable CAD models, traditional risk factors alone gave an AUC of 0.723 compared with 0.748 for 8 lipids, while the 13 traditional risk factors combined with the 8 lipids resulted in an AUC of 0.765 (FIG. 3). In the control vs CAD models, traditional risk factors alone gave an AUC of 0.927 compared with 0.963 for 16 lipids, while the 13 traditional risk factors combined with the 16 lipids resulted in an AUC of 0.973 (FIG. 4).

Discussion

There are no current screening methods that can prospectively identify unstable plaque. As proposed herein, plasma lipids are suitable biomarkers to identify plaque instability and patient vulnerability. ModCer, modPC and modCE lipid species were identified as useful biomarkers that can distinguish between stable and unstable CAD. These markers as well as previously characterised lipids enabled the creation of a plasma lipid profile that reflected the changes in lipid metabolism associated with the progression of CAD. In combination with the traditional risk factors, the plasma lipid profiles improved the ability to stratify CAD patients into stable and unstable cohorts, and may serve as a cost effective, non-invasive clinical screening method to identify non-symptomatic patients at risk (Damas and Aukrust *Scand Cardiovasc J* 40:262-6, 2006; Naghavi et al. *Circulation* 108:1772-8, 2003).

Identification of New Biomarkers for CAD:

Whilst the exact changes that occur in lipid metabolism during the progression of CAD are not fully understood, there is growing evidence to suggest that the lipid peroxidation products play a role in atherogenesis (Davis et al. supra 2008; Oei et al. Circulation 111:570-5, 2005). Precursor ion scanning allowed the identification of modPCs and modCer based upon their characteristic fragmentation. The plasma concentrations of these lipids were significantly different between the stable and unstable CAD cohorts as well as the control and CAD cohorts. This supports the concept that ModPCs and modCers are involved in the changes that occur in lipid metabolism with the progression of the disease. Whilst precursor ion scanning enabled the determination of the parent ion m/z for these lipids, it is not able to provide information regarding their exact structure. By identifying the species of interest (i.e. those that show a significant difference between cohorts), this provides an efficient means of targeting specific lipids to be further characterised by either further mass spectrometric analysis or other structural methods such as nuclear magnetic resonance spectroscopy. This information may further unravel the mechanism behind the changes in lipid metabolism driving plaque progression and instability.

EXAMPLE 6

Updated Results

Updated Patient Characteristics

The patients in the stable and unstable cohorts did not differ in conventional risk factors, with the exception of smoking status, and hsCRP (Table 1). In contrast, most clinical and biochemical parameters differed significantly between the control cohort and the CAD cohort (combined stable and unstable CAD patients) (Table 1). This selection of the control group was made to optimise the ability to identify differentiating lipid species. Medication use was similar between the stable and unstable groups with the exception of statin and antigoagulant use (Table 2).

Identification of New Biomarkers and Plasma Lipid Profiling

Analysis of the plasma lipid extracts from 10 control, 10 stable and 10 unstable CAD patients by precursor ion scanning identified 38 species of modPC, 13 species of modCer and 4 species of modCE that displayed a significant difference between control and CAD groups. These were combined with the other lipid species identified in plasma to define the plasma lipid profile (Table 1, Table 7 and Table 8).

Plasma samples were analysed for 329 lipid species by two scheduled MRM experiments. Quality control plasma samples (QC; 14 replicates) were evenly spaced within the cohort. The coefficients of variation (CV) within the QC samples were less than 20% for 271 of the 329 lipid species. Those lipids which had a CV greater that 20% were primarily lipid species that were in low abundance (<200 pmol/mL); none of these were included in the top ranked lipid analytes used in the multivariate models.

Binary logistic regression analysis, adjusting for age and sex identified 30 lipids that were significantly different (p<0.01) between the stable CAD and unstable CAD groups and 95 lipids that were different (p<0.01) between the control and CAD (stable and unstable combined) groups (Table 16).

Multivariate Analysis

Binary logistic regression models (3-fold cross validation repeated 100 times) were created to assess the relative contribution of lipids and risk factors to the differentiation of stable CAD from unstable CAD and control from CAD. Models (stable CAD vs unstable CAD) using lipids only, traditional risk factors only or a combination of both produced C-statistics of 0.739 (CI 0.734-0.745), 0.679 (CI 0.673-0.685) and 0.804 (CI 0.798-0.811) and % accuracy of 69.5, 64.5 and 73.3 respectively (Table 17A). The multiple cross validation enabled us to rank the lipids and traditional risk-factors based on their recurrent incorporation in the logistic models. The ranked lists for the lipid only and risk factor only models are shown in Tables 18 and 19. Table 20 shows the ranked list for the combined lipids and traditional risk factor models. Models of control vs CAD using lipids only, traditional risk factors only or a combination of both produced C-statistics of 0.946 (CI 0.944-0.948), 0.956 (CI 964-0.958 and 0.982 CI 0.981-0.983 and % accuracy of 87.4, 90.3 and 92.3 respectively (Table 17B). The ranked features for the separate lipid and risk factor models are shown in Supplementary Tables 21 and 22. The ranked features for the combined lipids and risk factors model are shown in Table 23.

Figure 6:
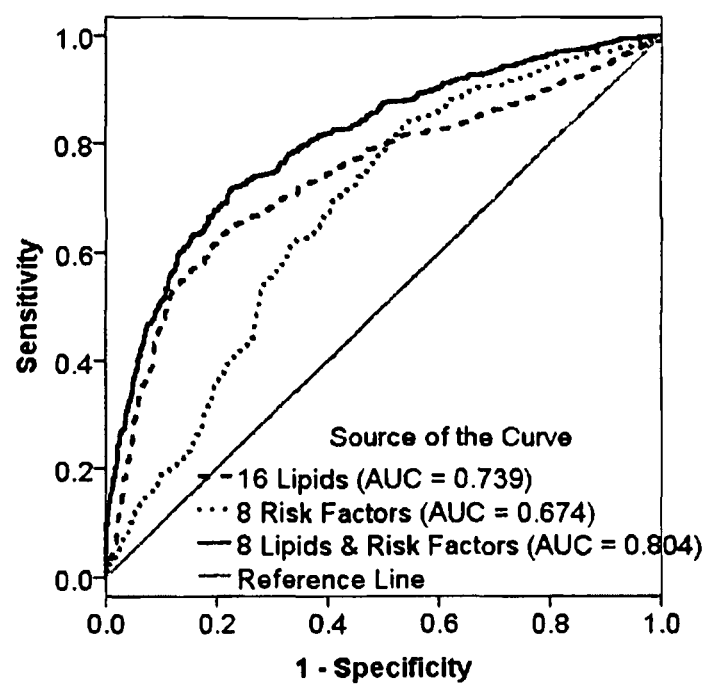
FIG. 6 provides a graphical representation of data showing receiver operator characteristic (ROC) analysis of multivariate models. Multivariate classification models were created by recursive feature elimination with three-fold cross-validation (repeated 100 times) using support vector machine learning. ROC analysis was performed on the optimised models containing either 16 lipids alone, 8 risk factors alone or a combination of 8 lipids and risk factors.

Recursive feature elimination (RFE) analysis was also applied using three-fold cross validation (repeated 100 times) to develop multivariate models using support vector machine learning. Models of varying feature size (e.g., 1, 2, 4, 8, 16 . . . , 329) that included either lipids alone, risk factors alone or lipids with risk factors were developed. The ranked list of the lipids/risk factors according to the frequency of their recurrent incorporation in the generated models is shown in Tables 24 and 25. The C-statistic and % accuracy from each model was plotted against the number of variables to assess the performance of the different models and identify the minimum number required for optimal discrimination (FIG. 5). Models using lipids alone (FIG. 5A circles) to discriminate stable CAD from unstable CAD showed a maximum C-statistic (0.739, CI 0.734-0.745) with only 16 lipids in the model. This was significantly better than the model created with risk factors alone (FIG. 5A squares) (C-statistic of 0.679, CI 0.673-0.685), while the model containing a combination of lipids and risk factors performed best (C-statistic of 0.804 (CI 0.798-0.811)) with only eight features (FIG. 6). This model also had the highest accuracy of 73.3% compared to risk factors alone (FIG. 5A triablges and FIG. 6) (64.5%) or lipids alone (69.5%) (FIG. 5B).

Classification of CAD from control using lipids only gave a C-statistic of 0.939 (CI 0.937-0.945) with 128 lipids in the model, however, only 16 lipids were sufficient to give a C-statistic of 0.919 (See FIG. 5C) (CI 0.917-0.921). While the traditional risk factors performed slightly better than lipids with a C-statistic of 0.965 (CI 0.964-0.966), the combined lipids and risk factor model performed best with a C-statistic of 0.973 (CI 0.972-0.974) with 16 features. This model also had the highest accuracy of 85.3% compared to risk factors (83.2%) or lipids (80.2%) (FIG. 5D). The high level of discrimination of control from CAD with all models reflects the CAD status of the control group specifically chosen to highlight differences in the lipid profile between these groups.

Updated Discussion

This study has identified differences in the plasma lipidome between stable CAD and unstable CAD. Multivariate models combining traditional risk factors and plasma lipids gave a significant improvement over traditional risk factors alone such that over 73% of patients could be correctly classified as either stable or unstable CAD. These findings indicate that plasma lipid profiling has significant diagnostic and prognostic potential for the identification of individuals at risk for unstable coronary syndromes.

The healthy control group was selected to provide the greatest phenotypic difference with the CAD groups and thereby optimise the ability to identify new lipid markers associated with CAD. Subsequent analyses of these new lipid markers and 276 known lipid species in the stable and unstable CAD groups identified 30 of these lipid species as potential biomarkers of unstable CAD. The single most prominent difference between stable and unstable CAD was the concentration of PI species. Total PI was 13.8% lower in the unstable CAD group relative to the stable CAD group with 9 of the 17 species showing a significantly lower level (p<0.01) and a further five species showing a negative trend. This is in addition to a 13.5% decrease in the stable CAD group relative to the control group, demonstrating an association between PI species and disease severity. The relevance of these observations may lie in the fact that PI, via the action of PLA2, is the primary source of arachidonic acid which is required for the biosynthesis of the prostaglandins and other ecosanoids that are involved in the activation of monocytes and macrophages and associated with matrix metalloproteinase production, a hallmark of plaque instability. PLA2 has been detected in atherosclerotic lesions, both co-localised with macrophages and in the extracellular matrix where it is thought to act on LDL to release arachidonic acid.

In contrast to PI, PS which also showed a decrease in stable CAD relative the control group (−36.1%, p=3.03E-04) displayed a higher level in the unstable CAD relative to the stable CAD group (23.9%, non-significant). PS is released from activated platelets in membrane vesicles and enhances the activation of prothrombin to thrombin during blood coagulation and thrombogenesis. However, PS is also a substrate for a number of phospholipases which may account for the lower levels in the stable CAD group relative to the control group.

In addition to differences between stable CAD and unstable CAD, many lipids showed a significant difference between the control and CAD groups. Alkylphosphatidylcholine (APC) species were almost uniformly lower in the CAD cohort with 9 of 17 species significantly different at the p<0.01 level and all but one species showing a negative trend. This may relate to the higher oxidative stress in the CAD group and the action of ROS on the polyunsaturated fatty acids of the APC species or directly on the vinyl ether linkages of the plasmalogens, which are also included in this lipid class. Alternatively, lower APC may be the result of increased PLA2 activity in these patients. The primary source of PLA2 activity in circulation is the lipoprotein PLA2 (Lp-PLA2), also known as the platelet activating factor acetylhydrolase which has been associated with increased risk of cardiovascular disease in numerous epidemiological studies.

However, while the action of ROS and PLA2 on these lipids would be expected to lead to the generation of LPC, which has previously been positively associated with inflammation and atherosclerosis, as described herein, lower levels of all LPC species with the exception of LPC 20:4 and LPC 20:3 which were significantly higher in the CAD group. The lower levels may result from an increase in the catabolism of these species were observed here, but more likely relates to their more efficient removal from circulation into tissues, either in the form of modified low-density lipoprotein or directly from albumin, which represents the major form of plasma LPC.

Figure 7:
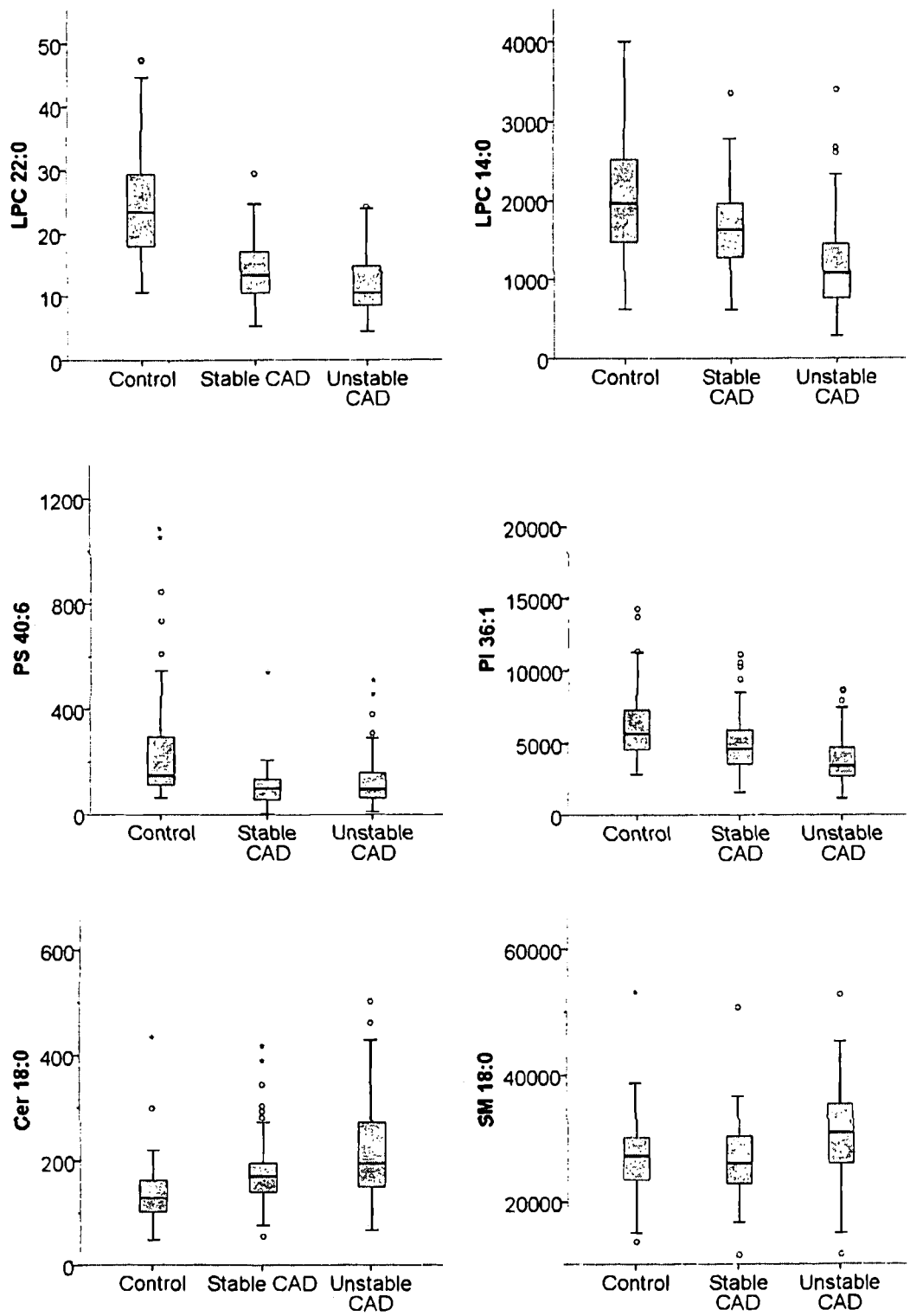
FIG. 7 provides graphical representations of data showing plasma levels of selected lipid species. Lipid species were measured in each group as described in Materials and Methods. The concentration of each lipid species expressed as pmol/mL is plotted for each group. The bar represents the median value, the box represents the $25^{th}$ to $75^{th}$ percentile and the whiskers the upper and lower limits. Circles show outliers (>1.5× height of the box from the median) and asterisks show extreme outliers (>3.0× height of the box from the median).

Some of these lipids (APC 34:2, LPC 16:1, LPC14:0) displayed a further decrease in the unstable CAD relative to the stable CAD again demonstrating an association with disease severity. LPC 14:0 had median levels of 2038, 1619 and 1192 pmol/mL in control, stable and unstable CAD groups respectively (FIG. 7). However, other lipids were altered specifically in the unstable CAD group relative to the combined control and stable CAD groups; SM 18:0 showed no difference between control and CAD but was significantly higher in the unstable CAD group relative to the stable CAD group (p=3.37E-3) (FIG. 7).

Differences of this type may reflect specific alterations in lipid metabolism associated with unstable disease.

Whilst the exact changes that occur in lipid metabolism during the progression of CAD are not fully understood, there is growing evidence to suggest that lipid peroxidation products play a role in atherogenesis. Precursor ion scanning allowed the identification of modified forms of PC (modPC) that have previously been reported as oxidised and truncated species (Davis et al., *J. Biol. Chem.* 283: 6428-6437, 2008; Oei et al., *Circulation.* 111: 570-575, 2005). These were also decreased in the CAD groups relative to the control group and some species showed a further decrease in unstable CAD relative to stable CAD. This may also be a reflection of increased PLA2 activity and tissue uptake as oxidised PC species are reported to be preferred substrates for LpPLA2 (Davis et al., 2008 (supra)) and high affinity ligands for scavenger receptors. Modified Cer species (modCer) were also identified as potential biomarkers and may relate to the formation of acylceramide species associated with lysosomal PLA2 activity involved in turnover of oxLDL.

Despite the incomplete knowledge of the lipid metabolism associated with CAD lipid biomarkers are described herein as useful for the development of multivariate models to effectively stratify individuals based on disease status. The inventors' strategy was to incorporate lipid classes that reflect the multiple biological functions and processes that underlie the progression of CAD, then apply recursive feature elimination with multiple cross validation to create optimal classification models with the minimum number of lipids. This process demonstrated that only 8-16 lipids were required to achieve almost maximum discrimination of disease status (FIGS. 5A and C). These lipids (Tables 24 and 25) showed a strong homology with the top ranked lipids identified by the logistic regression (Tables 20 and 23) as those most often incorporated into the multivariate models, thereby supporting the RFE selection process.

The influence of statins on the plasma lipid profile was examined in the stable CAD cohort; 9 of 229 lipids showed a correlation with statin use (15-76% difference in concentration, $p<0.01$) with a further 19 having $0.01>p<0.05$. However, only three of these 28 were identified as discriminating stable CAD from unstable CAD and only six lipid species were identified in the 95 that were statistically different between the control and CAD groups (Table 26). Two of these (PC 37:4 and PS 38:4) showed an opposite trend with statin use, to that observed in the CAD group, suggesting that statin use may partially correct these lipid levels.

Notwithstanding the limitations of a cross sectional study to develop predictive models, many of the lipids identified as discriminatory for unstable CAD displayed an association with disease severity suggesting that they are altered prior to the onset of ACS. The application of recursive feature elimination (RFE) using support vector machine learning enabled the development and cross validation of multivariate models for the classification of CAD patients as stable or unstable. The combination of only eight traditional risk factors and plasma lipids provided the best discrimination with a C-statistic of 0.804 (CI, 0.798-0.811) a significant improvement on the traditional risk factors alone which produced a C-statistic of only 0.679 (CI, 0.673-0.685) (FIG. 6).

The Examples demonstrate the potential of plasma lipid profiling for the identification of stable and unstable CAD.

Many modifications will be apparent to those skilled in the art without departing from the scope of the present invention.

TABLE 2

Internal standard mix composition and concentration[a]

| # | Lipid species | Internal standard | Concentration (pmol/15 µL) |
|---|---|---|---|
| 1 | bis(monoacylglycero)phosphate (BMP) | BMP 14:0/14:0 | 100 |
| 2 | ceramide (Cer) | Cer17:0 | 100 |
| 3 | monohexosylceramide (MHC) | MHC 16:0 d3 | 50 |
| 4 | dihexosylceramide (DHC) | DHC 16:0 d3 | 50 |
| 5 | trihexosylceramide (THC) | THC 17:0 | 50 |
| 6 | 1-O-acylceramide (acCer) | acCer 17:0 18:1 | 100 |
| 7 | sphingomyelin (SM) | SM 12:0 | 200 |
| 8 | phosphatidylglycerol (PG) | PG 17:0 17:0 | 100 |
| 9 | phosphatidylcholine (PC) | PC 13:0 13:0 | 100 |
| 10 | phosphatidylcholine (PC) | PC 21:0 21:0 | 100 |
| 11 | phosphatidylethanolamine (PE) | PE 17:0 17:0 | 100 |
| 12 | phosphatidylserine (PS) | PS 17:0 17:0 | 100 |
| 13 | lysophosphatidylcholine (LPC) | LPC 13:0 | 100 |
| 14 | diacylglycerol (DG) | DG 15:0 15:0 | 200 |
| 15 | triacylglycerol (TG) | TG 17:0 17:0 17:0 | 100 |
| 16 | cholesterol (COH) | COH d7 | 1000 |
| 17 | cholesterol ester (CE) | CE 18:0 d6 | 1000 |

[a]prepared in CHCL3/MeOH (1:1), 15 µL used in each plasma sample

TABLE 3

Mass spectrometer settings used for precursor ion scans

| Species | Q1 m/z range | Q3 m/z setting | DP[a] | EP[b] | CE[c] | CXP[d] |
|---|---|---|---|---|---|---|
| modified ceramide | 530-760 | 264.3 | 70 | 10 | 35-50 | 12 |
|  | 750-980 | 264.3 | 70 | 10 | 50-65 | 12 |
| modified phosphatidylcholine | 490-670 | 184.1 | 100 | 10 | 45 | 12 |
|  | 640-820 | 184.1 | 100 | 10 | 45 | 12 |
|  | 800-900 | 184.1 | 100 | 10 | 45 | 12 |
| modified cholesterol ester | 450-650 | 369.3 | 55 | 10 | 20 | 12 |
|  | 650-850 | 369.3 | 55 | 10 | 20 | 12 |

[a]DP, declustering potential
[b]EP, entrance potential
[c]CE, collision energy
[d]CXP, cell exit potential

TABLE 4

Scan methods used to create MRM acquisition methods for plasma lipid profiling

| Lipid class | No. of species | Internal standard | Parent ion | MRM type | DP | EP | CE | CXP |
|---|---|---|---|---|---|---|---|---|
| ceramide (Cer) | 7 | Cer 17:0 | $[M + H]^+$ | PIS[a], 264.3 m/z | 50 | 10 | 35 | 12 |
| monohexosylceramide (MHC) | 7 | MHC 16:0 d3 | $[M + H]^+$ | PIS, 264.3 m/z | 77 | 10 | 50 | 12 |
| dihexosylceramide (DHC) | 7 | DHC 16:0 d3 | $[M + H]^+$ | PIS, 264.3 m/z | 100 | 10 | 65 | 12 |
| trihexosylcermide (THC) | 7 | THC 17:0 | $[M + H]^+$ | PIS, 264.3 m/z | 130 | 10 | 73 | 12 |
| $G_{M3}$ ganglioside (GM3) | 6 | THC 17:0 | $[M + H]^+$ | PIS, 264.3 m/z | 155 | 10 | 105 | 16 |
| modified ceramide (modCer) | 14 | acCer 17:0 | $[M + H]^+$ | PIS, 264.3 m/z | 70 | 10 | 50 | 16 |
| sphingomyelin (SM) | 12 | SM 12:0 | $[M + H]^+$ | PIS, 184.1 m/z | 65 | 10 | 35 | 12 |
| phosphatidylglycerol (PG) | 4 | PG 17:0 17:0 | $[M^+ NH_4]^+$ | NL[b], 189 Da | 60 | 10 | 25 | 12 |
| bis(monoacylglycerol)phosphate (BMP) | 1 | BMP 14:0 14:0 | $[M^+ NH_4]^+$ | PIS, 339.3 m/z | 65 | 10 | 35 | 12 |
| phosphatidylserine (PS) | 7 | PS 17:0 17:0 | $[M + H]^+$ | NL, 185 Da | 86 | 10 | 29 | 12 |

TABLE 4-continued

Scan methods used to create MRM acquisition methods for plasma lipid profiling

| Lipid class | No. of species | Internal standard | Parent ion | MRM type | DP | EP | CE | CXP |
|---|---|---|---|---|---|---|---|---|
| phosphatidylethanolamine (PE) | 18 | PE 17:0 17:0 | $[M + H]^+$ | NL, 141 Da | 80 | 10 | 31 | 12 |
| phosphatidylinositol (PI) | 17 | PE 17:0 17:0 | $[M^+ NH_4]^+$ | PIS, 184.1 m/z | 51 | 10 | 43 | 14 |
| lysophosphatidylcholine (LPC) | 14 | LPC 13:0 | $[M + H]^+$ | PIS, 184.1 m/z | 90 | 10 | 38 | 12 |
| lysoplatelet activating factor (LPAF) | 3 | LPC 13:0 | $[M + H]^+$ | PIS, 285.2 m/z | 90 | 10 | 42 | 5 |
| phosphatidylcholine (PC) | 19 | PC 21:0 21:0[c] | $[M + H]^+$ | PIS, 184.1 m/z | 100 | 10 | 45 | 11 |
| odd-chain phosphatidylcholine (oddPC) | 15 | PC 21:0 21:0[c] | $[M + H]^+$ | PIS, 184.1 m/z | 100 | 10 | 45 | 11 |
| alkylphosphatidylcholine (APC) | 16 | PC 21:0 21:0[c] | $[M + H]^+$ | PIS, 184.1 m/z | 100 | 10 | 45 | 11 |
| modified phosphatidylcholine (modPC) | 57 | PC 21:0 21:0[c] | $[M + H]^+$ | PIS, 184.1 m/z | 100 | 10 | 45 | 11 |
| free cholesterol (COH) | 1 | COH d7 | $[M^+ NH_4]^+$ | PIS, 369.3 m/z | 55 | 10 | 17 | 12 |
| cholesterol ester (CE) | 30 | CE 18:0 d6 | $[M^+ NH_4]^+$ | PIS, 369.3 m/z | 30 | 10 | 20 | 12 |
| modified cholesterol ester (modCE) | 4 | CE 18:0 d6 | $[M^+ NH_4]^+$ | PIS, 369.3 m/z | 55 | 10 | 20 | 12 |
| diacylglycerol (DG) | 27 | DG 15:0 15:0 | $[M^+ NH_4]^+$ | NL, fatty acid | 55 | 10 | 30 | 22 |
| triacylglycerol (TG) | 44 | TG 17:0 17:0 17:0 | $[M^+ NH_4]^+$ | NL, fatty acid | 95 | 10 | 30 | 12 |

[a]NL, neutral loss scan
[b]PIS, precursor ion scan
[c]PC 13:0/13:0 was used as internal standard for species with m/z <700

TABLE 5

Clinical and biochemical characteristics of patients[a]

| Characteristic | Control (n = 61) | Stable CAD (n = 62) | Unstable CAD (n = 81) | P (stable CAD to unstable CAD)[b] | P (Control to CAD)[b] |
|---|---|---|---|---|---|
| age (years) | 60 ± 6 | 66 ± 10 | 65 ± 11 | 0.35 | <0.0001[c] |
| sex (% female) | 34 | 18 | 25 | 0.229 | 0.077 |
| smoker (%) | 3 | 15 | 30 | 0.030 | 0.001 |
| diabetes (%) | 0 | 32 | 32 | 0.976 | <0.0001 |
| hypertension (%) | 0 | 66 | 51 | 0.075 | <0.0001 |
| CAD, family history (%) | 48 | 40 | 32 | 0.335 | 0.120 |
| BMI, (kg/m²) | 25.72 ± 2.25 | 28.00 ± 4.12 | 27.65 ± 3.85 | 0.62 | 0.003 |
| total cholesterol, (mmol/L) | 4.77 ± 0.45 | 4.38 ± 1.08 | 4.11 ± 0.96 | 0.13 | 0.001 |
| LDL cholesterol, (mmol/L) | 2.93 ± 0.49 | 2.59 ± 0.93 | 2.35 ± 0.77 | 0.12 | 0.0001 |
| HDL cholesterol, (mmol/L) | 1.34 ± 0.43 | 1.09 ± 0.31 | 1.10 ± 0.29 | 0.81 | <0.0001 |
| triglycerides, (mmol/L) | 1.06 ± 0.58 | 1.63 ± 0.87 | 1.51 ± 0.97 | 0.47 | 0.0002 |
| glucose, (mmol/L) | 5.02 ± 0.48 | 6.88 ± 3.47 | 6.48 ± 2.27 | 0.45 | <0.0001 |
| hsCRP, mg/L | 2.04 ± 2.29 | 3.41 ± 3.95 | 10.32 ± 8.32 | <0.0001 | <0.0001 |

[a]Data are mean ± standard deviation
[b]p values for age, sex, smoker, diabetes, CAD family history and statin use were calculated using Chi Square. p Values for the other characteristics were calculated using Mann Whitney-U tests
[c]variable with p < 0.05 are bolded

TABLE 6

Medication of stable and unstable CAD cohorts

| Medication | Stable % | Unstable % | Chi Square value | Significance |
|---|---|---|---|---|
| Clopidogrel[a] | 18 | 27 | 1.625 | 0.202 |
| Aspirin[a] | 95 | 94 | 0.103 | 0.748 |
| statin[b] | 54 | 88 | 19.991 | 0.000[h] |
| beta blocker[c] | 59 | 65 | 0.612 | 0.434 |
| ACE inhibitor[c] | 43 | 56 | 2.328 | 0.127 |
| angiotensin-II blocker[c] | 23 | 6 | 1.076 | 0.300 |
| oral/top nitrate[c] | 31 | 27 | 0.269 | 0.604 |
| intravenous glyceryl trinitrate (IV GTN)[c] | 0 | 6 | 3.903 | 0.048 |
| Ca channel blacker[c] | 26 | 19 | 1.212 | 0.271 |
| heparin infusion[d] | 0 | 21 | 14.544 | 0.000 |
| low molecular weight heparin (LMWH)[d] | 0 | 11 | 7.236 | 0.007 |
| insulin[g] | 7 | 5 | 0.172 | 0.679 |
| warfarin[d] | 2 | 0 | 1.337 | 0.248 |
| amiodarone[f] | 2 | 1 | 0.041 | 0.839 |
| spironolactone[e] | 3 | 0 | 2.694 | 0.101 |
| abciximab[a] | 0 | 1 | 0.758 | 0.384 |
| tirofiban[a] | 0 | 6 | 3.903 | 0.048 |
| frusemide[e] | 11 | 9 | 0.314 | 0.575 |
| sulfonylurea[g] | 15 | 14 | 0.040 | 0.842 |
| metformin[g] | 23 | 11 | 3.593 | 0.058 |

[a]antiplatelet
[b]lipid lowering
[c]antihypertensive
[d]anticoagulant
[e]anti-anginal
[f]anti-arrhythmic
[g]anti-diabetic
[h]variable with p < 0.05 are bolded

TABLE 7

Lipid analytes measured in MRM experiment 1

| # | Analyte | exact mass | Q1[a] | Q3[b] | tR[c] | ID[d] | DP[e] | EP[f] | CE[g] | CXP[h] |
|---|---|---|---|---|---|---|---|---|---|---|
| 1 | Cer 16:0 | 537.512 | 538.5 | 264.3 | 7.10 | Cer 16:0 | 50 | 10 | 35 | 12 |
| S1 | Cer 17:0 (IS) | 551.528 | 552.5 | 264.3 | 7.26 | Cer 17:0 (IS) | 50 | 10 | 35 | 12 |
| 2 | Cer 18:1 | 563.528 | 564.5 | 264.3 | 7.20 | Cer 18:1 | 50 | 10 | 35 | 12 |
| 3 | Cer 18:0 | 565.543 | 566.6 | 264.3 | 7.41 | Cer 18:0 | 50 | 10 | 35 | 12 |
| 4 | Cer 20:0 | 593.575 | 594.6 | 264.3 | 7.80 | Cer 20:0 | 50 | 10 | 35 | 12 |
| 5 | Cer 22:0 | 621.606 | 622.6 | 264.3 | 7.94 | Cer 22:0 | 50 | 10 | 35 | 12 |
| 6 | Cer 24:1 | 647.622 | 648.6 | 264.3 | 7.95 | Cer 24:1 | 50 | 10 | 35 | 12 |
| 7 | Cer 24:0 | 649.637 | 650.6 | 264.3 | 8.18 | Cer 24:0 | 50 | 10 | 35 | 12 |
| 8 | MHC 16:0 | 699.565 | 700.6 | 264.3 | 6.26 | MHC 16:0 | 77 | 10 | 50 | 12 |
| S2 | MHC 16:0d3 (IS) | 702.582 | 703.60 | 264.3 | 6.26 | MHC 16:0d3 (IS) | 77 | 10 | 50 | 12 |
| 9 | MHC 18:1 | 725.581 | 726.6 | 264.3 | 6.40 | MHC 18:1 | 77 | 10 | 50 | 12 |
| 10 | MHC 18:0 | 727.596 | 728.6 | 264.3 | 6.61 | MHC 18:0 | 77 | 10 | 50 | 12 |
| 11 | MHC 20:0 | 755.628 | 756.6 | 264.3 | 6.93 | MHC 20:0 | 77 | 10 | 50 | 12 |
| 12 | MHC 22:0 | 783.659 | 784.7 | 264.3 | 7.21 | MHC 22:0 | 77 | 10 | 50 | 12 |
| 13 | MHC 24:1 | 809.674 | 810.7 | 264.3 | 7.22 | MHC 24:1 | 77 | 10 | 50 | 12 |
| 14 | MHC 24:0 | 811.690 | 812.7 | 264.3 | 7.47 | MHC 24:0 | 77 | 10 | 50 | 12 |
| 15 | DHC 16:0 | 861.618 | 862.6 | 264.3 | 5.91 | DHC 16:0 | 100 | 10 | 65 | 12 |
| S3 | DHC 16:0d3 (IS) | 864.635 | 865.6 | 264.3 | 5.91 | DHC 16:0d3 (IS) | 100 | 10 | 65 | 12 |
| 16 | DHC 18:1 | 887.633 | 888.6 | 264.3 | 6.03 | DHC 18:1 | 100 | 10 | 65 | 12 |
| 17 | DHC 18:0 | 889.649 | 890.7 | 264.3 | 6.27 | DHC 18:0 | 100 | 10 | 65 | 12 |
| 18 | DHC 20:0 | 917.680 | 918.7 | 264.3 | 6.60 | DHC 20:0 | 100 | 10 | 65 | 12 |
| 19 | DHC 22:0 | 945.712 | 946.7 | 264.3 | 6.90 | DHC 22:0 | 100 | 10 | 65 | 12 |
| 20 | DHC 24:1 | 971.727 | 972.7 | 264.3 | 6.91 | DHC 24:1 | 100 | 10 | 65 | 12 |
| 21 | DHC 24:0 | 973.743 | 974.8 | 264.3 | 7.17 | DHC 24:0 | 100 | 10 | 65 | 12 |
| 22 | THC 16:0 | 1023.671 | 1024.7 | 264.3 | 5.69 | THC 16:0 | 130 | 10 | 73 | 12 |
| S4 | THC 17:0 (IS) | 1037.686 | 1038.7 | 264.3 | 5.87 | THC 17:0 (IS) | 130 | 10 | 73 | 12 |
| 23 | THC 18:1 | 1049.686 | 1050.7 | 264.3 | 5.84 | THC 18:1 | 130 | 10 | 73 | 12 |
| 24 | THC 18:0 | 1051.702 | 1052.7 | 264.3 | 6.06 | THC 18:0 | 130 | 10 | 73 | 12 |
| 25 | THC 20:0 | 1079.733 | 1080.7 | 264.3 | 6.39 | THC 20:0 | 130 | 10 | 73 | 12 |
| 26 | THC 22:0 | 1107.764 | 1108.8 | 264.3 | 6.70 | THC 22:0 | 130 | 10 | 73 | 12 |
| 27 | THC 24:1 | 1133.780 | 1134.8 | 264.3 | 6.70 | THC 24:1 | 130 | 10 | 73 | 12 |
| 28 | THC 24:0 | 1135.796 | 1136.8 | 264.3 | 6.98 | THC 24:0 | 130 | 10 | 73 | 12 |
| 29 | GM3 16:0 | 1152.713 | 1153.7 | 264.3 | 4.82 | GM3 16:0 | 155 | 10 | 105 | 16 |
| 30 | GM3 18:0 | 1180.744 | 1181.8 | 264.3 | 5.15 | GM3 18:0 | 155 | 10 | 105 | 16 |
| 31 | GM3 20:0 | 1208.776 | 1209.8 | 264.3 | 5.49 | GM3 20:0 | 155 | 10 | 105 | 16 |
| 32 | GM3 22:0 | 1236.807 | 1237.8 | 264.3 | 5.77 | GM3 22:0 | 155 | 10 | 105 | 16 |
| 33 | GM3 24:1 | 1262.823 | 1263.8 | 264.3 | 5.78 | GM3 24:1 | 155 | 10 | 105 | 16 |
| 34 | GM3 24:0 | 1264.838 | 1265.8 | 264.3 | 6.04 | GM3 24:0 | 155 | 10 | 105 | 16 |
| 35 | modCer 576.5/7.68 | 575.500 | 576.5 | 264.3 | 7.68 | modCer 576.5/7.68 | 70 | 10 | 50 | 16 |
| 36 | modCer 614.6/5.72 | 613.600 | 614.6 | 264.3 | 5.72 | modCer 614.6/5.72 | 70 | 10 | 50 | 16 |
| 37 | modCer 632.6/9.22 | 631.600 | 632.6 | 264.3 | 9.22 | modCer 632.6/9.22 | 70 | 10 | 50 | 16 |
| 38 | modCer 651.6/7.56 | 650.600 | 651.6 | 264.3 | 7.56 | modCer 651.6/7.56 | 70 | 10 | 50 | 16 |
| 39 | modCer 703.6/5.87 | 702.620 | 703.61 | 264.3 | 5.87 | modCer 703.6/5.87 | 70 | 10 | 50 | 16 |
| 40 | modCer 731.6/6.22 | 730.600 | 731.6 | 264.3 | 6.22 | modCer 731.6/6.22 | 70 | 10 | 50 | 16 |
| 41 | modCer 766.6/7.17 | 765.600 | 766.6 | 264.3 | 7.17 | modCer 766.6/7.17 | 70 | 10 | 50 | 16 |
| 42 | modCer 769.6/8.01 | 768.600 | 769.6 | 264.3 | 8.01 | modCer 769.6/8.01 | 70 | 10 | 50 | 16 |
| 43 | modCer 798.7/7.29 | 797.700 | 798.7 | 264.3 | 7.29 | modCer 798.7/7.29 | 70 | 10 | 50 | 16 |
| S5 | Acyl Cer 17:0 18:1 (IS) | 815.800 | 816.8 | 264.3 | 8.90 | Acyl Cer 17:0 18:1 (IS) | 70 | 10 | 50 | 16 |
| 44 | modCer 875.7/9.23 | 874.700 | 875.7 | 264.3 | 9.23 | modCer 875.7/9.23 | 70 | 10 | 50 | 16 |
| 45 | modCer 883.8/7.75 | 882.800 | 883.8 | 264.3 | 7.75 | modCer 883.8/7.75 | 70 | 10 | 50 | 16 |
| 46 | modCer 886.8/9.06 | 885.800 | 886.8 | 264.3 | 9.06 | modCer 886.8/9.06 | 70 | 10 | 50 | 16 |
| 47 | modCer 910.8/8.98 | 909.800 | 910.8 | 264.3 | 8.98 | modCer 910.8/8.98 | 70 | 10 | 50 | 16 |
| 48 | modCer 921.8/9.05 | 920.800 | 921.8 | 264.3 | 9.05 | modCer 921.8/9.05 | 70 | 10 | 50 | 16 |
| S6 | SM 12:0 (IS) | 646.505 | 647.5 | 184.1 | 4.70 | SM 12:0 (IS) | 65 | 10 | 35 | 12 |
| S6 | SM 12:0 (IS) | 646.505 | 648.5 | 185.1 | 4.70 | SM 12:0 + 1 (IS) | 65 | 10 | 35 | 12 |
| S6 | SM 12:0 (IS) | 646.505 | 649.5 | 186.1 | 4.70 | SM 12:0 + 2 (IS) | 65 | 10 | 35 | 12 |
| 49 | SM 14:0 | 674.536 | 676.5 | 185.1 | 5.15 | SM 14:0 + 1 | 65 | 10 | 35 | 12 |
| 50 | SM 15:0 | 688.552 | 690.6 | 185.1 | 5.40 | SM 15:0 + 1 | 65 | 10 | 35 | 12 |
| 51 | SM 16:1 | 700.552 | 702.6 | 185.1 | 5.30 | SM 16:1 + 1 | 65 | 10 | 35 | 12 |
| 52 | SM 16:0 | 702.568 | 705.6 | 186.1 | 5.58 | SM 16:0 + 2 | 65 | 10 | 35 | 12 |
| 53 | SM 18:1 | 728.583 | 730.6 | 185.1 | 5.70 | SM 18:1 + 1 | 65 | 10 | 35 | 12 |
| 54 | SM 18:0 | 730.599 | 732.6 | 185.1 | 6.04 | SM 18:0 + 1 | 65 | 10 | 35 | 12 |
| 55 | SM 20:1 | 756.615 | 758.6 | 185.1 | 6.09 | SM 20:1 + 1 | 65 | 10 | 35 | 12 |
| 56 | SM 22:1 | 784.646 | 786.7 | 185.1 | 6.44 | SM 22:1 + 1 | 65 | 10 | 35 | 12 |
| 57 | SM 22:0 | 786.661 | 788.7 | 185.1 | 6.68 | SM 22:0 + 1 | 65 | 10 | 35 | 12 |
| 58 | SM 24:2 | 810.661 | 812.7 | 185.1 | 6.46 | SM 24:2 + 1 | 65 | 10 | 35 | 12 |
| 59 | SM 24:1 | 812.677 | 813.7 | 184.1 | 6.60 | SM 24:1 | 65 | 10 | 35 | 12 |
| 60 | SM 24:0 | 814.693 | 816.7 | 185.1 | 6.98 | SM 24:0 + 1 | 65 | 10 | 35 | 12 |
| 61 | PG 16:1 18:1 | 746.510 | 764.5 | 575.5 | 5.44 | PG 16:1 18:1 | 60 | 10 | 25 | 12 |
| 62 | PG 16:0 18:1 | 748.525 | 766.6 | 577.5 | 5.68 | PG 16:0 18:1 | 60 | 10 | 25 | 12 |
| S7 | PG 17:0 17:0 (IS) | 750.541 | 768.6 | 579.5 | 5.93 | PG 17:0 17:0 (IS) | 60 | 10 | 25 | 12 |
| 63 | PG 18:1 18:1 | 774.541 | 792.6 | 603.5 | 5.76 | PG 18:1 18:1 | 60 | 10 | 25 | 12 |
| 64 | PG 18:0 18:1 | 776.557 | 794.6 | 605.6 | 6.00 | PG 18:0 18:1 | 60 | 10 | 25 | 12 |
| S8 | BMP 14:0 14:0 (IS) | 666.447 | 684.5 | 285.2 | 5.01 | BMP 14:0 14:0 (IS) | 65 | 10 | 35 | 5 |
| 65 | BMP 18:1 18:1 | 774.541 | 792.6 | 339.3 | 5.76 | BMP 18:1 18:1 | 65 | 10 | 35 | 5 |
| S9 | PS 17:0/17:0 | 763.536 | 764.5 | 579.5 | 5.78 | PS 17:0/17:0 | 86 | 10 | 29 | 16 |

TABLE 7-continued

Lipid analytes measured in MRM experiment 1

| # | Analyte | exact mass | Q1[a] | Q3[b] | tR[c] | ID[d] | DP[e] | EP[f] | CE[g] | CXP[h] |
|---|---------|-----------|------|------|------|-----|-----|-----|-----|------|
| 66 | PS 36:2 | 787.536 | 788.5 | 603.5 | 5.67 | PS 36:2 | 86 | 10 | 29 | 16 |
| 67 | PS 36:1 | 789.552 | 790.6 | 605.6 | 5.87 | PS 36:1 | 86 | 10 | 29 | 16 |
| 68 | PS 38:5 | 809.521 | 810.5 | 625.5 | 5.49 | PS 38:5 | 86 | 10 | 29 | 16 |
| 69 | PS 38:4 | 811.536 | 812.5 | 627.5 | 5.69 | PS 38:4 | 86 | 10 | 29 | 16 |
| 70 | PS 38:3 | 813.552 | 814.6 | 629.6 | 5.82 | PS 38:3 | 86 | 10 | 29 | 16 |
| 71 | PS 40:6 | 835.536 | 836.5 | 651.5 | 5.69 | PS 40:6 | 86 | 10 | 29 | 16 |
| 72 | PS 40:5 | 837.552 | 838.6 | 653.6 | 5.73 | PS 40:5 | 86 | 10 | 29 | 16 |
| 73 | PE 32:1 | 689.500 | 690.5 | 549.5 | 6.25 | PE 32:1 | 80 | 10 | 31 | 7 |
| 74 | PE 32:0 | 691.515 | 692.5 | 551.5 | 6.40 | PE 32:0 | 80 | 10 | 31 | 7 |
| 75 | PE 34:2 | 715.515 | 716.5 | 575.5 | 6.30 | PE 34:2 | 80 | 10 | 31 | 7 |
| 76 | PE 34:1 | 717.531 | 718.5 | 577.5 | 6.50 | PE 34:1 | 80 | 10 | 31 | 7 |
| S10 | PE 17:0/17:0 (IS) | 719.547 | 720.6 | 579.5 | 6.53 | PE 17:0/17:0 (IS) | 80 | 10 | 31 | 7 |
| 77 | PE 36:5 | 737.500 | 738.5 | 597.5 | 6.15 | PE 36:5 | 80 | 10 | 31 | 7 |
| 78 | PE 36:4 | 739.515 | 740.5 | 599.5 | 6.33 | PE 36:4 | 80 | 10 | 31 | 7 |
| 79 | PE 36:3 | 741.531 | 742.5 | 601.5 | 6.39 | PE 36:3 | 80 | 10 | 31 | 7 |
| 80 | PE 36:2 | 743.547 | 744.6 | 603.5 | 6.57 | PE 36:2 | 80 | 10 | 31 | 7 |
| 81 | PE 36:1 | 745.562 | 746.6 | 605.6 | 6.83 | PE 36:1 | 80 | 10 | 31 | 7 |
| 82 | PE 36:0 | 747.578 | 748.6 | 607.6 | 7.00 | PE 36:0 | 80 | 10 | 31 | 7 |
| 83 | PE 38:6 | 763.515 | 764.5 | 623.5 | 6.31 | PE 38:6 | 80 | 10 | 31 | 7 |
| 84 | PE 38:5 | 765.531 | 766.5 | 625.5 | 6.40 | PE 38:5 | 80 | 10 | 31 | 7 |
| 85 | PE38:4 | 767.547 | 768.6 | 627.5 | 6.66 | PE38:4 | 80 | 10 | 31 | 7 |
| 86 | PE 38:3 | 769.562 | 770.6 | 629.6 | 6.84 | PE 38:3 | 80 | 10 | 31 | 7 |
| 87 | PE 38:2 | 771.578 | 772.6 | 631.6 | 6.86 | PE 38:2 | 80 | 10 | 31 | 7 |
| 88 | PE 38:1 | 773.593 | 774.6 | 633.6 | 7.07 | PE 38:1 | 80 | 10 | 31 | 7 |
| 89 | PE 40:7 | 789.531 | 790.6 | 649.5 | 6.38 | PE 40:7 | 80 | 10 | 31 | 7 |
| 90 | PE 40:6 | 791.547 | 792.6 | 651.5 | 6.63 | PE 40:6 | 80 | 10 | 31 | 7 |
| 91 | PI 32:1 | 808.510 | 826.5 | 549.5 | 5.09 | PI 32:1 | 51 | 10 | 43 | 14 |
| 92 | PI 32:0 | 810.526 | 828.6 | 551.6 | 5.34 | PI 32:0 | 51 | 10 | 43 | 14 |
| 93 | PI 34:1 | 836.541 | 854.6 | 577.6 | 5.44 | PI 34:1 | 51 | 10 | 43 | 14 |
| 94 | PI 34:0 | 838.557 | 856.6 | 579.6 | 5.69 | PI 34:0 | 51 | 10 | 43 | 14 |
| 95 | PI 36:4 | 858.526 | 876.6 | 599.6 | 5.26 | PI 36:4 | 51 | 10 | 43 | 14 |
| 96 | PI 36:3 | 860.541 | 878.6 | 601.6 | 5.32 | PI 36:3 | 51 | 10 | 43 | 14 |
| 97 | PI 36:2 | 862.557 | 880.6 | 603.6 | 5.58 | PI 36:2 | 51 | 10 | 43 | 14 |
| 98 | PI 36:1 | 864.573 | 882.6 | 605.6 | 5.77 | PI 36:1 | 51 | 10 | 43 | 14 |
| 99 | PI 36:0 | 866.588 | 884.6 | 607.6 | 5.99 | PI 36:0 | 51 | 10 | 43 | 14 |
| 100 | PI 38:6 | 882.526 | 900.6 | 623.6 | 5.26 | PI 38:6 | 51 | 10 | 43 | 14 |
| 101 | PI 38:5 | 884.541 | 902.6 | 625.6 | 5.34 | PI 38:5 | 51 | 10 | 43 | 14 |
| 102 | PI 38:4 | 886.557 | 904.6 | 627.6 | 5.61 | PI 38:4 | 51 | 10 | 43 | 14 |
| 103 | PI 38:3 | 888.573 | 906.6 | 629.6 | 5.71 | PI 38:3 | 51 | 10 | 43 | 14 |
| 104 | PI 38:2 | 890.588 | 908.6 | 631.6 | 5.86 | PI 38:2 | 51 | 10 | 43 | 14 |
| 105 | PI 40:6 | 910.557 | 928.6 | 651.6 | 5.60 | PI 40:6 | 51 | 10 | 43 | 14 |
| 106 | PI 40:5 | 912.573 | 930.6 | 653.6 | 5.67 | PI 40:5 | 51 | 10 | 43 | 14 |
| 107 | PI 40:4 | 914.588 | 932.6 | 655.6 | 5.84 | PI 40:4 | 51 | 10 | 43 | 14 |
| S11 | LPC 13:0 (IS) | 453.286 | 454.3 | 184.1 | 1.22 | LPC 13:0 (IS) | 90 | 10 | 38 | 12 |
| 108 | LPC 14:0 | 467.301 | 468.3 | 184.1 | 1.20 | LPC 14:0 | 90 | 10 | 38 | 12 |
| 109 | LPC 15:0 | 481.317 | 482.3 | 184.1 | 1.70 | LPC 15:0 | 90 | 10 | 38 | 12 |
| 110 | LPC 16:1 | 493.317 | 494.3 | 184.1 | 1.50 | LPC 16:1 | 90 | 10 | 38 | 12 |
| 111 | LPC 16:0 | 495.332 | 496.3 | 184.1 | 2.30 | LPC 16:0 | 90 | 10 | 38 | 12 |
| 112 | LPC 18:2 | 519.332 | 520.3 | 184.1 | 1.90 | LPC 18:2 | 90 | 10 | 38 | 12 |
| 113 | LPC 18:1 | 521.348 | 522.4 | 184.1 | 2.80 | LPC 18:1 | 90 | 10 | 38 | 12 |
| 114 | LPC 18:0 | 523.364 | 524.4 | 184.1 | 3.60 | LPC 18:0 | 90 | 10 | 38 | 12 |
| 115 | LPC 20:5 | 541.317 | 542.3 | 184.1 | 1.51 | LPC 20:5 | 90 | 10 | 38 | 12 |
| 116 | LPC 20:4 | 543.332 | 544.3 | 184.1 | 2.00 | LPC 20:4 | 90 | 10 | 38 | 12 |
| 117 | LPC 20:3 | 545.348 | 546.4 | 184.1 | 2.51 | LPC 20:3 | 90 | 10 | 38 | 12 |
| 118 | LPC 20:2 | 547.364 | 548.4 | 184.1 | 3.60 | LPC 20:2 | 90 | 10 | 38 | 12 |
| 119 | LPC 20:1 | 549.379 | 550.4 | 184.1 | 3.80 | LPC 20:1 | 90 | 10 | 38 | 12 |
| 120 | LPC 20:0 | 551.395 | 552.41 | 184.1 | 4.30 | LPC 20:0 | 90 | 10 | 38 | 12 |
| 121 | LPC 22:6 | 567.332 | 568.3 | 184.1 | 2.10 | LPC 22:6 | 90 | 10 | 38 | 12 |
| 122 | LPAF 16:0 | 481.353 | 482.4 | 104.1 | 3.00 | LPAF 16:0 | 90 | 10 | 42 | 5 |
| 123 | LPAF 18:1 | 507.369 | 508.4 | 104.1 | 3.30 | LPAF 18:1 | 90 | 10 | 42 | 5 |
| 124 | LPAF 18:0 | 509.385 | 510.4 | 104.1 | 3.90 | LPAF 18:0 | 90 | 10 | 42 | 5 |
| S12 | PC 13:0/13:0 | 649.468 | 650.5 | 184.1 | 5.05 | PC 13: 13:0 (IS) | 100 | 10 | 45 | 11 |
| S12 | PC 13:0/13:0 | 650.492 | 651.5 | 185.1 | 5.05 | PC 13: 13:0 + 1 (IS) | 100 | 10 | 45 | 11 |
| 125 | PC 30:2 | 701.500 | 703.5 | 185.1 | 5.31 | PC 30:2 + 1 | 100 | 10 | 45 | 11 |
| 126 | PC 32:2 | 729.531 | 731.5 | 185.1 | 5.80 | PC 32:2 + 1 | 100 | 10 | 45 | 11 |
| 127 | PC 32:1 | 732.547 | 733.6 | 184.1 | 5.96 | PC 32:1 + 1 | 100 | 10 | 45 | 11 |
| 128 | PC 32:0 | 733.562 | 735.6 | 185.1 | 6.24 | PC 32:0 + 1 | 100 | 10 | 45 | 11 |
| 129 | PC 34:3 | 755.547 | 757.6 | 185.1 | 5.88 | PC 34:3 + 1 | 100 | 10 | 45 | 11 |
| 130 | PC 34:2 | 757.562 | 760.6 | 186.1 | 6.16 | PC 34:2 + 2 | 100 | 10 | 45 | 11 |
| 131 | PC 34:1 | 759.578 | 761.6 | 185.1 | 6.28 | PC 34:1 + 1 | 100 | 10 | 45 | 11 |
| 132 | PC 34:0 | 761.593 | 763.6 | 185.1 | 6.37 | PC 34:0 + 1 | 100 | 10 | 45 | 11 |
| 133 | PC 36:5 | 779.547 | 781.6 | 185.1 | 5.92 | PC 36:5 + 1 | 100 | 10 | 45 | 11 |
| 134 | PC 36:4 | 781.562 | 784.6 | 186.1 | 6.17 | PC 36:4 + 2 | 100 | 10 | 45 | 11 |
| 135 | PC 36:3 | 783.578 | 785.6 | 185.1 | 6.25 | PC 36:3 + 1 | 100 | 10 | 45 | 11 |
| 136 | PC 36:2 | 785.593 | 788.6 | 186.1 | 6.40 | PC 36:2 + 2 | 100 | 10 | 45 | 11 |
| 137 | PC 38:6 | 805.562 | 807.6 | 185.1 | 6.16 | PC 38:6 + 1 | 100 | 10 | 45 | 11 |

TABLE 7-continued

Lipid analytes measured in MRM experiment 1

| # | Analyte | exact mass | Q1[a] | Q3[b] | tR[c] | ID[d] | DP[e] | EP[f] | CE[g] | CXP[h] |
|---|---|---|---|---|---|---|---|---|---|---|
| 138 | PC 38:5 | 807.578 | 809.6 | 185.1 | 6.23 | PC 38:5 + 1 | 100 | 10 | 45 | 11 |
| 139 | PC 38:4 | 809.593 | 812.6 | 186.1 | 6.50 | PC 38:4 + 2 | 100 | 10 | 45 | 11 |
| 140 | PC 40:7 | 831.578 | 833.6 | 185.1 | 6.20 | PC 40:7 + 1 | 100 | 10 | 45 | 11 |
| 141 | PC 40:6 | 833.593 | 835.6 | 185.1 | 6.50 | PC 40:6 + 1 | 100 | 10 | 45 | 11 |
| 142 | PC 40:5 | 835.609 | 837.6 | 185.1 | 6.55 | PC 40:5 + 1 | 100 | 10 | 45 | 11 |
| S13 | PC 21:0 21:0 (IS) | 873.719 | 874.7 | 184.1 | 7.80 | PC 21:0 21:0 (IS) | 100 | 10 | 45 | 11 |
| S13 | PC 21:0 21:0 (IS) | 874.719 | 875.7 | 185.1 | 7.80 | PC 21:0 21:0 + 1 (IS) | 100 | 10 | 45 | 11 |
| S13 | PC 21:0 21:0 (IS) | 875.719 | 876.7 | 186.1 | 7.80 | PC 21:0 21:0 + 2 (IS) | 100 | 10 | 45 | 11 |
| 143 | PC 44:12 | 877.562 | 879.6 | 185.1 | 7.22 | PC 44:12 + 1 | 100 | 10 | 45 | 11 |
| 144 | oddPC 31:1 | 717.531 | 718.5 | 184.1 | 5.94 | PC 31:1 | 100 | 10 | 45 | 11 |
| 145 | oddPC 31:0 | 719.547 | 720.60 | 184.1 | 6.20 | PC 31:0 | 100 | 10 | 45 | 11 |
| 146 | oddPC 33:0 | 743.547 | 744.60 | 184.1 | 6.07 | PC 33:2 | 100 | 10 | 45 | 11 |
| 147 | oddPC 33:1 | 745.562 | 746.60 | 184.1 | 6.29 | PC 33:1 | 100 | 10 | 45 | 11 |
| 148 | oddPC 33:2 | 747.578 | 748.6 | 184.1 | 6.50 | PC 33:0 | 100 | 10 | 45 | 11 |
| 149 | oddPC 35:4 | 767.547 | 768.60 | 184.1 | 6.09 | PC 35:4 | 100 | 10 | 45 | 11 |
| 150 | oddPC 35:3 | 769.562 | 770.60 | 184.1 | 6.19 | PC 35:3 | 100 | 10 | 45 | 11 |
| 151 | oddPC 35:2 | 771.578 | 772.6 | 184.1 | 6.41 | PC 35:2 | 100 | 10 | 45 | 11 |
| 152 | oddPC 35:1 | 773.593 | 774.60 | 184.1 | 6.63 | PC 35:1 | 100 | 10 | 45 | 11 |
| 153 | oddPC 35:0 | 775.609 | 776.6 | 184.1 | 6.83 | PC 35:0 | 100 | 10 | 45 | 11 |
| 154 | oddPC 37:6 | 791.547 | 792.60 | 184.1 | 6.07 | PC 37:6 | 100 | 10 | 45 | 11 |
| 155 | oddPC 37:5 | 793.562 | 794.60 | 184.1 | 6.22 | PC 37:5 | 100 | 10 | 45 | 11 |
| 156 | oddPC 37:4 | 795.578 | 796.60 | 184.1 | 6.41 | PC 37:4 | 100 | 10 | 45 | 11 |
| 157 | oddPC 37:3 | 797.593 | 798.60 | 184.1 | 6.60 | PC 37:3 | 100 | 10 | 45 | 11 |
| 158 | oddPC 37:2 | 799.609 | 800.6 | 184.1 | 6.71 | PC 37:2 | 100 | 10 | 45 | 11 |
| 159 | APC 32:1 | 717.567 | 718.6 | 184.1 | 6.28 | APC 32:1 | 100 | 10 | 45 | 11 |
| 160 | APC 32:0 | 719.583 | 720.61 | 184.1 | 6.53 | APC 32:0 | 100 | 10 | 45 | 11 |
| 161 | APC 34:2 | 743.583 | 744.61 | 184.1 | 6.40 | APC 34:2 | 100 | 10 | 45 | 11 |
| 162 | APC 34:1 | 745.599 | 746.61 | 184.1 | 6.59 | APC 34:1 | 100 | 10 | 45 | 11 |
| 163 | APC 34:0 | 747.614 | 748.6 | 184.1 | 6.88 | APC 34:0 | 100 | 10 | 45 | 11 |
| 164 | APC 36:5 | 765.567 | 766.6 | 184.1 | 6.30 | APC 36:5 | 100 | 10 | 45 | 11 |
| 165 | APC 36:4 | 767.583 | 768.61 | 184.1 | 6.41 | APC 36:4 | 100 | 10 | 45 | 11 |
| 166 | APC 36:3 | 769.599 | 770.61 | 184.1 | 6.59 | APC 36:3 | 100 | 10 | 45 | 11 |
| 167 | APC 36:2 | 771.614 | 772.6 | 184.1 | 6.69 | APC 36:2 | 100 | 10 | 45 | 11 |
| 168 | APC 36:1 | 773.630 | 774.61 | 184.1 | 6.95 | APC 36:1 | 100 | 10 | 45 | 11 |
| 169 | APC 36:0 | 775.645 | 776.7 | 184.1 | 7.20 | APC 36:0 | 100 | 10 | 45 | 11 |
| 170 | APC 38:6 | 791.583 | 792.61 | 184.1 | 6.39 | APC 38:6 | 100 | 10 | 45 | 11 |
| 171 | APC 38:5 | 793.599 | 794.60 | 184.1 | 6.52 | APC 38:5 | 100 | 10 | 45 | 11 |
| 172 | APC 38:4 | 795.614 | 796.61 | 184.1 | 6.75 | APC 38:4 | 100 | 10 | 45 | 11 |
| 173 | APC 38:3 | 797.630 | 798.61 | 184.1 | 6.86 | APC 38:3 | 100 | 10 | 45 | 11 |
| 174 | APC 38:2 | 799.645 | 800.7 | 184.1 | 7.03 | APC 38:2 | 100 | 10 | 45 | 11 |
| 175 | modPC 506.3/3.50 | 505.300 | 506.3 | 184.1 | 3.50 | modPC 506.3/3.50 | 100 | 10 | 45 | 11 |
| 176 | modPC 508.3/3.30 | 507.310 | 508.3 | 184.1 | 3.30 | modPC 508.3/3.30 | 100 | 10 | 45 | 11 |
| 177 | modPC 510.3/4.00 | 509.300 | 510.3 | 184.1 | 4.00 | modPC 510.3/4.00 | 100 | 10 | 45 | 11 |
| 178 | modPC 512.3/1.70 | 511.300 | 512.3 | 184.1 | 1.70 | modPC 512.3/1.70 | 100 | 10 | 45 | 11 |
| 179 | modPC 536.3/3.50 | 535.300 | 536.3 | 184.1 | 3.50 | modPC 536.3/3.50 | 100 | 10 | 45 | 11 |
| 180 | modPC 538.3/4.10 | 537.300 | 538.3 | 184.1 | 4.10 | modPC 538.3/4.10 | 100 | 10 | 45 | 11 |
| 181 | modPC 552.4/3.90 | 551.400 | 552.40 | 184.1 | 3.90 | modPC 552.4/3.90 | 100 | 10 | 45 | 11 |
| 182 | modPC 564.4/4.70 | 563.400 | 564.4 | 184.1 | 4.70 | modPC 564.4/4.70 | 100 | 10 | 45 | 11 |
| 183 | modPC 566.4/5.10 | 565.400 | 566.4 | 184.1 | 5.10 | modPC 566.4/5.10 | 100 | 10 | 45 | 11 |
| 184 | modPC 580.4/4.84 | 579.400 | 580.4 | 184.1 | 4.84 | modPC 580.4/4.84 | 100 | 10 | 45 | 11 |
| 185 | modPC 590.4/4.80 | 589.400 | 590.4 | 184.1 | 4.80 | modPC 590.4/4.80 | 100 | 10 | 45 | 11 |
| 186 | modPC 592.4/5.10 | 591.400 | 592.4 | 184.1 | 5.10 | modPC 592.4/5.10 | 100 | 10 | 45 | 11 |
| 187 | modPC 594.4/3.26 | 593.400 | 594.4 | 184.1 | 3.26 | modPC 594.4/3.26 | 100 | 10 | 45 | 11 |
| 188 | modPC 608.4/5.33 | 607.410 | 608.41 | 184.1 | 5.33 | modPC 608.4/5.33 | 100 | 10 | 45 | 11 |
| 189 | modPC 608.4/3.84 | 607.400 | 608.40 | 184.1 | 3.84 | modPC 608.4/3.84 | 100 | 10 | 45 | 11 |
| 190 | modPC 610.4/2.03 | 609.400 | 610.4 | 184.1 | 2.03 | modPC 610.4/2.03 | 100 | 10 | 45 | 11 |
| 191 | modPC 622.4/4.54 | 621.400 | 622.4 | 184.1 | 4.54 | modPC 622.4/4.54 | 100 | 10 | 45 | 11 |
| 192 | modPC 633.4/4.51 | 632.400 | 633.4 | 184.1 | 4.51 | modPC 633.4/4.51 | 100 | 10 | 45 | 11 |
| 193 | modPC 636.4/3.37 | 635.400 | 636.4 | 184.1 | 3.37 | modPC 636.4/3.37 | 100 | 10 | 45 | 11 |
| 194 | modPC 645.4/4.49 | 644.400 | 645.4 | 184.1 | 4.49 | modPC 645.4/4.49 | 100 | 10 | 45 | 11 |
| 195 | modPC 650.4/3.24 | 649.403 | 650.40 | 184.1 | 3.24 | modPC 650.4/3.24 | 100 | 10 | 45 | 11 |
| 196 | modPC 650.4/4.44 | 649.430 | 650.42 | 184.1 | 4.44 | modPC 650.4/4.44 | 100 | 10 | 45 | 11 |
| 197 | modPC 650.4/3.94 | 649.420 | 650.41 | 184.1 | 3.94 | modPC 650.4/3.94 | 100 | 10 | 45 | 11 |
| 198 | modPC 664.4/4.22 | 663.420 | 664.4 | 184.1 | 4.32 | modPC 664.4/4.22 | 100 | 10 | 45 | 11 |
| 199 | modPC 666.4/2.99 | 665.400 | 666.4 | 184.1 | 2.99 | modPC 666.4/2.99 | 100 | 10 | 45 | 11 |
| 200 | modPC 678.4/4.37 | 677.400 | 678.40 | 184.1 | 4.37 | modPC 678.4/4.37 | 100 | 10 | 45 | 11 |
| 201 | modPC 678.4/4.94 | 677.410 | 678.41 | 184.1 | 5.16 | modPC 678.4/4.94 | 100 | 10 | 45 | 11 |
| 202 | modPC 678.4/5.51 | 677.420 | 678.42 | 184.1 | 5.34 | modPC 678.4/5.51 | 100 | 10 | 45 | 11 |
| 203 | modPC 690.4/4.11 | 689.400 | 690.40 | 184.1 | 4.11 | modPC 690.4/4.11 | 100 | 10 | 45 | 11 |
| 204 | modPC 690.4/4.90 | 689.400 | 690.41 | 184.1 | 4.90 | modPC 690.4/4.90 | 100 | 10 | 45 | 11 |
| 205 | modPC 690.4/6.00 | 689.410 | 690.42 | 184.1 | 6.00 | modPC 690.4/6.00 | 100 | 10 | 45 | 11 |
| 206 | modPC 692.4/5.05 | 691.400 | 692.40 | 184.1 | 5.05 | modPC 692.4/5.05 | 100 | 10 | 45 | 11 |
| 207 | modPC 692.4/5.52 | 691.420 | 692.41 | 184.1 | 5.52 | modPC 692.4/5.52 | 100 | 10 | 45 | 11 |
| 208 | modPC 692.4/6.10 | 691.440 | 692.42 | 184.1 | 6.10 | modPC 692.4/6.10 | 100 | 10 | 45 | 11 |
| 209 | modPC 694.4/6.20 | 693.400 | 694.4 | 184.1 | 6.20 | modPC 694.4/6.20 | 100 | 10 | 45 | 11 |
| 210 | modPC 703.5/4.09 | 702.500 | 703.5 | 184.1 | 4.09 | modPC 703.5/4.09 | 100 | 10 | 45 | 11 |

TABLE 7-continued

Lipid analytes measured in MRM experiment 1

| # | Analyte | exact mass | Q1[a] | Q3[b] | tR[c] | ID[d] | DP[e] | EP[f] | CE[g] | CXP[h] |
|---|---------|------------|-------|-------|-------|-------|-------|-------|-------|--------|
| 211 | modPC 704.5/3.81 | 703.500 | 704.5 | 184.1 | 3.81 | modPC 704.5/3.81 | 100 | 10 | 45 | 11 |
| 212 | modPC 706.5/3.79 | 705.500 | 706.5 | 184.1 | 3.79 | modPC 706.5/3.79 | 100 | 10 | 45 | 11 |
| 213 | modPC 720.5/4.52 | 719.510 | 720.5 | 184.1 | 4.52 | modPC 720.5/4.52 | 100 | 10 | 45 | 11 |
| 214 | modPC 736.5/5.38 | 735.500 | 736.5 | 184.1 | 5.38 | modPC 736.5/5.38 | 100 | 10 | 45 | 11 |
| 215 | modPC 743.5/5.91 | 742.500 | 743.5 | 184.1 | 5.91 | modPC 743.5/5.91 | 100 | 10 | 45 | 11 |
| 216 | modPC 745.5/6.35 | 744.500 | 745.5 | 184.1 | 6.35 | modPC 745.5/6.35 | 100 | 10 | 45 | 11 |
| 217 | modPC 752.5/5.58 | 751.500 | 752.5 | 184.1 | 5.58 | modPC 752.5/5.58 | 100 | 10 | 45 | 11 |
| 218 | modPC 764.5/6.52 | 763.500 | 764.5 | 184.1 | 6.52 | modPC 764.5/6.52 | 100 | 10 | 45 | 11 |
| 219 | modPC 769.5/6.25 | 768.500 | 769.5 | 184.1 | 6.25 | modPC 769.5/6.25 | 100 | 10 | 45 | 11 |
| 220 | modPC 772.5/5.37 | 771.500 | 772.5 | 184.1 | 5.37 | modPC 772.5/5.37 | 100 | 10 | 45 | 11 |
| 221 | modPC 773.6/6.47 | 772.500 | 773.5 | 184.1 | 6.47 | modPC 773.6/6.47 | 100 | 10 | 45 | 11 |
| 222 | modPC 788.6/5.19 | 787.500 | 788.5 | 184.1 | 5.19 | modPC 788.6/5.19 | 100 | 10 | 45 | 11 |
| 223 | modPC 801.6/6.70 | 800.600 | 801.6 | 184.1 | 6.70 | modPC 801.6/6.70 | 100 | 10 | 45 | 11 |
| 224 | modPC 816.6/5.58 | 815.600 | 816.60 | 184.1 | 5.58 | modPC 816.6/5.58 | 100 | 10 | 45 | 11 |
| 225 | modPC 818.6/6.10 | 817.610 | 818.61 | 184.1 | 6.39 | modPC 818.6/6.10 | 100 | 10 | 45 | 11 |
| 226 | modPC 818.6/6.48 | 817.620 | 818.62 | 184.1 | 6.64 | modPC 818.6/6.48 | 100 | 10 | 45 | 11 |
| 227 | modPC 828.6/6.03 | 827.600 | 828.6 | 184.1 | 6.03 | modPC 828.6/6.03 | 100 | 10 | 45 | 11 |
| 228 | modPC 843.6/7.10 | 842.600 | 843.6 | 184.1 | 7.10 | modPC 843.6/7.10 | 100 | 10 | 45 | 11 |
| 229 | modPC 866.6/7.24 | 865.600 | 866.6 | 184.1 | 7.24 | modPC 866.6/7.24 | 100 | 10 | 45 | 11 |
| 230 | modPC 878.6/5.98 | 877.600 | 878.6 | 184.1 | 5.98 | modPC 878.6/5.98 | 100 | 10 | 45 | 11 |
| 231 | modPC 881.6/6.05 | 880.600 | 881.6 | 184.1 | 6.05 | modPC 881.6/6.05 | 100 | 10 | 45 | 11 |
| 232 | COH | 386.355 | 404.4 | 369.3 | 6.81 | COH | 55 | 10 | 17 | 12 |
| S14 | COH d7 (IS) | 393.399 | 411.4 | 376.3 | 6.80 | COH-d7 | 55 | 10 | 17 | 12 |
| 233 | CE 14:0 | 596.553 | 614.6 | 369.3 | 9.35 | C14:0 | 30 | 10 | 20 | 12 |
| 234 | CE 15:0 | 610.569 | 628.6 | 369.3 | 9.27 | C15:0 | 30 | 10 | 20 | 12 |
| 235 | CE 16:2 | 620.553 | 638.6 | 369.3 | 9.21 | C16:2 | 30 | 10 | 20 | 12 |
| 236 | CE 16:1 | 622.569 | 640.6 | 369.3 | 9.33 | C16:1 | 30 | 10 | 20 | 12 |
| 237 | CE 16:0 | 624.585 | 642.6 | 369.3 | 9.36 | C16:0 | 30 | 10 | 20 | 12 |
| 238 | CE 17:1 | 636.585 | 654.6 | 369.3 | 9.48 | C17:1 | 30 | 10 | 20 | 12 |
| 239 | CE 17:0 | 638.600 | 656.6 | 369.3 | 9.39 | C17:0 | 30 | 10 | 20 | 12 |
| 240 | CE 18:3 | 647.577 | 665.6 | 370.3 | 9.22 | C18:3 + 1 | 30 | 10 | 20 | 12 |
| 241 | CE 18:2 | 650.601 | 668.6 | 371.3 | 9.33 | C18:2 + 2 | 30 | 10 | 20 | 12 |
| 242 | CE 18:1 | 651.608 | 669.6 | 370.3 | 9.46 | C18:1 + 1 | 30 | 10 | 20 | 12 |
| 243 | CE 18:0 | 652.616 | 670.6 | 369.3 | 9.60 | C18:0 | 30 | 10 | 20 | 12 |
| S15 | CE 18:0 d6 (IS) | 658.653 | 676.7 | 375.3 | 9.85 | C18:0 d6 (IS) | 30 | 10 | 20 | 12 |
| S15 | CE 18:0 d6 (IS) | 659.661 | 677.7 | 376.3 | 9.85 | C18:0 d6 + 1 (IS) | 30 | 10 | 20 | 12 |
| S15 | CE 18:0 d6 (IS) | 660.669 | 678.7 | 377.3 | 9.85 | C18:0 d6 + 2 (IS) | 30 | 10 | 20 | 12 |
| 244 | CE 20:5 | 672.585 | 690.6 | 371.3 | 9.13 | C20:5 + 2 | 30 | 10 | 20 | 12 |
| 245 | CE 20:4 | 674.601 | 692.6 | 371.3 | 9.24 | C20:4 + 2 | 30 | 10 | 20 | 12 |
| 246 | CE 20:3 | 674.600 | 692.6 | 369.3 | 9.34 | C20:3 | 30 | 10 | 20 | 12 |
| 247 | CE 20:2 | 676.616 | 694.6 | 369.3 | 9.31 | C20:2 | 30 | 10 | 20 | 12 |
| 248 | CE 20:1 | 678.631 | 696.7 | 369.3 | 9.42 | C20:1 | 30 | 10 | 20 | 12 |
| 249 | CE 22:6 | 682.663 | 700.7 | 371.3 | 9.18 | C22:6 + 2 | 30 | 10 | 20 | 12 |
| 250 | CE 22:5 | 696.585 | 714.6 | 369.3 | 9.25 | C22:5 | 30 | 10 | 20 | 12 |
| 251 | CE 22:4 | 698.600 | 716.6 | 369.3 | 9.39 | C22:4 | 30 | 10 | 20 | 12 |
| 252 | CE 22:3 | 700.616 | 718.6 | 369.3 | 9.32 | C22:3 | 30 | 10 | 20 | 12 |
| 253 | CE 22:2 | 702.631 | 720.7 | 369.3 | 9.42 | C22:2 | 30 | 10 | 20 | 12 |
| 254 | CE 22:1 | 704.647 | 722.7 | 369.3 | 9.54 | C22:1 | 30 | 10 | 20 | 12 |
| 255 | CE 22:0 | 706.663 | 724.7 | 369.3 | 9.68 | C22:0 | 30 | 10 | 20 | 12 |
| 256 | CE 24:6 | 708.678 | 726.7 | 369.3 | 9.12 | C24:6 | 30 | 10 | 20 | 12 |
| 257 | CE 24:5 | 724.616 | 742.6 | 369.3 | 9.22 | C24:5 | 30 | 10 | 20 | 12 |
| 258 | CE 24:4 | 726.631 | 744.7 | 369.3 | 9.33 | C24:4 | 30 | 10 | 20 | 12 |
| 259 | CE 24:3 | 728.647 | 746.7 | 369.3 | 9.43 | C24:3 | 30 | 10 | 20 | 12 |
| 260 | CE 24:2 | 730.663 | 748.7 | 369.3 | 9.53 | C24:2 | 30 | 10 | 20 | 12 |
| 261 | CE 24:1 | 732.678 | 750.7 | 369.3 | 9.64 | C24:1 | 30 | 10 | 20 | 12 |
| 262 | CE 24:0 | 734.694 | 752.7 | 369.3 | 9.78 | C24:0 | 30 | 10 | 20 | 12 |
| 263 | modCE 558.5/7.74 | 557.510 | 558.5 | 369.3 | 7.74 | modCE 558.5/7.74 | 55 | 10 | 20 | 12 |
| 264 | modCE 588.5/7.94 | 587.500 | 588.5 | 369.3 | 7.94 | modCE 588.5/7.94 | 55 | 10 | 20 | 12 |
| 265 | modCE 682.7/8.76 | 681.700 | 682.7 | 369.3 | 8.76 | modCE 682.7/8.76 | 55 | 10 | 20 | 12 |
| 266 | modCE 790.8/6.57 | 789.800 | 790.8 | 369.3 | 6.57 | modCE 790.8/6.57 | 55 | 10 | 20 | 12 |

[a] Q1, m/z setting for quardupole 1
[b] Q2, m/z setting for quardupole 2
[c] tR, retention time
[d] ID, analyte identity (+1) and (+2) designate the isotope species
[e] DP, declustering potential
[f] EP, entrance potential
[g] CE, collision energy
[f] CXP, cell exit potential

TABLE 8

Lipid analytes measured in MRM experiment 2

| # | Analyte | exact mass | Q1[a] | Q3[b] | tR[c] | ID[d] | DP[e] | EP[f] | CE[g] | CXP[h] |
|---|---|---|---|---|---|---|---|---|---|---|
| 267 | DG 14:0 14:0 | 512.444 | 530.5 | 285.2 | 1.90 | DG 14:0 14:0 | 55 | 10 | 30 | 22 |
| 268 | DG 14:1 16:0 | 538.465 | 556.5 | 313.3 | 1.90 | DG 14:1 16:0 | 55 | 10 | 30 | 22 |
| 269 | DG 14:0 16:0 | 540.475 | 558.5 | 313.3 | 2.00 | DG 14:0 16:0 | 55 | 10 | 30 | 22 |
| S16 | DG 15:0 15:0 (IS) | 540.475 | 558.5 | 299.3 | 2.10 | DG 15:0 15:0 (IS) | 55 | 10 | 30 | 22 |
| 270 | DG 14:0 18:2 | 564.475 | 582.5 | 285.2 | 1.90 | DG 14:0 18:2 | 55 | 10 | 30 | 22 |
| 271 | DG 14:0 18:1 | 566.491 | 584.5 | 285.2 | 2.00 | DG 14:0 18:1 | 55 | 10 | 30 | 22 |
| 272 | DG 16:0 16:0 | 568.507 | 586.5 | 313.3 | 2.10 | DG 16:0 16:0 | 55 | 10 | 30 | 22 |
| 273 | DG 16:0 18:2 | 592.507 | 610.5 | 313.3 | 2.10 | DG 16:0 18:2 | 55 | 10 | 30 | 22 |
| 274 | DG 16:1 18:1 | 592.507 | 610.5 | 339.3 | 2.00 | DG 16:1 18:1 | 55 | 10 | 30 | 22 |
| 275 | DG 16:0 18:1 | 594.522 | 612.6 | 339.3 | 2.10 | DG 16:0 18:1 | 55 | 10 | 30 | 22 |
| 276 | DG 18:0 16:1 | 594.522 | 612.6 | 311.3 | 2.10 | DG 18:0 16:1 | 55 | 10 | 30 | 22 |
| 277 | DG 16:0 18:0 | 596.538 | 614.6 | 341.3 | 2.20 | DG 16:0 18:0 | 55 | 10 | 30 | 22 |
| 278 | DG 16:0 20:4 | 616.507 | 634.5 | 313.3 | 2.00 | DG 16:0 20:4 | 55 | 10 | 30 | 22 |
| 279 | DG 18:1 18:3 | 616.507 | 634.5 | 339.3 | 2.00 | DG 18:1 18:3 | 55 | 10 | 30 | 22 |
| 280 | DG 18:2 18:2 | 616.507 | 634.5 | 337.3 | 2.00 | DG 18:2 18:2 | 55 | 10 | 30 | 22 |
| 281 | DG 16:0 20:3 | 618.522 | 636.6 | 313.3 | 2.10 | DG 16:0 20:3 | 55 | 10 | 30 | 22 |
| 282 | DG 18:1 18:2 | 618.522 | 636.6 | 339.3 | 2.00 | DG 18:1 18:2 | 55 | 10 | 30 | 22 |
| 283 | DG 18:0 18:2 | 620.538 | 638.6 | 341.3 | 2.10 | DG 18:0 18:2 | 55 | 10 | 30 | 22 |
| 284 | DG 18:1 18:1 | 620.538 | 638.6 | 339.3 | 2.10 | DG 18:1 18:1 | 55 | 10 | 30 | 22 |
| 285 | DG 18:0 18:1 | 622.554 | 640.6 | 339.3 | 2.20 | DG 18:0 18:1 | 55 | 10 | 30 | 22 |
| 286 | DG 16:0 20:0 | 624.569 | 642.6 | 313.3 | 2.30 | DG 16:0 20:0 | 55 | 10 | 30 | 22 |
| 287 | DG 18:0 18:0 | 624.569 | 642.6 | 341.3 | 2.40 | DG 18:0 18:0 | 55 | 10 | 30 | 22 |
| 288 | DG 16:0 22:6 | 640.507 | 658.5 | 313.3 | 2.00 | DG 16:0 22:6 | 55 | 10 | 30 | 22 |
| 289 | DG 16:0 22:5 | 642.522 | 660.6 | 313.3 | 2.00 | DG 16:0 22:5 | 55 | 10 | 30 | 22 |
| 290 | DG 18:1 20:4 | 642.522 | 660.6 | 339.3 | 2.00 | DG 18:1 20:4 | 55 | 10 | 30 | 22 |
| 291 | DG 18:0 20:4 | 644.538 | 662.6 | 341.3 | 2.10 | DG 18:0 20:4 | 55 | 10 | 30 | 22 |
| 292 | DG 18:1 20:3 | 644.538 | 662.6 | 339.3 | 2.10 | DG 18:1 20:3 | 55 | 10 | 30 | 22 |
| 293 | DG 18:1 20:0 | 650.585 | 668.6 | 369.3 | 2.20 | DG 18:1 20:0 | 55 | 10 | 30 | 22 |
| 294 | TG 14:0 16:1 18:2 | 800.736 | 818.8 | 521.5 | 3.26 | TG 14:0 16:1 18:2 | 95 | 10 | 30 | 12 |
| 295 | TG 16:1 16:1 16:1 | 800.736 | 818.8 | 547.5 | 3.18 | TG 16:1 16:1 16:1 | 95 | 10 | 30 | 12 |
| 296 | TG 14:0 16:0 18:2 | 802.736 | 820.8 | 547.5 | 3.47 | TG 14:0 16:0 18:2 | 95 | 10 | 30 | 12 |
| 297 | TG 14:0 16:1 18:1 | 802.736 | 820.8 | 521.5 | 3.46 | TG 14:0 16:1 18:1 | 95 | 10 | 30 | 12 |
| 298 | TG 14:1 16:0 18:1 | 802.736 | 820.8 | 577.6 | 3.46 | TG 14:1 16:0 18:1 | 95 | 10 | 30 | 12 |
| 299 | TG 14:1 16:1 18:0 | 802.736 | 820.8 | 549.5 | 3.46 | TG 14:1 16:1 18:0 | 95 | 10 | 30 | 12 |
| 300 | TG 18:1 14:0 16:0 | 804.736 | 822.8 | 523.5 | 3.77 | TG 18:1 14:0 16:0 | 95 | 10 | 30 | 12 |
| 301 | TG 16:0 16:0 16:0 | 806.736 | 824.8 | 551.5 | 4.17 | TG 16:0 16:0 16:0 | 95 | 10 | 30 | 12 |
| 302 | TG 15:0 18:1 16:0 | 818.752 | 836.8 | 577.5 | 3.79 | TG 15:0 18:1 16:0 | 95 | 10 | 30 | 12 |
| 303 | TG 17:0 16:0 16:1 | 818.752 | 836.8 | 563.5 | 3.92 | TG 17:0 16:0 16:1 | 95 | 10 | 30 | 12 |
| 304 | TG 17:0 18:1 14:0 | 818.752 | 836.8 | 537.5 | 3.96 | TG 17:0 18:1 14:0 | 95 | 10 | 30 | 12 |
| 305 | TG 14:0 18:2 18:2 | 826.747 | 844.8 | 599.5 | 3.23 | TG 14:0 18:2 18:2 | 95 | 10 | 30 | 12 |
| 306 | TG 14:1 18:0 18:2 | 828.767 | 846.8 | 603.6 | 3.46 | TG 14:1 18:0 18:2 | 95 | 10 | 30 | 12 |
| 307 | TG 14:1 18:1 18:1 | 828.767 | 846.8 | 547.5 | 3.43 | TG 14:1 18:1 18:1 | 95 | 10 | 30 | 12 |
| 308 | TG 16:1 16:1 18:1 | 828.767 | 847.8 | 576.6 | 3.43 | TG 16:1 16:1 18:1 +1 | 95 | 10 | 30 | 12 |
| 309 | TG 16:0 16:0 18:2 | 830.767 | 848.8 | 551.5 | 3.82 | TG 16:0 16:0 18:2 | 95 | 10 | 30 | 12 |
| 310 | TG 16:1 16:1 18:0 | 830.767 | 848.8 | 547.5 | 3.78 | TG 16:1 16:1 18:0 | 95 | 10 | 30 | 12 |
| 311 | TG 16:0 16:1 18:1 | 830.767 | 849.8 | 550.5 | 3.75 | TG 16:0 16:1 18:1 +1 | 95 | 10 | 30 | 12 |
| 312 | TG 14:0 18:0 18:1 | 832.767 | 850.8 | 605.6 | 4.06 | TG 14:0 18:0 18:1 | 95 | 10 | 30 | 12 |
| 313 | TG 16:0 16:0 18:1 | 832.767 | 851.8 | 552.5 | 4.12 | TG 16:0 16:0 18:1 | 95 | 10 | 30 | 12 |
| 314 | TG 16:0 16:0 18:0 | 834.767 | 852.8 | 551.5 | 4.12 | TG 16:0 16:0 18:0 | 95 | 10 | 30 | 12 |
| 315 | TG 15:0 18:1 18:1 | 844.783 | 862.8 | 603.6 | 3.90 | TG 15:0 18:1 18:1 | 95 | 10 | 30 | 12 |
| 316 | TG 17:0 18:1 16:1 | 844.783 | 862.8 | 563.5 | 3.89 | TG 17:0 18:1 16:1 | 95 | 10 | 30 | 12 |
| 317 | TG 17:0 18:2 16:0 | 844.783 | 862.8 | 589.6 | 3.92 | TG 17:0 18:2 16:0 | 95 | 10 | 30 | 12 |
| 318 | TG 17:0 18:1 16:0 | 846.783 | 864.8 | 565.5 | 4.33 | TG 17:0 18:1 16:0 | 95 | 10 | 30 | 12 |
| 319 | TG 17:0 16:0 18:0 | 848.783 | 866.8 | 593.6 | 4.28 | TG 17:0 16:0 18:0 | 95 | 10 | 30 | 12 |
| S17 | TG 17:0 17:0 17:0 (IS) | 848.783 | 866.8 | 579.5 | 4.77 | TG 17:0 17:0 17:0 (IS) | 95 | 10 | 30 | 12 |
| S17 | TG 17:0 17:0 17:0 (IS) | 848.783 | 867.8 | 580.5 | 4.77 | TG 17:0 17:0 17:0 (IS) | 95 | 10 | 30 | 12 |
| 320 | TG 16:0 18:2 18:2 | 854.798 | 872.8 | 599.6 | 3.58 | TG 16:0 18:2 18:2 | 95 | 10 | 30 | 12 |
| 321 | TG 16:1 18:1 18:2 | 854.798 | 872.8 | 573.6 | 3.45 | TG 16:1 18:1 18:2 | 95 | 10 | 30 | 12 |
| 322 | TG 16:1 18:1 18:1 | 856.798 | 874.8 | 603.6 | 3.70 | TG 16:1 18:1 18:1 | 95 | 10 | 30 | 12 |
| 323 | TG 16:0 18:1 18:2 | 856.798 | 875.8 | 578.6 | 3.80 | TG 16:0 18:1 18:2 +1 | 95 | 10 | 30 | 12 |
| 324 | TG 16:0 18:1 18:1 | 858.798 | 877.8 | 604.6 | 4.06 | TG 16:0 18:1 18:1 +1 | 95 | 10 | 30 | 12 |
| 325 | TG 16:0 18:0 18:1 | 860.798 | 878.8 | 577.5 | 4.05 | TG 16:0 18:0 18:1 | 95 | 10 | 30 | 12 |
| 326 | TG 17:0 18:1 18:1 | 872.814 | 890.8 | 603.6 | 4.03 | TG 17:0 18:1 18:1 | 95 | 10 | 30 | 12 |
| 327 | TG 18:2 18:2 18:2 | 878.830 | 896.9 | 599.6 | 3.29 | TG 18:2 18:2 18:2 | 95 | 10 | 30 | 12 |
| 328 | TG 18:1 18:2 18:2 | 880.830 | 898.9 | 599.6 | 3.49 | TG 18:1 18:2 18:2 | 95 | 10 | 30 | 12 |
| 329 | TG 18:0 18:2 18:2 | 882.803 | 900.8 | 599.5 | 3.56 | TG 18:0 18:2 18:2 | 95 | 10 | 30 | 12 |
| 330 | TG 18:1 18:1 18:2 | 882.830 | 900.9 | 603.9 | 3.73 | TG 18:1 18:1 18:2 | 95 | 10 | 30 | 12 |
| 331 | TG 18:1 18:1 18:1 | 884.830 | 903.9 | 604.6 | 4.02 | TG 18:1 18:1 18:1 +1 | 95 | 10 | 30 | 12 |
| 332 | TG 18:0 18:1 18:1 | 886.830 | 904.9 | 603.6 | 4.02 | TG 18:0 18:1 18:1 | 95 | 10 | 30 | 12 |
| 333 | TG 18:0 18:0 18:1 | 888.830 | 906.9 | 607.6 | 4.37 | TG 18:0 18:0 18:1 | 95 | 10 | 30 | 12 |
| 334 | TG 18:0 18:0 18:0 | 890.830 | 908.9 | 607.6 | 4.90 | TG 18:0 18:0 18:0 | 95 | 10 | 30 | 12 |
| 335 | TG 18:2 18:2 20:4 | 902.861 | 920.9 | 599.6 | 3.29 | TG 18:2 18:2 20:4 | 95 | 10 | 30 | 12 |

TABLE 8-continued

Lipid analytes measured in MRM experiment 2

| # | Analyte | exact mass | Q1[a] | Q3[b] | tR[c] | ID[d] | DP[e] | EP[f] | CE[g] | CXP[h] |
|---|---|---|---|---|---|---|---|---|---|---|
| 336 | TG 18:1 18:1 20:4 | 906.861 | 924.9 | 603.6 | 3.60 | TG 18:1 18:1 20:4 | 95 | 10 | 30 | 12 |
| 337 | TG 18:1 18:1 22:6 | 930.892 | 948.9 | 603.7 | 3.42 | TG 18:1 18:1 22:6 | 95 | 10 | 30 | 12 |

[a]Q1, m/z setting for quardupole 1
[b]Q2, m/z setting for quardupole 2
[c]tR, retention time
[d]ID, analyte identity (+1) and (+2) designate the isotope species
[e]DP, declustering potential
[f]EP, entrance potential
[g]CE, collision energy
[j]CXP, cell exit potential

TABLE 9

Lipid analyte levels[a] in stable and unstable cohorts

| # | Analyte | stable (median) | unstable (median) | stable/unstable | Mann-Whitney U | Asymp. Sig. (2-tailed) |
|---|---|---|---|---|---|---|
| 1 | Cer 16:0 | 388 | 400 | 1.03 | 2370 | 5.66E−01 |
| 2 | Cer 18:1 | 203 | 212 | 1.04 | 1921 | 1.62E−02 |
| 3 | Cer 18:0 | 170 | 196 | 1.15 | 1857 | 7.72E−03 |
| 4 | Cer 20:0 | 139 | 148 | 1.07 | 2305 | 4.01E−01 |
| 5 | Cer 22:0 | 794 | 761 | 0.96 | 2454 | 8.16E−01 |
| 6 | Cer 24:1 | 1233 | 1207 | 0.98 | 2409 | 6.78E−01 |
| 7 | Cer 24:0 | 2647 | 2332 | 0.88 | 2364.5 | 5.51E−01 |
| 8 | MHC 16:0 | 1756 | 1734 | 0.99 | 2372 | 5.71E−01 |
| 9 | MHC 18:1 | 53 | 61 | 1.15 | 2275.5 | 3.37E−01 |
| 10 | MHC 18:0 | 351 | 366 | 1.04 | 2403.5 | 6.61E−01 |
| 11 | MHC 20:0 | 505 | 440 | 0.87 | 2143 | 1.34E−01 |
| 12 | MHC 22:0 | 3490 | 3239 | 0.93 | 2400.5 | 6.53E−01 |
| 13 | MHC 24:1 | 4547 | 4066 | 0.89 | 2386 | 6.11E−01 |
| 14 | MHC 24:0 | 5646 | 4785 | 0.85 | 2248.5 | 2.85E−01 |
| 15 | DHC 16:0 | 8510 | 8786 | 1.03 | 2096.5 | 9.13E−02 |
| 16 | DHC 18:1 | 61 | 76 | 1.24 | 1844 | 6.59E−03 |
| 17 | DHC 18:0 | 141 | 145 | 1.03 | 2358 | 5.33E−01 |
| 18 | DHC 20:0 | 104 | 113 | 1.09 | 2380 | 5.94E−01 |
| 19 | DHC 22:0 | 593 | 640 | 1.08 | 2274 | 3.34E−01 |
| 20 | DHC 24:1 | 2169 | 2268 | 1.05 | 2247 | 2.82E−01 |
| 21 | DHC 24:0 | 585 | 637 | 1.09 | 2466 | 8.55E−01 |
| 22 | THC 16:0 | 1516 | 1472 | 0.97 | 2300 | 3.90E−01 |
| 23 | THC 18:1 | 166 | 162 | 0.98 | 2487 | 9.22E−01 |
| 24 | THC 18:0 | 172 | 159 | 0.93 | 2202.5 | 2.09E−01 |
| 25 | THC 20:0 | 67 | 64 | 0.96 | 2400.5 | 6.53E−01 |
| 26 | THC 22:0 | 247 | 270 | 1.09 | 2337 | 4.78E−01 |
| 27 | THC 24:1 | 617 | 614 | 0.99 | 2452.5 | 8.12E−01 |
| 28 | THC 24:0 | 310 | 322 | 1.04 | 2284.5 | 3.56E−01 |
| 29 | GM3 16:0 | 1443 | 1509 | 1.05 | 2439.5 | 7.71E−01 |
| 30 | GM3 18:0 | 500 | 453 | 0.90 | 2022 | 4.64E−02 |
| 31 | GM3 20:0 | 333 | 325 | 0.98 | 2324 | 4.46E−01 |
| 32 | GM3 22:0 | 713 | 725 | 1.02 | 2472 | 8.74E−01 |
| 33 | GM3 24:1 | 1103 | 1037 | 0.94 | 2291.5 | 3.71E−01 |
| 34 | GM3 24:0 | 641 | 638 | 1.00 | 2467 | 8.58E−01 |
| 35 | modCer 576.5/7.68 | 21 | 22 | 1.06 | 2275 | 3.36E−01 |
| 36 | modCer 614.6/5.72 | 20 | 22 | 1.09 | 2052 | 6.15E−02 |
| 37 | modCer 632.6/9.22 | 4 | 4 | 1.04 | 2503 | 9.74E−01 |
| 38 | modCer 651.6/7.56 | 288 | 262 | 0.91 | 2330 | 4.61E−01 |
| 39 | modCer 703.6/5.87 | 651 | 626 | 0.96 | 2451.5 | 8.08E−01 |
| 40 | modCer 731.6/6.22 | 45 | 56 | 1.24 | 1533 | 6.78E−05 |
| 41 | modCer 766.6/7.17 | 24 | 22 | 0.90 | 2275 | 3.36E−01 |
| 42 | modCer 769.6/8.01 | 158 | 142 | 0.90 | 2334 | 4.71E−01 |
| 43 | modCer 798.7/7.29 | 142 | 134 | 0.94 | 2312 | 4.18E−01 |
| 44 | modCer 875.7/9.23 | 354 | 395 | 1.12 | 1993 | 3.49E−02 |
| 45 | modCer 883.8/7.75 | 77 | 83 | 1.07 | 2420 | 7.11E−01 |
| 46 | modCer 886.8/9.06 | 48 | 49 | 1.03 | 2156 | 1.48E−01 |
| 47 | modCer 910.8/8.98 | 36 | 40 | 1.10 | 2027 | 4.87E−02 |
| 48 | modCer 921.8/9.05 | 84 | 82 | 0.98 | 2450.5 | 8.05E−01 |
| 49 | SM 14:0 | 12650 | 12696 | 1.00 | 2464 | 8.48E−01 |
| 50 | SM 15:0 | 7961 | 8841 | 1.11 | 2205.5 | 2.13E−01 |
| 51 | SM 16:1 | 18788 | 20000 | 1.06 | 2231 | 2.54E−01 |
| 52 | SM 16:0 | 108207 | 114439 | 1.06 | 2214.5 | 2.27E−01 |
| 53 | SM 18:1 | 14013 | 16230 | 1.16 | 1761 | 2.25E−03 |
| 54 | SM 18:0 | 26090 | 30897 | 1.18 | 1543 | 8.04E−05 |
| 55 | SM 20:1 | 8941 | 9374 | 1.05 | 2490 | 9.32E−01 |
| 56 | SM 22:1 | 15073 | 15742 | 1.04 | 2171 | 1.66E−01 |

TABLE 9-continued

Lipid analyte levels$^a$ in stable and unstable cohorts

| # | Analyte | stable (median) | unstable (median) | stable/unstable | Mann-Whitney U | Asymp. Sig. (2-tailed) |
|---|---|---|---|---|---|---|
| 57 | SM 22:0 | 26334 | 27440 | 1.04 | 2129 | 1.20E−01 |
| 58 | SM 24:2 | 52283 | 52810 | 1.01 | 2333 | 4.68E−01 |
| 59 | SM 24:1 | 67438 | 66486 | 0.99 | 2432.5 | 7.49E−01 |
| 60 | SM 24:0 | 17117 | 17197 | 1.00 | 2386 | 6.11E−01 |
| 61 | PG 16:1 18:1 | 6 | 5 | 0.90 | 2401.5 | 6.56E−01 |
| 62 | PG 16:0 18:1 | 68 | 63 | 0.93 | 2250 | 2.88E−01 |
| 63 | PG 18:1 18:1 | 111 | 100 | 0.90 | 2110.5 | 1.03E−01 |
| 64 | PG 18:0 18:1 | 66 | 63 | 0.96 | 2236 | 2.63E−01 |
| 65 | BMP 18:1 18:1 | 31 | 34 | 1.11 | 2266 | 3.18E−01 |
| 66 | PS 36:2 | 138 | 147 | 1.06 | 2330 | 4.61E−01 |
| 67 | PS 36:1 | 876 | 926 | 1.06 | 2419 | 7.08E−01 |
| 68 | PS 38:5 | 50 | 51 | 1.03 | 2345 | 4.99E−01 |
| 69 | PS 38:4 | 844 | 981 | 1.16 | 2295 | 3.79E−01 |
| 70 | PS 38:3 | 182 | 191 | 1.05 | 2426 | 7.29E−01 |
| 71 | PS 40:6 | 101 | 96 | 0.96 | 2286 | 3.59E−01 |
| 72 | PS 40:5 | 89 | 95 | 1.07 | 2385 | 6.08E−01 |
| 73 | PE 32:1 | 119 | 111 | 0.93 | 2272 | 3.30E−01 |
| 74 | PE 32:0 | 52 | 55 | 1.05 | 2208.5 | 2.18E−01 |
| 75 | PE 34:2 | 1505 | 1746 | 1.16 | 2362 | 5.44E−01 |
| 76 | PE 34:1 | 1092 | 1305 | 1.20 | 2162 | 1.55E−01 |
| 77 | PE 36:5 | 221 | 186 | 0.84 | 2014.5 | 4.31E−02 |
| 78 | PE 36:4 | 2409 | 2253 | 0.94 | 2418 | 7.05E−01 |
| 79 | PE 36:3 | 974 | 1034 | 1.06 | 2290 | 3.68E−01 |
| 80 | PE 36:2 | 3848 | 3741 | 0.97 | 2290 | 3.68E−01 |
| 81 | PE 36:1 | 842 | 826 | 0.98 | 2374 | 5.77E−01 |
| 82 | PE 36:0 | 22 | 21 | 0.95 | 2485 | 9.16E−01 |
| 83 | PE 38:6 | 2582 | 2994 | 1.16 | 2240 | 2.70E−01 |
| 84 | PE 38:5 | 1890 | 1834 | 0.97 | 2481 | 9.03E−01 |
| 85 | PE 38:4 | 4774 | 5155 | 1.08 | 2304 | 3.99E−01 |
| 86 | PE 38:3 | 540 | 521 | 0.96 | 2392 | 6.28E−01 |
| 87 | PE 38:2 | 90 | 98 | 1.10 | 2333 | 4.68E−01 |
| 88 | PE 38:1 | 49 | 54 | 1.09 | 2357.5 | 5.32E−01 |
| 89 | PE 40:7 | 227 | 225 | 0.99 | 2451 | 8.07E−01 |
| 90 | PE 40:6 | 1359 | 1515 | 1.11 | 2296 | 3.81E−01 |
| 91 | PI 32:1 | 238 | 196 | 0.82 | 1987.5 | 3.30E−02 |
| 92 | PI 32:0 | 88 | 71 | 0.81 | 2052 | 6.15E−02 |
| 93 | PI 34:1 | 1815 | 1361 | 0.75 | 1840 | 6.27E−03 |
| 94 | PI 34:0 | 36 | 29 | 0.80 | 1832 | 5.68E−03 |
| 95 | PI 36:4 | 1355 | 1234 | 0.91 | 1831.5 | 5.64E−03 |
| 96 | PI 36:3 | 1196 | 915 | 0.77 | 1612 | 2.50E−04 |
| 97 | PI 36:2 | 5407 | 5396 | 1.00 | 2499 | 9.61E−01 |
| 98 | PI 36:1 | 1572 | 1165 | 0.74 | 1588 | 1.70E−04 |
| 99 | PI 36:0 | 6 | 6 | 0.95 | 2164 | 1.58E−01 |
| 100 | PI 38:6 | 231 | 203 | 0.88 | 2008 | 4.05E−02 |
| 101 | PI 38:5 | 878 | 760 | 0.87 | 1802 | 3.88E−03 |
| 102 | PI 38:4 | 11667 | 10321 | 0.88 | 2124 | 1.15E−01 |
| 103 | PI 38:3 | 2445 | 2078 | 0.85 | 1990 | 3.38E−02 |
| 104 | PI 38:2 | 169 | 126 | 0.75 | 1718 | 1.24E−03 |
| 105 | PI 40:6 | 544 | 503 | 0.92 | 2151 | 1.43E−01 |
| 106 | PI 40:5 | 572 | 508 | 0.89 | 2205 | 2.13E−01 |
| 107 | PI 40:4 | 153 | 136 | 0.89 | 1916 | 1.54E−02 |
| 108 | LPC 14:0 | 1606 | 1082 | 0.67 | 1428 | 1.03E−05 |
| 109 | LPC 15:0 | 1028 | 911 | 0.89 | 2227.5 | 2.48E−01 |
| 110 | LPC 16:1 | 3754 | 3022 | 0.81 | 1581 | 1.52E−04 |
| 111 | LPC 16:0 | 63869 | 62301 | 0.98 | 2319 | 4.34E−01 |
| 112 | LPC 18:2 | 26381 | 20565 | 0.78 | 1758 | 2.16E−03 |
| 113 | LPC 18:1 | 23188 | 18279 | 0.79 | 1611.5 | 2.48E−04 |
| 114 | LPC 18:0 | 20232 | 19420 | 0.96 | 2314 | 4.22E−01 |
| 115 | LPC 20:5 | 1599 | 1333 | 0.83 | 1895 | 1.21E−02 |
| 116 | LPC 20:4 | 7636 | 7843 | 1.03 | 2414.5 | 6.94E−01 |
| 117 | LPC 20:3 | 3237 | 2916 | 0.90 | 1959.5 | 2.47E−02 |
| 118 | LPC 20:2 | 325 | 280 | 0.86 | 1866 | 8.60E−03 |
| 119 | LPC 20:1 | 227 | 230 | 1.01 | 2407 | 6.72E−01 |
| 120 | LPC 20:0 | 97 | 83 | 0.86 | 2016 | 4.38E−02 |
| 121 | LPC 22:6 | 2689 | 2520 | 0.94 | 2507 | 9.87E−01 |
| 122 | LPAF 16:0 | 453 | 421 | 0.93 | 2196 | 1.99E−01 |
| 123 | LPAF 18:1 | 325 | 336 | 1.03 | 2491 | 9.35E−01 |
| 124 | LPAF 18:0 | 113 | 111 | 0.98 | 2436.5 | 7.62E−01 |
| 125 | PC 30:2 | 5779 | 6472 | 1.12 | 2160 | 1.53E−01 |
| 126 | PC 32:2 | 10897 | 10519 | 0.97 | 2252 | 2.91E−01 |
| 127 | PC 32:1 | 173997 | 160377 | 0.92 | 2244.5 | 2.78E−01 |
| 128 | PC 32:0 | 12453 | 12478 | 1.00 | 2399.5 | 6.50E−01 |
| 129 | PC 34:3 | 24565 | 19297 | 0.79 | 1673 | 6.41E−04 |
| 130 | PC 34:2 | 257882 | 250685 | 0.97 | 2329 | 4.58E−01 |
| 131 | PC 34:1 | 156440 | 154331 | 0.99 | 2322 | 4.41E−01 |
| 132 | PC 34:0 | 4083 | 3782 | 0.93 | 2094 | 8.94E−02 |

TABLE 9-continued

Lipid analyte levels[a] in stable and unstable cohorts

| # | Analyte | stable (median) | unstable (median) | stable/unstable | Mann-Whitney U | Asymp. Sig. (2-tailed) |
|---|---|---|---|---|---|---|
| 133 | PC 36:5 | 42661 | 34479 | 0.81 | 2013.5 | 4.27E-02 |
| 134 | PC 36:4 | 115623 | 118023 | 1.02 | 2429.5 | 7.40E-01 |
| 135 | PC 36:3 | 119722 | 113636 | 0.95 | 2080.5 | 7.95E-02 |
| 136 | PC 36:2 | 202275 | 182018 | 0.90 | 1986 | 3.25E-02 |
| 137 | PC 38:6 | 53779 | 55364 | 1.03 | 2351 | 5.15E-01 |
| 138 | PC 38:5 | 57321 | 56032 | 0.98 | 2483.5 | 9.11E-01 |
| 139 | PC 38:4 | 99515 | 93722 | 0.94 | 2502 | 9.71E-01 |
| 140 | PC 40:7 | 4389 | 4527 | 1.03 | 2485 | 9.16E-01 |
| 141 | PC 40:6 | 26276 | 28390 | 1.08 | 2225 | 2.44E-01 |
| 142 | PC 40:5 | 16485 | 17300 | 1.05 | 2420 | 7.11E-01 |
| 143 | PC 44:12 | 1865 | 1862 | 1.00 | 2453 | 8.13E-01 |
| 144 | oddPC 31:1 | 2474 | 2671 | 1.08 | 2193 | 1.95E-01 |
| 145 | oddPC 31:0 | 1354 | 1132 | 0.84 | 1970 | 2.75E-02 |
| 146 | oddPC 33:0 | 1958 | 1895 | 0.97 | 2359.5 | 5.37E-01 |
| 147 | oddPC 33:1 | 5456 | 5000 | 0.92 | 2044 | 5.71E-02 |
| 148 | oddPC 33:2 | 4922 | 4848 | 0.99 | 2495 | 9.48E-01 |
| 149 | oddPC 35:4 | 2077 | 2232 | 1.07 | 2460.5 | 8.37E-01 |
| 150 | oddPC 35:3 | 2365 | 2098 | 0.89 | 1886.5 | 1.10E-02 |
| 151 | oddPC 35:2 | 10642 | 10938 | 1.03 | 2478 | 8.93E-01 |
| 152 | oddPC 35:1 | 9601 | 9814 | 1.02 | 2382 | 5.99E-01 |
| 153 | oddPC 35:0 | 428 | 383 | 0.89 | 2022 | 4.64E-02 |
| 154 | oddPC 37:6 | 1040 | 1050 | 1.01 | 2399.5 | 6.50E-01 |
| 155 | oddPC 37:5 | 1925 | 1549 | 0.80 | 2143 | 1.34E-01 |
| 156 | oddPC 37:4 | 7032 | 7012 | 1.00 | 2250.5 | 2.89E-01 |
| 157 | oddPC 37:3 | 5051 | 4875 | 0.97 | 2382 | 5.99E-01 |
| 158 | oddPC 37:2 | 7640 | 8107 | 1.06 | 2402.5 | 6.59E-01 |
| 159 | APC 32:1 | 487 | 478 | 0.98 | 2353 | 5.20E-01 |
| 160 | APC 32:0 | 2060 | 2130 | 1.03 | 2374 | 5.77E-01 |
| 161 | APC 34:2 | 3121 | 2567 | 0.82 | 1789 | 3.27E-03 |
| 162 | APC 34:1 | 4539 | 4636 | 1.02 | 2478.5 | 8.95E-01 |
| 163 | APC 34:0 | 617 | 682 | 1.11 | 2357.5 | 5.32E-01 |
| 164 | APC 36:5 | 7280 | 7273 | 1.00 | 2244 | 2.77E-01 |
| 165 | APC 36:4 | 10625 | 10287 | 0.97 | 2154 | 1.46E-01 |
| 166 | APC 36:3 | 4020 | 3839 | 0.96 | 2129 | 1.20E-01 |
| 167 | APC 36:2 | 2421 | 2460 | 1.02 | 2271 | 3.28E-01 |
| 168 | APC 36:1 | 1134 | 1168 | 1.03 | 2496.5 | 9.53E-01 |
| 169 | APC 36:0 | 108 | 112 | 1.04 | 2426.5 | 7.31E-01 |
| 170 | APC 38:6 | 4055 | 3832 | 0.94 | 2106 | 9.90E-02 |
| 171 | APC 38:5 | 9768 | 9868 | 1.01 | 2439.5 | 7.71E-01 |
| 172 | APC 38:4 | 9135 | 8994 | 0.98 | 2472 | 8.74E-01 |
| 173 | APC 38:3 | 1473 | 1425 | 0.97 | 2226 | 2.46E-01 |
| 174 | APC 38:2 | 563 | 570 | 1.01 | 2510.5 | 9.98E-01 |
| 175 | modPC 506.3/3.50 | 10 | 10 | 0.96 | 2274.5 | 3.35E-01 |
| 176 | modPC 508.3/3.30 | 76 | 75 | 0.98 | 2454.5 | 8.18E-01 |
| 177 | modPC 510.3/4.00 | 29 | 29 | 1.02 | 2480 | 9.00E-01 |
| 178 | modPC 512.3/1.70 | 103 | 102 | 0.99 | 2467.5 | 8.59E-01 |
| 179 | modPC 536.3/3.50 | 53 | 46 | 0.88 | 2015 | 4.33E-02 |
| 180 | modPC 538.3/4.10 | 48 | 40 | 0.84 | 1984 | 3.18E-02 |
| 181 | modPC 552.4/3.90 | 61 | 51 | 0.83 | 2036 | 5.30E-02 |
| 182 | modPC 564.4/4.70 | 6 | 6 | 0.94 | 2199.5 | 2.04E-01 |
| 183 | modPC 566.4/5.10 | 7 | 6 | 0.95 | 2196 | 1.99E-01 |
| 184 | modPC 580.4/4.84 | 13 | 11 | 0.80 | 1833 | 5.75E-03 |
| 185 | modPC 590.4/4.80 | 3 | 3 | 1.05 | 2428 | 7.35E-01 |
| 186 | modPC 592.4/5.10 | 17 | 14 | 0.86 | 2010 | 4.13E-02 |
| 187 | modPC 594.4/3.26 | 132 | 168 | 1.27 | 2377 | 5.85E-01 |
| 188 | modPC 608.4/5.33 | 36 | 30 | 0.84 | 1758.5 | 2.17E-03 |
| 189 | modPC 608.4/3.84 | 19 | 26 | 1.40 | 2377 | 5.85E-01 |
| 190 | modPC 610.4/2.03 | 43 | 48 | 1.12 | 2343.5 | 4.95E-01 |
| 191 | modPC 622.4/4.54 | 3 | 3 | 0.94 | 2506 | 9.84E-01 |
| 192 | modPC 633.4/4.51 | 12 | 12 | 1.00 | 2485.5 | 9.17E-01 |
| 193 | modPC 636.4/3.37 | 174 | 168 | 0.96 | 2438.5 | 7.68E-01 |
| 194 | modPC 645.4/4.49 | 21 | 21 | 1.00 | 2382 | 5.99E-01 |
| 195 | modPC 650.4/3.24 | 701 | 761 | 1.09 | 2502 | 9.71E-01 |
| 196 | modPC 650.4/4.44 | 28 | 30 | 1.10 | 2435 | 7.57E-01 |
| 197 | modPC 650.4/3.94 | 22 | 29 | 1.30 | 2321.5 | 4.40E-01 |
| 198 | modPC 664.4/4.22 | 76 | 75 | 0.99 | 2471 | 8.71E-01 |
| 199 | modPC 666.4/2.99 | 156 | 165 | 1.06 | 2498 | 9.58E-01 |
| 200 | modPC 678.4/4.37 | 215 | 251 | 1.17 | 2428 | 7.35E-01 |
| 201 | modPC 678.4/4.94 | 68 | 68 | 0.99 | 2477 | 8.90E-01 |
| 202 | modPC 678.4/5.51 | 238 | 124 | 0.52 | 1437 | 1.21E-05 |
| 203 | modPC 690.4/4.11 | 66 | 56 | 0.85 | 2296 | 3.81E-01 |
| 204 | modPC 690.4/4.90 | 1734 | 1915 | 1.10 | 2192 | 1.94E-01 |
| 205 | modPC 690.4/6.00 | 104 | 93 | 0.90 | 2134 | 1.25E-01 |
| 206 | modPC 692.4/5.05 | 13 | 14 | 1.07 | 2037.5 | 5.38E-02 |
| 207 | modPC 692.4/5.52 | 98 | 65 | 0.66 | 1508.5 | 4.43E-05 |
| 208 | modPC 692.4/6.10 | 115 | 105 | 0.92 | 2063 | 6.80E-02 |

TABLE 9-continued

Lipid analyte levels[a] in stable and unstable cohorts

| # | Analyte | stable (median) | unstable (median) | stable/unstable | Mann-Whitney U | Asymp. Sig. (2-tailed) |
|---|---------|---|---|---|---|---|
| 209 | modPC 694.4/6.20 | 11 | 10 | 0.89 | 2045 | 5.77E-02 |
| 210 | modPC 703.5/4.09 | 51 | 65 | 1.28 | 2321 | 4.39E-01 |
| 211 | modPC 704.5/3.81 | 12 | 11 | 0.97 | 2440.5 | 7.74E-01 |
| 212 | modPC 706.5/3.79 | 4 | 5 | 1.19 | 2430 | 7.41E-01 |
| 213 | modPC 720.5/4.52 | 18 | 11 | 0.61 | 2480 | 9.00E-01 |
| 214 | modPC 736.5/5.38 | 28 | 22 | 0.80 | 1874 | 9.46E-03 |
| 215 | modPC 743.5/5.91 | 672 | 805 | 1.20 | 1969 | 2.73E-02 |
| 216 | modPC 745.5/6.35 | 1242 | 1038 | 0.84 | 1853 | 7.35E-03 |
| 217 | modPC 752.5/5.58 | 260 | 122 | 0.47 | 1373.5 | 3.59E-06 |
| 218 | modPC 764.5/6.52 | 447 | 424 | 0.95 | 2255 | 2.97E-01 |
| 219 | modPC 769.5/6.25 | 4772 | 4611 | 0.97 | 2160 | 1.53E-01 |
| 220 | modPC 772.5/5.37 | 75 | 75 | 0.99 | 2473 | 8.77E-01 |
| 221 | modPC 773.6/6.47 | 5940 | 6158 | 1.04 | 2275 | 3.36E-01 |
| 222 | modPC 788.6/5.19 | 101 | 106 | 1.05 | 2286 | 3.59E-01 |
| 223 | modPC 801.6/6.70 | 13486 | 13988 | 1.04 | 2235 | 2.61E-01 |
| 224 | modPC 816.6/5.58 | 32 | 29 | 0.93 | 2488 | 9.25E-01 |
| 225 | modPC 818.6/6.10 | 142 | 136 | 0.96 | 2143 | 1.34E-01 |
| 226 | modPC 818.6/6.48 | 1301 | 1244 | 0.96 | 2466 | 8.55E-01 |
| 227 | modPC 828.6/6.03 | 46 | 85 | 1.84 | 2484 | 9.12E-01 |
| 228 | modPC 843.6/7.10 | 410 | 405 | 0.99 | 2487.5 | 9.24E-01 |
| 229 | modPC 866.6/7.24 | 77 | 71 | 0.92 | 2266.5 | 3.19E-01 |
| 230 | modPC 878.6/5.98 | 28 | 26 | 0.92 | 2218 | 2.33E-01 |
| 231 | modPC 881.6/6.05 | 15 | 12 | 0.82 | 2049 | 5.98E-02 |
| 232 | COH | 490638 | 486413 | 0.99 | 2268.5 | 3.23E-01 |
| 233 | CE 14:0 | 11554 | 8074 | 0.70 | 1729.5 | 1.46E-03 |
| 234 | CE 15:0 | 9042 | 7827 | 0.87 | 2248 | 2.84E-01 |
| 235 | CE 16:2 | 9336 | 7547 | 0.81 | 1929 | 1.77E-02 |
| 236 | CE 16:1 | 136571 | 114150 | 0.84 | 2036 | 5.30E-02 |
| 237 | CE 16:0 | 183893 | 185978 | 1.01 | 2490 | 9.32E-01 |
| 238 | CE 17:1 | 26988 | 23067 | 0.85 | 2029 | 4.96E-02 |
| 239 | CE 17:0 | 10576 | 10203 | 0.96 | 2390 | 6.22E-01 |
| 240 | CE 18:3 | 799367 | 682914 | 0.85 | 1934.5 | 1.89E-02 |
| 241 | CE 18:2 | 4990566 | 5209877 | 1.04 | 2488 | 9.25E-01 |
| 242 | CE 18:1 | 1046679 | 1083523 | 1.04 | 2364 | 5.49E-01 |
| 243 | CE 18:0 | 24069 | 23270 | 0.97 | 2419 | 7.08E-01 |
| 244 | CE 20:5 | 1804461 | 1693410 | 0.94 | 2299 | 3.88E-01 |
| 245 | CE 20:4 | 4606083 | 4687500 | 1.02 | 2371 | 5.68E-01 |
| 246 | CE 20:3 | 313482 | 332744 | 1.06 | 2400 | 6.51E-01 |
| 247 | CE 20:2 | 6701 | 6193 | 0.92 | 2329 | 4.58E-01 |
| 248 | CE 20:1 | 865 | 873 | 1.01 | 2469 | 8.64E-01 |
| 249 | CE 22:6 | 1125037 | 1241975 | 1.10 | 2254 | 2.95E-01 |
| 250 | CE 22:5 | 79354 | 87933 | 1.11 | 2278 | 3.43E-01 |
| 251 | CE 22:4 | 7099 | 7820 | 1.10 | 2396 | 6.39E-01 |
| 252 | CE 22:3 | 365 | 352 | 0.96 | 2358 | 5.33E-01 |
| 253 | CE 22:2 | 137 | 146 | 1.07 | 2279 | 3.45E-01 |
| 254 | CE 22:1 | 540 | 578 | 1.07 | 2437 | 7.63E-01 |
| 255 | CE 22:0 | 323 | 308 | 0.95 | 2321 | 4.39E-01 |
| 256 | CE 24:6 | 1566 | 1664 | 1.06 | 2489 | 9.29E-01 |
| 257 | CE 24:5 | 919 | 882 | 0.96 | 2426.5 | 7.31E-01 |
| 258 | CE 24:4 | 288 | 293 | 1.02 | 2437 | 7.63E-01 |
| 259 | CE 24:3 | 29 | 31 | 1.09 | 2500 | 9.64E-01 |
| 260 | CE 24:2 | 246 | 229 | 0.93 | 2352 | 5.17E-01 |
| 261 | CE 24:1 | 1132 | 981 | 0.87 | 2291 | 3.70E-01 |
| 262 | CE 24:0 | 431 | 363 | 0.84 | 2236 | 2.63E-01 |
| 263 | modCE 558.5/7.74 | 17347 | 21339 | 1.23 | 2354 | 5.22E-01 |
| 264 | modCE 588.5/7.94 | 3552 | 3368 | 0.95 | 2461 | 8.39E-01 |
| 265 | modCE 682.7/8.76 | 7518 | 6876 | 0.91 | 2119 | 1.10E-01 |
| 266 | modCE 790.8/6.57 | 8677 | 8481 | 0.98 | 2403 | 6.60E-01 |
| 267 | DG 14:0 14:0 | 16 | 10 | 0.62 | 1776 | 2.75E-03 |
| 268 | DG 14:1 16:0 | 64 | 42 | 0.66 | 1861 | 8.10E-03 |
| 269 | DG 14:0 16:0 | 334 | 249 | 0.75 | 1954 | 2.33E-02 |
| 270 | DG 14:0 18:2 | 249 | 196 | 0.79 | 2017 | 4.42E-02 |
| 271 | DG 14:0 18:1 | 778 | 497 | 0.64 | 1888 | 1.12E-02 |
| 272 | DG 16:0 16:0 | 1171 | 1063 | 0.91 | 2416 | 6.99E-01 |
| 273 | DG 16:0 18:2 | 2520 | 2949 | 1.17 | 2300 | 3.90E-01 |
| 274 | DG 16:1 18:1 | 2974 | 2296 | 0.77 | 2118 | 1.09E-01 |
| 275 | DG 16:0 18:1 | 6236 | 6222 | 1.00 | 2503 | 9.74E-01 |
| 276 | DG 18:0 16:1 | 215 | 133 | 0.62 | 2036 | 5.30E-02 |
| 277 | DG 16:0 18:0 | 898 | 729 | 0.81 | 2123 | 1.14E-01 |
| 278 | DG 16:0 20:4 | 524 | 536 | 1.02 | 2400.5 | 6.53E-01 |
| 279 | DG 18:1 18:3 | 1180 | 1179 | 1.00 | 2258 | 3.03E-01 |
| 280 | DG 18:2 18:2 | 878 | 1055 | 1.20 | 2108 | 1.01E-01 |
| 281 | DG 16:0 20:3 | 311 | 216 | 0.70 | 2003 | 3.85E-02 |
| 282 | DG 18:1 18:2 | 7235 | 8569 | 1.18 | 2276 | 3.38E-01 |
| 283 | DG 18:0 18:2 | 636 | 614 | 0.97 | 2461 | 8.39E-01 |
| 284 | DG 18:1 18:1 | 8232 | 9135 | 1.11 | 2492 | 9.38E-01 |

TABLE 9-continued

Lipid analyte levels[a] in stable and unstable cohorts

| # | Analyte | stable (median) | unstable (median) | stable/unstable | Mann-Whitney U | Asymp. Sig. (2-tailed) |
|---|---|---|---|---|---|---|
| 285 | DG 18:0 18:1 | 1099 | 984 | 0.90 | 2274 | 3.34E−01 |
| 286 | DG 16:0 20:0 | 70 | 50 | 0.71 | 1766 | 2.41E−03 |
| 287 | DG 18:0 18:0 | 281 | 269 | 0.96 | 2399 | 6.48E−01 |
| 288 | DG 16:0 22:6 | 274 | 242 | 0.88 | 2357 | 5.30E−01 |
| 289 | DG 16:0 22:5 | 166 | 166 | 1.00 | 2477 | 8.90E−01 |
| 290 | DG 18:1 20:4 | 1801 | 1800 | 1.00 | 2462 | 8.42E−01 |
| 291 | DG 18:0 20:4 | 196 | 187 | 0.96 | 2468 | 8.61E−01 |
| 292 | DG 18:1 20:3 | 881 | 749 | 0.85 | 2086 | 8.34E−02 |
| 293 | DG 18:1 20:0 | 136 | 84 | 0.62 | 1592 | 1.81E−04 |
| 294 | TG 14:0 16:1 18:2 | 1960 | 1117 | 0.57 | 1711 | 1.12E−03 |
| 295 | TG 16:1 16:1 16:1 | 1015 | 545 | 0.54 | 1709 | 1.09E−03 |
| 296 | TG 14:0 16:0 18:2 | 4686 | 2933 | 0.63 | 1828.5 | 5.43E−03 |
| 297 | TG 14:0 16:1 18:1 | 6521 | 3704 | 0.57 | 1709 | 1.09E−03 |
| 298 | TG 14:1 16:0 18:1 | 7417 | 6243 | 0.84 | 2265 | 3.16E−01 |
| 299 | TG 14:1 16:1 18:0 | 6201 | 3692 | 0.60 | 1798 | 3.68E−03 |
| 300 | TG 18:1 14:0 16:0 | 9040 | 5803 | 0.64 | 1752 | 1.99E−03 |
| 301 | TG 16:0 16:0 16:0 | 2820 | 2009 | 0.71 | 2060 | 6.62E−02 |
| 302 | TG 15:0 18:1 16:0 | 6769 | 6293 | 0.93 | 2380 | 5.94E−01 |
| 303 | TG 17:0 16:0 16:1 | 2598 | 1751 | 0.67 | 2079 | 7.84E−02 |
| 304 | TG 17:0 18:1 14:0 | 2370 | 1840 | 0.78 | 2087 | 8.41E−02 |
| 305 | TG 14:0 18:2 18:2 | 668 | 486 | 0.73 | 2011 | 4.17E−02 |
| 306 | TG 14:1 18:0 18:2 | 649 | 471 | 0.73 | 1845 | 6.67E−03 |
| 307 | TG 14:1 18:1 18:1 | 3661 | 2683 | 0.73 | 1931 | 1.81E−02 |
| 308 | TG 16:1 16:1 18:1 | 4479 | 3547 | 0.79 | 2019 | 4.51E−02 |
| 309 | TG 16:0 16:0 18:2 | 9040 | 9235 | 1.02 | 2504 | 9.77E−01 |
| 310 | TG 16:1 16:1 18:0 | 381 | 251 | 0.66 | 1797 | 3.63E−03 |
| 311 | TG 16:0 16:1 18:1 | 37315 | 26921 | 0.72 | 2004 | 3.89E−02 |
| 312 | TG 14:0 18:0 18:1 | 524 | 344 | 0.66 | 1768 | 2.47E−03 |
| 313 | TG 16:0 16:0 18:1 | 33096 | 30064 | 0.91 | 2301 | 3.92E−01 |
| 314 | TG 16:0 16:0 18:0 | 3805 | 2691 | 0.71 | 2122 | 1.13E−01 |
| 315 | TG 15:0 18:1 18:1 | 1399 | 1428 | 1.02 | 2395 | 6.37E−01 |
| 316 | TG 17:0 18:1 16:1 | 6309 | 5383 | 0.85 | 2241 | 2.71E−01 |
| 317 | TG 17:0 18:2 16:0 | 3076 | 2308 | 0.75 | 2212 | 2.23E−01 |
| 318 | TG 17:0 18:1 16:0 | 3476 | 2551 | 0.73 | 2220 | 2.36E−01 |
| 319 | TG 17:0 16:0 18:0 | 317 | 218 | 0.69 | 2140 | 1.31E−01 |
| 320 | TG 16:0 18:2 18:2 | 11136 | 11393 | 1.02 | 2344 | 4.96E−01 |
| 321 | TG 16:1 18:1 18:2 | 9590 | 8250 | 0.86 | 2314 | 4.22E−01 |
| 322 | TG 16:1 18:1 18:1 | 10230 | 9729 | 0.95 | 2136 | 1.27E−01 |
| 323 | TG 16:0 18:1 18:2 | 43541 | 47844 | 1.10 | 2192 | 1.94E−01 |
| 324 | TG 16:0 18:1 18:1 | 97258 | 104695 | 1.08 | 2494.5 | 9.46E−01 |
| 325 | TG 16:0 18:0 18:1 | 3702 | 4087 | 1.10 | 2504 | 9.77E−01 |
| 326 | TG 17:0 18:1 18:1 | 2351 | 2207 | 0.94 | 2303 | 3.97E−01 |
| 327 | TG 18:2 18:2 18:2 | 2752 | 3083 | 1.12 | 2504 | 9.77E−01 |
| 328 | TG 18:1 18:2 18:2 | 4822 | 5347 | 1.11 | 2496 | 9.51E−01 |
| 329 | TG 18:0 18:2 18:2 | 966 | 1085 | 1.12 | 2481.5 | 9.04E−01 |
| 330 | TG 18:1 18:1 18:2 | 6735 | 7857 | 1.17 | 2191 | 1.92E−01 |
| 331 | TG 18:1 18:1 18:1 | 44053 | 45755 | 1.04 | 2509 | 9.93E−01 |
| 332 | TG 18:0 18:1 18:1 | 8120 | 7955 | 0.98 | 2337.5 | 4.80E−01 |
| 333 | TG 18:0 18:0 18:1 | 1715 | 1686 | 0.98 | 2275 | 3.36E−01 |
| 334 | TG 18:0 18:0 18:0 | 257 | 166 | 0.64 | 1972 | 2.81E−02 |
| 335 | TG 18:2 18:2 20:4 | 1288 | 1269 | 0.99 | 2441 | 7.76E−01 |
| 336 | TG 18:1 18:1 20:4 | 6211 | 6972 | 1.12 | 2255.5 | 2.98E−01 |
| 337 | TG 18:1 18:1 22:6 | 637 | 661 | 1.04 | 2333.5 | 4.70E−01 |

[a]levels are expressed as pmol/mL plasma

TABLE 9a

Lipid analyte levels[a] in control (normal) and CAD (heart disease)

| # | control (median) | CAD (median) | CAD/control | Mann-Whitney U | Asymp. Sig. (2-tailed) |
|---|---|---|---|---|---|
| 1 | 385 | 395 | 1.03 | 3847 | 1.83E−01 |
| 2 | 202 | 208 | 1.03 | 3635.5 | 6.00E−02 |
| 3 | 129 | 180 | 1.39 | 2167 | 1.31E−08 |
| 4 | 121 | 144 | 1.20 | 3120 | 1.30E−03 |
| 5 | 845 | 776 | 0.92 | 3649 | 6.49E−02 |
| 6 | 1152 | 1211 | 1.05 | 3551 | 3.58E−02 |
| 7 | 3139 | 2539 | 0.81 | 2848 | 8.83E−05 |
| 8 | 2115 | 1734 | 0.82 | 2702 | 1.72E−05 |
| 9 | 66 | 59 | 0.90 | 3840 | 1.77E−01 |
| 10 | 408 | 362 | 0.89 | 3492.5 | 2.44E−02 |
| 11 | 632 | 453 | 0.72 | 2539 | 2.35E−06 |
| 12 | 5053 | 3352 | 0.66 | 1935.5 | 3.29E−10 |
| 13 | 5179 | 4346 | 0.84 | 2923 | 1.94E−04 |
| 14 | 7718 | 5057 | 0.66 | 2055 | 2.30E−09 |
| 15 | 9745 | 8562 | 0.88 | 3155.5 | 1.78E−03 |
| 16 | 79 | 72 | 0.91 | 3520.5 | 2.94E−02 |
| 17 | 154 | 142 | 0.92 | 3803.5 | 1.48E−01 |
| 18 | 114 | 107 | 0.93 | 3949 | 2.85E−01 |
| 19 | 755 | 625 | 0.83 | 2842 | 8.28E−05 |
| 20 | 2716 | 2214 | 0.82 | 2811 | 5.91E−05 |
| 21 | 754 | 608 | 0.81 | 2627 | 7.02E−06 |
| 22 | 1730 | 1479 | 0.85 | 2994 | 3.96E−04 |

TABLE 9a-continued

Lipid analyte levels[a] in control (normal) and CAD (heart disease)

| # | control (median) | CAD (median) | CAD/control | Mann-Whitney U | Asymp. Sig. (2-tailed) |
|---|---|---|---|---|---|
| 23 | 168 | 163 | 0.97 | 3808 | 1.52E-01 |
| 24 | 185 | 164 | 0.89 | 3403.5 | 1.31E-02 |
| 25 | 72 | 66 | 0.90 | 3635.5 | 6.00E-02 |
| 26 | 309 | 262 | 0.85 | 3147 | 1.65E-03 |
| 27 | 741 | 614 | 0.83 | 3287.5 | 5.40E-03 |
| 28 | 418 | 321 | 0.77 | 2237 | 3.72E-08 |
| 29 | 1648 | 1485 | 0.90 | 3353 | 8.99E-03 |
| 30 | 603 | 477 | 0.79 | 2322 | 1.27E-07 |
| 31 | 346 | 330 | 0.95 | 3705 | 8.90E-02 |
| 32 | 857 | 719 | 0.84 | 3240.5 | 3.69E-03 |
| 33 | 1145 | 1059 | 0.92 | 3900.5 | 2.32E-01 |
| 34 | 806 | 638 | 0.79 | 2664 | 1.10E-05 |
| 35 | 18 | 22 | 1.18 | 3321 | 7.03E-03 |
| 36 | 25 | 21 | 0.83 | 2686.5 | 1.43E-05 |
| 37 | 4 | 4 | 0.88 | 3146.5 | 1.65E-03 |
| 38 | 347 | 273 | 0.79 | 2795.5 | 4.98E-05 |
| 39 | 623 | 641 | 1.03 | 4148.5 | 5.81E-01 |
| 40 | 45 | 51 | 1.11 | 3493 | 2.45E-02 |
| 41 | 32 | 23 | 0.70 | 1880 | 1.29E-10 |
| 42 | 185 | 150 | 0.81 | 2818 | 6.38E-05 |
| 43 | 194 | 136 | 0.70 | 2181.5 | 1.63E-08 |
| 44 | 344 | 367 | 1.07 | 4114 | 5.21E-01 |
| 45 | 79 | 79 | 1.01 | 3777.5 | 1.30E-01 |
| 46 | 43 | 48 | 1.11 | 3177 | 2.15E-03 |
| 47 | 37 | 38 | 1.03 | 3909 | 2.41E-01 |
| 48 | 68 | 83 | 1.22 | 4163 | 6.07E-01 |
| 49 | 15313 | 12696 | 0.83 | 2580.5 | 3.96E-06 |
| 50 | 10000 | 8246 | 0.82 | 2690.5 | 1.50E-05 |
| 51 | 22484 | 19403 | 0.86 | 2962 | 2.89E-04 |
| 52 | 127011 | 112450 | 0.89 | 2408 | 4.18E-07 |
| 53 | 15061 | 15330 | 1.02 | 4025 | 3.83E-01 |
| 54 | 27213 | 28333 | 1.04 | 3846 | 1.82E-01 |
| 55 | 9541 | 9096 | 0.95 | 3648 | 6.46E-02 |
| 56 | 17806 | 15509 | 0.87 | 2692.5 | 1.54E-05 |
| 57 | 33168 | 27073 | 0.82 | 2348.5 | 1.84E-07 |
| 58 | 51907 | 52810 | 1.02 | 4240 | 7.53E-01 |
| 59 | 72611 | 67172 | 0.93 | 2801 | 5.29E-05 |
| 60 | 22588 | 17197 | 0.76 | 2084 | 3.64E-09 |
| 61 | 7 | 6 | 0.79 | 3503 | 2.62E-02 |
| 62 | 66 | 65 | 1.00 | 4138.5 | 5.63E-01 |
| 63 | 117 | 106 | 0.90 | 3821 | 1.61E-01 |
| 64 | 67 | 64 | 0.96 | 4166.5 | 6.13E-01 |
| 65 | 30 | 33 | 1.12 | 4195 | 6.66E-01 |
| 66 | 216 | 145 | 0.67 | 3004 | 4.37E-04 |
| 67 | 1176 | 886 | 0.75 | 3453 | 1.86E-02 |
| 68 | 95 | 51 | 0.53 | 2596 | 4.80E-06 |
| 69 | 1290 | 909 | 0.70 | 2862 | 1.03E-04 |
| 70 | 263 | 185 | 0.71 | 3027.5 | 5.49E-04 |
| 71 | 150 | 98 | 0.66 | 2168 | 1.33E-08 |
| 72 | 148 | 90 | 0.61 | 2352 | 1.93E-07 |
| 73 | 104 | 113 | 1.09 | 3660 | 6.92E-02 |
| 74 | 60 | 53 | 0.89 | 3643 | 6.27E-02 |
| 75 | 1727 | 1608 | 0.93 | 3949 | 2.85E-01 |
| 76 | 1055 | 1181 | 1.12 | 3865 | 1.98E-01 |
| 77 | 226 | 201 | 0.89 | 3537 | 3.27E-02 |
| 78 | 2115 | 2297 | 1.09 | 4105 | 5.06E-01 |
| 79 | 1214 | 1023 | 0.84 | 3379 | 1.09E-02 |
| 80 | 4647 | 3822 | 0.82 | 3527 | 3.06E-02 |
| 81 | 978 | 826 | 0.85 | 3662 | 7.00E-02 |
| 82 | 23 | 21 | 0.94 | 3433 | 1.62E-02 |
| 83 | 2630 | 2691 | 1.02 | 4199 | 6.74E-01 |
| 84 | 1869 | 1864 | 1.00 | 4287 | 8.47E-01 |
| 85 | 4566 | 4988 | 1.09 | 4022 | 3.79E-01 |
| 86 | 468 | 529 | 1.13 | 3938.5 | 2.73E-01 |
| 87 | 104 | 94 | 0.90 | 4032 | 3.93E-01 |
| 88 | 58 | 50 | 0.87 | 3843.5 | 1.80E-01 |
| 89 | 238 | 226 | 0.95 | 4153 | 5.89E-01 |
| 90 | 1289 | 1405 | 1.09 | 4100 | 4.98E-01 |
| 91 | 206 | 210 | 1.02 | 4023 | 3.81E-01 |
| 92 | 120 | 73 | 0.61 | 2332 | 1.46E-07 |
| 93 | 2026 | 1591 | 0.78 | 2824 | 6.81E-05 |
| 94 | 53 | 33 | 0.62 | 1975 | 6.32E-10 |
| 95 | 1776 | 1290 | 0.73 | 2931 | 2.11E-04 |
| 96 | 1446 | 941 | 0.65 | 2024 | 1.40E-09 |
| 97 | 6918 | 5398 | 0.78 | 2199 | 2.12E-08 |
| 98 | 1925 | 1370 | 0.71 | 2174 | 1.46E-08 |
| 99 | 8 | 6 | 0.69 | 2625 | 6.85E-06 |
| 100 | 310 | 219 | 0.71 | 2511.5 | 1.65E-06 |
| 101 | 1055 | 808 | 0.77 | 2359 | 2.13E-07 |
| 102 | 12132 | 10752 | 0.89 | 3273 | 4.81E-03 |
| 103 | 2831 | 2187 | 0.77 | 3219 | 3.08E-03 |
| 104 | 180 | 143 | 0.80 | 3041 | 6.25E-04 |
| 105 | 665 | 523 | 0.79 | 2942 | 2.36E-04 |
| 106 | 628 | 545 | 0.87 | 3241 | 3.70E-03 |
| 107 | 168 | 142 | 0.85 | 3669 | 7.28E-02 |
| 108 | 1969 | 1313 | 0.67 | 2097 | 4.46E-09 |
| 109 | 1276 | 971 | 0.76 | 2615 | 6.06E-06 |
| 110 | 3938 | 3413 | 0.87 | 3190 | 2.41E-03 |
| 111 | 74468 | 63237 | 0.85 | 2594 | 4.68E-06 |
| 112 | 32914 | 24015 | 0.73 | 2268 | 5.85E-08 |
| 113 | 24820 | 20963 | 0.84 | 2897 | 1.48E-04 |
| 114 | 26571 | 20000 | 0.75 | 2457 | 8.07E-07 |
| 115 | 1894 | 1427 | 0.75 | 3398 | 1.26E-02 |
| 116 | 7632 | 7778 | 1.02 | 3952 | 2.89E-01 |
| 117 | 3236 | 3061 | 0.95 | 4026 | 3.85E-01 |
| 118 | 385 | 301 | 0.78 | 3258 | 4.26E-03 |
| 119 | 293 | 228 | 0.78 | 2730.5 | 2.39E-05 |
| 120 | 150 | 86 | 0.57 | 1208 | 3.11E-16 |
| 121 | 2456 | 2533 | 1.03 | 3792 | 1.40E-01 |
| 122 | 551 | 436 | 0.79 | 2683 | 1.37E-05 |
| 123 | 404 | 327 | 0.81 | 3199 | 2.60E-03 |
| 124 | 145 | 112 | 0.77 | 2768 | 3.66E-05 |
| 125 | 6822 | 6130 | 0.90 | 3343 | 8.33E-03 |
| 126 | 12050 | 10636 | 0.88 | 2938 | 2.26E-04 |
| 127 | 156579 | 163194 | 1.04 | 3946 | 2.82E-01 |
| 128 | 14091 | 12478 | 0.89 | 3309 | 6.40E-03 |
| 129 | 27705 | 21007 | 0.76 | 2613 | 5.91E-06 |
| 130 | 280676 | 252174 | 0.90 | 2814 | 6.10E-05 |
| 131 | 148026 | 155147 | 1.05 | 4046.5 | 4.14E-01 |
| 132 | 4705 | 3851 | 0.82 | 2271 | 6.12E-08 |
| 133 | 46569 | 36846 | 0.79 | 3304 | 6.15E-03 |
| 134 | 107556 | 115909 | 1.08 | 3711.5 | 9.22E-02 |
| 135 | 117647 | 116393 | 0.99 | 3785 | 1.35E-01 |
| 136 | 230220 | 190000 | 0.83 | 2352 | 1.93E-07 |
| 137 | 61373 | 55038 | 0.90 | 3369 | 1.01E-02 |
| 138 | 61353 | 56179 | 0.92 | 3603.5 | 4.96E-02 |
| 139 | 88083 | 95378 | 1.08 | 3848.5 | 1.84E-01 |
| 140 | 5171 | 4496 | 0.87 | 3500.5 | 2.57E-02 |
| 141 | 25528 | 27091 | 1.06 | 4231 | 7.35E-01 |
| 142 | 16434 | 17222 | 1.05 | 4194.5 | 6.65E-01 |
| 143 | 2224 | 1862 | 0.84 | 3342.5 | 8.30E-03 |
| 144 | 2872 | 2630 | 0.92 | 3720 | 9.66E-02 |
| 145 | 1524 | 1188 | 0.78 | 3169.5 | 2.02E-03 |
| 146 | 2116 | 1919 | 0.91 | 3608 | 5.09E-02 |
| 147 | 5147 | 5180 | 1.01 | 4355 | 9.87E-01 |
| 148 | 5753 | 4850 | 0.84 | 2946 | 2.46E-04 |
| 149 | 2298 | 2141 | 0.93 | 3736.5 | 1.05E-01 |
| 150 | 2637 | 2179 | 0.83 | 3095 | 1.03E-03 |
| 151 | 12749 | 10895 | 0.85 | 3205 | 2.74E-03 |
| 152 | 9750 | 9643 | 0.99 | 4279.5 | 8.32E-01 |
| 153 | 481 | 398 | 0.83 | 2988 | 3.74E-04 |
| 154 | 1343 | 1049 | 0.78 | 2965 | 2.97E-04 |
| 155 | 1924 | 1732 | 0.90 | 3272 | 4.77E-03 |
| 156 | 6800 | 7013 | 1.03 | 4330 | 9.35E-01 |
| 157 | 4760 | 4902 | 1.03 | 4000.5 | 3.50E-01 |
| 158 | 8960 | 7970 | 0.89 | 2910.5 | 1.71E-04 |
| 159 | 575 | 482 | 0.84 | 2843 | 8.37E-05 |
| 160 | 2302 | 2097 | 0.91 | 3457 | 1.91E-02 |
| 161 | 4266 | 2754 | 0.65 | 1526 | 2.05E-13 |
| 162 | 5162 | 4618 | 0.89 | 3350.5 | 8.82E-03 |
| 163 | 742 | 646 | 0.87 | 3111 | 1.20E-03 |
| 164 | 8600 | 7273 | 0.85 | 2663.5 | 1.09E-05 |
| 165 | 12154 | 10517 | 0.87 | 2777 | 4.05E-05 |
| 166 | 4892 | 3935 | 0.80 | 2276 | 6.57E-08 |
| 167 | 3434 | 2456 | 0.72 | 2220 | 2.90E-08 |
| 168 | 1429 | 1148 | 0.80 | 3115.5 | 1.25E-03 |
| 169 | 135 | 109 | 0.81 | 3005.5 | 4.44E-04 |
| 170 | 5355 | 3902 | 0.73 | 2199 | 2.12E-08 |
| 171 | 11176 | 9833 | 0.88 | 2831 | 7.35E-05 |
| 172 | 10267 | 9030 | 0.88 | 3392 | 1.20E-02 |

TABLE 9a-continued

Lipid analyte levels$^a$ in control (normal) and CAD (heart disease)

| # | control (median) | CAD (median) | CAD/ control | Mann-Whitney U | Asymp. Sig. (2-tailed) |
|---|---|---|---|---|---|
| 173 | 1681 | 1460 | 0.87 | 3242 | 3.73E−03 |
| 174 | 812 | 570 | 0.70 | 2573.5 | 3.63E−06 |
| 175 | 15 | 10 | 0.69 | 2480 | 1.09E−06 |
| 176 | 96 | 76 | 0.79 | 2842 | 8.28E−05 |
| 177 | 40 | 29 | 0.73 | 2563 | 3.18E−06 |
| 178 | 127 | 103 | 0.81 | 2918 | 1.84E−04 |
| 179 | 64 | 48 | 0.75 | 2855 | 9.52E−05 |
| 180 | 73 | 44 | 0.60 | 1758 | 1.54E−11 |
| 181 | 98 | 54 | 0.56 | 1143 | 7.59E−17 |
| 182 | 8 | 6 | 0.67 | 2141 | 8.81E−09 |
| 183 | 9 | 7 | 0.72 | 1954 | 4.47E−10 |
| 184 | 24 | 11 | 0.49 | 844 | 8.09E−20 |
| 185 | 4 | 3 | 0.66 | 2376 | 2.70E−07 |
| 186 | 20 | 16 | 0.77 | 2607 | 5.49E−06 |
| 187 | 166 | 168 | 1.01 | 4185.5 | 6.48E−01 |
| 188 | 53 | 33 | 0.62 | 1157 | 1.03E−16 |
| 189 | 22 | 24 | 1.07 | 4355 | 9.87E−01 |
| 190 | 45 | 47 | 1.05 | 4077.5 | 4.62E−01 |
| 191 | 5 | 3 | 0.68 | 3658 | 6.84E−02 |
| 192 | 15 | 12 | 0.78 | 2313.5 | 1.12E−07 |
| 193 | 253 | 171 | 0.68 | 3966 | 3.06E−01 |
| 194 | 29 | 21 | 0.71 | 2666 | 1.12E−05 |
| 195 | 973 | 747 | 0.77 | 3551 | 3.58E−02 |
| 196 | 37 | 30 | 0.82 | 3754 | 1.16E−01 |
| 197 | 34 | 27 | 0.80 | 3802 | 1.47E−01 |
| 198 | 96 | 75 | 0.78 | 4054 | 4.26E−01 |
| 199 | 189 | 162 | 0.86 | 4041 | 4.06E−01 |
| 200 | 320 | 246 | 0.77 | 3387.5 | 1.16E−02 |
| 201 | 82 | 68 | 0.83 | 2928 | 2.04E−04 |
| 202 | 340 | 150 | 0.44 | 2000 | 9.51E−10 |
| 203 | 66 | 61 | 0.93 | 3645 | 6.34E−02 |
| 204 | 2277 | 1866 | 0.82 | 2575 | 3.69E−06 |
| 205 | 143 | 98 | 0.69 | 2268 | 5.85E−08 |
| 206 | 18 | 14 | 0.80 | 2580 | 3.93E−06 |
| 207 | 131 | 78 | 0.59 | 2100 | 4.67E−09 |
| 208 | 157 | 109 | 0.69 | 2020 | 1.31E−09 |
| 209 | 13 | 10 | 0.76 | 2322 | 1.27E−07 |
| 210 | 79 | 59 | 0.75 | 3766 | 1.23E−01 |
| 211 | 17 | 11 | 0.65 | 3823 | 1.63E−01 |
| 212 | 4 | 4 | 1.11 | 4157 | 5.96E−01 |
| 213 | 29 | 15 | 0.50 | 3610 | 5.16E−02 |
| 214 | 34 | 24 | 0.71 | 2142 | 8.95E−09 |
| 215 | 840 | 764 | 0.91 | 3724 | 9.86E−02 |
| 216 | 1658 | 1128 | 0.68 | 1599.5 | 8.37E−13 |
| 217 | 312 | 165 | 0.53 | 2197.5 | 2.07E−08 |
| 218 | 427 | 436 | 1.02 | 4261 | 7.95E−01 |
| 219 | 5503 | 4684 | 0.85 | 2760 | 3.34E−05 |
| 220 | 76 | 75 | 0.98 | 4157.5 | 5.97E−01 |
| 221 | 6973 | 6082 | 0.87 | 3001.5 | 4.27E−04 |
| 222 | 101 | 103 | 1.01 | 4305.5 | 8.85E−01 |
| 223 | 16763 | 13719 | 0.82 | 2697.5 | 1.63E−05 |
| 224 | 34 | 31 | 0.89 | 3802 | 1.47E−01 |
| 225 | 196 | 139 | 0.71 | 2644.5 | 8.67E−06 |
| 226 | 1680 | 1301 | 0.77 | 3080.5 | 9.05E−04 |
| 227 | 58 | 70 | 1.20 | 3788 | 1.37E−01 |
| 228 | 514 | 405 | 0.79 | 2743 | 2.76E−05 |
| 229 | 110 | 74 | 0.67 | 1706.5 | 6.08E−12 |
| 230 | 45 | 28 | 0.61 | 2362 | 2.22E−07 |
| 231 | 21 | 12 | 0.58 | 2002 | 9.82E−10 |
| 232 | 606232 | 486683 | 0.80 | 2616 | 6.13E−06 |
| 233 | 9908 | 9498 | 0.96 | 4063.5 | 4.40E−01 |
| 234 | 9154 | 8247 | 0.90 | 3866 | 1.99E−01 |
| 235 | 9287 | 8247 | 0.89 | 3721 | 9.71E−02 |
| 236 | 107973 | 121688 | 1.13 | 3653.5 | 6.66E−02 |
| 237 | 193265 | 185566 | 0.96 | 3809 | 1.52E−01 |
| 238 | 21999 | 25811 | 1.17 | 3900 | 2.32E−01 |
| 239 | 11940 | 10329 | 0.87 | 3543 | 3.40E−02 |
| 240 | 826948 | 739499 | 0.89 | 3571 | 4.06E−02 |
| 241 | 5662848 | 5062762 | 0.89 | 4049 | 4.18E−01 |
| 242 | 1114956 | 1054500 | 0.95 | 4135 | 5.57E−01 |
| 243 | 28381 | 23908 | 0.84 | 2800 | 5.23E−05 |
| 244 | 1972637 | 1731501 | 0.88 | 3773 | 1.27E−01 |
| 245 | 4259259 | 4687500 | 1.10 | 3791 | 1.39E−01 |
| 246 | 262959 | 328193 | 1.25 | 2990 | 3.81E−04 |
| 247 | 6736 | 6448 | 0.96 | 4044 | 4.11E−01 |
| 248 | 1247 | 873 | 0.70 | 2464 | 8.86E−07 |
| 249 | 1316413 | 1201639 | 0.91 | 4083 | 4.71E−01 |
| 250 | 78516 | 81625 | 1.04 | 3954.5 | 2.92E−01 |
| 251 | 6344 | 7497 | 1.18 | 3454 | 1.87E−02 |
| 252 | 372 | 362 | 0.97 | 4128 | 5.45E−01 |
| 253 | 197 | 142 | 0.72 | 2502 | 1.46E−06 |
| 254 | 666 | 570 | 0.86 | 3240 | 3.67E−03 |
| 255 | 455 | 317 | 0.70 | 2594 | 4.68E−06 |
| 256 | 1616 | 1595 | 0.99 | 4169 | 6.18E−01 |
| 257 | 1124 | 902 | 0.80 | 3496 | 2.50E−02 |
| 258 | 324 | 292 | 0.90 | 3772 | 1.27E−01 |
| 259 | 64 | 30 | 0.48 | 3553 | 3.62E−02 |
| 260 | 286 | 231 | 0.81 | 3186 | 2.33E−03 |
| 261 | 1318 | 1077 | 0.82 | 3308 | 6.35E−03 |
| 262 | 517 | 386 | 0.75 | 2942 | 2.36E−04 |
| 263 | 18709 | 19891 | 1.06 | 4223 | 7.20E−01 |
| 264 | 5392 | 3376 | 0.63 | 3790 | 1.39E−01 |
| 265 | 7857 | 7002 | 0.89 | 3735 | 1.05E−01 |
| 266 | 8557 | 8601 | 1.01 | 4228 | 7.29E−01 |
| 267 | 16 | 13 | 0.79 | 3544 | 3.42E−02 |
| 268 | 61 | 53 | 0.88 | 4055.5 | 4.28E−01 |
| 269 | 259 | 289 | 1.12 | 4361.5 | 1.00E+00 |
| 270 | 258 | 211 | 0.82 | 3731 | 1.02E−01 |
| 271 | 534 | 590 | 1.10 | 4135 | 5.57E−01 |
| 272 | 735 | 1129 | 1.54 | 3133 | 1.46E−03 |
| 273 | 2380 | 2913 | 1.22 | 3601 | 4.88E−02 |
| 274 | 1785 | 2610 | 1.46 | 3191 | 2.43E−03 |
| 275 | 4167 | 6222 | 1.49 | 3067 | 7.98E−04 |
| 276 | 140 | 156 | 1.12 | 3641 | 6.20E−02 |
| 277 | 665 | 825 | 1.24 | 3936 | 2.70E−01 |
| 278 | 397 | 530 | 1.34 | 3221 | 3.13E−03 |
| 279 | 1044 | 1179 | 1.13 | 4037 | 4.01E−01 |
| 280 | 959 | 980 | 1.02 | 4195 | 6.66E−01 |
| 281 | 178 | 240 | 1.35 | 3045 | 6.49E−04 |
| 282 | 6258 | 7786 | 1.24 | 3563 | 3.86E−02 |
| 283 | 509 | 625 | 1.23 | 3738 | 1.06E−01 |
| 284 | 6148 | 8768 | 1.43 | 2991 | 3.85E−04 |
| 285 | 786 | 1035 | 1.32 | 3511 | 2.76E−02 |
| 286 | 79 | 53 | 0.67 | 3169 | 2.01E−03 |
| 287 | 282 | 275 | 0.98 | 3835 | 1.73E−01 |
| 288 | 247 | 262 | 1.06 | 4316.5 | 9.07E−01 |
| 289 | 136 | 166 | 1.23 | 3539 | 3.31E−02 |
| 290 | 1359 | 1800 | 1.32 | 3053 | 7.00E−04 |
| 291 | 189 | 189 | 1.00 | 4141 | 5.68E−01 |
| 292 | 529 | 812 | 1.54 | 2709.5 | 1.87E−05 |
| 293 | 134 | 98 | 0.73 | 2937 | 2.24E−04 |
| 294 | 1993 | 1407 | 0.71 | 3168.5 | 2.00E−03 |
| 295 | 1027 | 707 | 0.69 | 3154 | 1.76E−03 |
| 296 | 4329 | 3333 | 0.77 | 3249 | 3.95E−03 |
| 297 | 6584 | 4673 | 0.71 | 3153 | 1.74E−03 |
| 298 | 5439 | 6702 | 1.23 | 4135.5 | 5.58E−01 |
| 299 | 5238 | 4194 | 0.80 | 3811.5 | 1.54E−01 |
| 300 | 8485 | 6784 | 0.80 | 3314.5 | 6.68E−03 |
| 301 | 2780 | 2333 | 0.84 | 3833 | 1.71E−01 |
| 302 | 5385 | 6398 | 1.19 | 4214 | 7.02E−01 |
| 303 | 1823 | 2017 | 1.11 | 4032.5 | 3.94E−01 |
| 304 | 1973 | 1986 | 1.01 | 3907.5 | 2.40E−01 |
| 305 | 952 | 581 | 0.61 | 2724 | 2.22E−05 |
| 306 | 714 | 526 | 0.74 | 3294 | 5.69E−03 |
| 307 | 3257 | 3062 | 0.94 | 3507 | 2.69E−02 |
| 308 | 3629 | 3879 | 1.07 | 4324 | 9.23E−01 |
| 309 | 7924 | 9235 | 1.17 | 4209.5 | 6.94E−01 |
| 310 | 398 | 288 | 0.72 | 3247 | 3.89E−03 |
| 311 | 28012 | 29731 | 1.06 | 4279.5 | 8.32E−01 |
| 312 | 494 | 406 | 0.82 | 3385 | 1.14E−02 |
| 313 | 23735 | 31195 | 1.31 | 4127.5 | 5.44E−01 |
| 314 | 3559 | 3197 | 0.90 | 3986 | 3.31E−01 |
| 315 | 1312 | 1415 | 1.08 | 4133 | 5.54E−01 |
| 316 | 4941 | 5824 | 1.18 | 3942 | 2.77E−01 |
| 317 | 2207 | 2558 | 1.16 | 3924.5 | 2.58E−01 |
| 318 | 2392 | 2780 | 1.16 | 4177 | 6.33E−01 |
| 319 | 218 | 234 | 1.07 | 4297.5 | 8.68E−01 |
| 320 | 10838 | 11250 | 1.04 | 4003.5 | 3.54E−01 |
| 321 | 8416 | 8594 | 1.02 | 4143.5 | 5.72E−01 |
| 322 | 8477 | 9857 | 1.16 | 3717 | 9.50E−02 |

TABLE 9a-continued

Lipid analyte levels[a] in control (normal) and CAD (heart disease)

| # | control (median) | CAD (median) | CAD/ control | Mann-Whitney U | Asymp. Sig. (2-tailed) |
|---|---|---|---|---|---|
| 323 | 38613 | 45076 | 1.17 | 4068 | 4.47E−01 |
| 324 | 82550 | 104525 | 1.27 | 3475 | 2.16E−02 |
| 325 | 3150 | 4077 | 1.29 | 3541 | 3.35E−02 |
| 326 | 1949 | 2246 | 1.15 | 3743 | 1.09E−01 |
| 327 | 3239 | 2856 | 0.88 | 3746 | 1.11E−01 |
| 328 | 5850 | 5042 | 0.86 | 3715 | 9.40E−02 |
| 329 | 1139 | 1039 | 0.91 | 3620 | 5.48E−02 |
| 330 | 7221 | 7221 | 1.00 | 4183 | 6.44E−01 |
| 331 | 37654 | 45293 | 1.20 | 3674 | 7.49E−02 |
| 332 | 7800 | 8015 | 1.03 | 4086 | 4.75E−01 |
| 333 | 1676 | 1686 | 1.01 | 4274 | 8.21E−01 |
| 334 | 232 | 197 | 0.85 | 3804 | 1.49E−01 |
| 335 | 1600 | 1269 | 0.79 | 3347 | 8.59E−03 |
| 336 | 6531 | 6756 | 1.03 | 4283 | 8.39E−01 |
| 337 | 689 | 648 | 0.94 | 3984 | 3.28E−01 |

[a]levels are expressed as pmol/mL plasma

TABLE 10

Initial summary[a] of univariate analysis of plasma lipids in control, stable CAD and unstable CAD cohorts.

| Lipid group | # of Species | Stable vs unstable $p < 0.05$ | Stable vs unstable $p < 0.01$ | control vs CAD $p < 0.05$ | control vs CAD $p < 0.01$ |
|---|---|---|---|---|---|
| ceramide (CER) | 7 | 2 | 1 | 4 | 3 |
| monohexosylceramide (MHC) | 7 | 0 | 0 | 6 | 5 |
| dihexosylceramide (DHC) | 7 | 1 | 1 | 5 | 4 |
| trihexosylcermide (THC) | 7 | 0 | 0 | 5 | 4 |
| $G_{M3}$ Ganglioside (GM3) | 6 | 1 | 0 | 4 | 4 |
| modified ceramides (modCer) | 14 | 3 | 1 | 9 | 8 |
| sphingomyelin (SM) | 12 | 2 | 2 | 8 | 8 |
| phosphatidylglycerol (PG) | 4 | 0 | 0 | 1 | 0 |
| bis(monoacylglycero)phosphate (BMP) | 1 | 0 | 0 | 0 | 0 |
| phosphatidylserine (PS) | 7 | 0 | 0 | 7 | 6 |
| phosphatidylethanolamine (PE) | 18 | 1 | 0 | 4 | 0 |
| phosphatidylinositol (PI) | 17 | 11 | 7 | 15 | 15 |
| lysophosphatidylcholine (LPC) | 14 | 8 | 5 | 11 | 10 |
| lysoplatelet activating factor (LPAF) | 3 | 0 | 0 | 3 | 3 |
| phosphatidylcholine (PC) | 19 | 3 | 1 | 12 | 9 |
| odd-chain phosphatidylcholine (oddPC) | 15 | 3 | 0 | 8 | 8 |
| alkylphosphatidylcholine (APC) | 16 | 1 | 1 | 16 | 14 |
| modified phosphatidylcholine (modPC) | 57 | 11 | 7 | 37 | 35 |
| free cholesterol (COH) | 1 | 0 | 0 | 1 | 1 |
| cholesterol esters (CE) | 30 | 4 | 1 | 14 | 9 |
| modified cholesterol esters (modCE) | 4 | 0 | 0 | 0 | 0 |
| diacylglycerol (DG) | 27 | 8 | 4 | 15 | 10 |
| triaclyglycerol (TG) | 44 | 14 | 9 | 13 | 9 |
| Total lipid species | 337 | 73 | 40 | 198 | 165 |

[a]table shows the number of lipids in each class with p values below the indicated level

TABLE 11

Analysis of variance[a] of stable vs unstable cohort

| | ANOVA | | | | | Covariates | | |
|---|---|---|---|---|---|---|---|---|
| | Sum of Squares | df | Mean Square | F | Sig. | Variable | Partial Correlation | Sig |
| Model 1 (traditional risk factors) $R^2 = 0.304$ | | | | | | | | |
| Regression | 8.095 | 2 | 4.048 | 22.705 | .000[b] | CRP | .532 | .000 |
| Residual | 18.540 | 104 | .178 | | | smoker | .236 | .015 |
| Total | 26.636 | 106 | | | | | | |
| Model 2 (lipids) $R^2 = 0.353$ | | | | | | | | |
| Regression | 12.388 | 4 | 3.097 | 18.803 | .000† | modPC 752.6/5.58 | −.196 | .021 |
| Residual | 22.730 | 138 | .165 | | | GM3 18:0 | −.391 | .000 |
| Total | 35.119 | 142 | | | | DG 18:1 20:0 | −.206 | .015 |
| | | | | | | SM 18:0 | .449 | .000 |

TABLE 11-continued

Analysis of variance[a] of stable vs unstable cohort

| | ANOVA | | | | Covariates | | |
|---|---|---|---|---|---|---|---|
| | Sum of Squares | df | Mean Square | F | Sig. | Variable | Partial Correlation | Sig |

| | Sum of Squares | df | Mean Square | F | Sig. | Variable | Partial Correlation | Sig |
|---|---|---|---|---|---|---|---|---|
| Model 3 (lipids + traditional risk factors) $R^2 = 0.473$ | | | | | | | | |
| Regression | 12.604 | 6 | 2.101 | 14.972 | .000[†] | CRP | .516 | .000 |
| Residual | 14.031 | 100 | .140 | | | PI 34:0 | −.280 | .004 |
| Total | 26.636 | 106 | | | | DHC 18:1 | .250 | .011 |
| | | | | | | modCer 703.6/5.87 | .247 | .012 |
| | | | | | | SM 22:1 | .327 | .001 |
| | | | | | | GM3 18:0 | −.225 | .023 |

[a]linear regression analysis was performed for ANOVA

TABLE 12

Analysis of variance[a] of control vs CAD cohort

| | Sum of Squares | df | Mean Square | F | Sig. | Variable | Partial Correlation | Sig |
|---|---|---|---|---|---|---|---|---|
| Model 4 (traditional risk factors) $R2 = 0.577$ | | | | | | | | |
| Regression | 22.181 | 7 | 3.169 | 30.980 | .000 | hypertension | .492 | .000 |
| Residual | 16.263 | 159 | .102 | | | CRP | .382 | .000 |
| Total | 38.443 | 166 | | | | smoker | .313 | .000 |
| | | | | | | sex (0 = M) | −.302 | .000 |
| | | | | | | trigs | .260 | .001 |
| | | | | | | gluc | .163 | .039 |
| | | | | | | age | .162 | .040 |
| Model 5 (lipids) $R2 = 0.809$ | | | | | | | | |
| Regression | 35.114 | 25 | 1.405 | 32.700 | .000 | modPC 580.4/4.84 | −.280 | .000 |
| Residual | 7.646 | 178 | .043 | | | PS 40:6 | −.439 | .000 |
| Total | 42.760 | 203 | | | | modPC 752.6/5.58 | −.505 | .000 |
| | | | | | | APC 32:1 | −.333 | .000 |
| | | | | | | oddPC 37:3 | .326 | .000 |
| | | | | | | GM3 24:1 | .313 | .000 |
| | | | | | | oddPC 33:0 | −.234 | .001 |
| | | | | | | APC 36:0 | .218 | .003 |
| | | | | | | CE 24:3 | −.310 | .000 |
| | | | | | | SM 20:1 | .382 | .000 |
| | | | | | | SM 18:0 | −.320 | .000 |
| | | | | | | LPC 20:0 | −.311 | .000 |
| | | | | | | modCE 682.7/8.76 | .351 | .000 |
| | | | | | | COH | −.240 | .001 |
| | | | | | | Cer 20:0 | .218 | .003 |
| | | | | | | LPC 16:1 | .336 | .000 |
| | | | | | | TG 16:1 16:1 16:1 | −.285 | .000 |
| | | | | | | modPC 564.4/4.70 | −.245 | .001 |
| | | | | | | modPC 720.6/4.52 | −.212 | .004 |
| | | | | | | modPC 608.4/5.33 | .162 | .028 |
| | | | | | | PE 38:3 | −.217 | .003 |
| | | | | | | PE 38:1 | .158 | .032 |
| Model 6 (lipids + traditional risk factors) $R2 = 0.904$ | | | | | | | | |
| Regression | 34.443 | 26 | 1.325 | 46.359 | .000 | modPC 580.4/4.84 | −.713 | .000 |
| Residual | 4.001 | 140 | .029 | | | hypertension | .638 | .000 |
| Total | 38.443 | 166 | | | | PS 40:6 | −.387 | .000 |
| | | | | | | GM3 22:0 | .462 | .000 |
| | | | | | | PC 37:3 | .616 | .000 |
| | | | | | | PC 33:0 | −.219 | .009 |
| | | | | | | modPC 788.6/5.19 | .409 | .000 |
| | | | | | | C24.3 | −.372 | .000 |
| | | | | | | C24.4 | .481 | .000 |
| | | | | | | modPC 666.4/2.99 | .323 | .000 |
| | | | | | | PG 16:1 18:1 | −.303 | .000 |
| | | | | | | diabetes | −.238 | .005 |

TABLE 12-continued

Analysis of variance[a] of control vs CAD cohort

| ANOVA | | | | | Covariates | | |
|---|---|---|---|---|---|---|---|
| Sum of Squares | df | Mean Square | F | Sig. | Variable | Partial Correlation | Sig |
| | | | | | gluc | .253 | .002 |
| | | | | | modPC 678.4/4.37 | −.282 | .001 |
| | | | | | smoker | .234 | .005 |
| | | | | | modCer 731.6/6.22 | −.452 | .000 |
| | | | | | SM 18:1 | .429 | .000 |
| | | | | | sex | −.401 | .000 |
| | | | | | APC 36:5 | −.376 | .000 |
| | | | | | modPC 769.6/6.25 | .428 | .000 |
| | | | | | APC 36:3 | −.449 | .000 |
| | | | | | oddPC 35:4 | −.365 | .000 |
| | | | | | PG 18:1 18:1 | −.367 | .000 |
| | | | | | TG 18:1 18:1 18:2 | .211 | .012 |
| | | | | | modPC 881.7/6.05 | −.326 | .000 |
| | | | | | CE 17:0 | −.239 | .004 |
| | | | | | PI 38:5 | .213 | .011 |

[a]linear regression analysis was performed for ANOVA

TABLE 13

Ranked list of analytes based on recursive feature elimination of stable CAD vs unstable CAD
Stable vs Unstable

| | Lipids Only | | Lipids and Traditional risk Factors | |
|---|---|---|---|---|
| # | Analyte | Asymp. Sig. (2-tailed) | Analyte | Asymp. Sig. (2-tailed) |
| 1 | modPC 752.5/5.58 | 3.59E−06 | CRP | |
| 2 | modCer 731.6/6.22 | 6.78E−05 | modPC 752.5/5.58 | 3.59E−06 |
| 3 | DHC 18:1 | 6.59E−03 | modCer 731.6/6.22 | 6.78E−05 |
| 4 | APC 34:2 | 3.27E−03 | DHC 18:1 | 6.59E−03 |
| 5 | SM 18:0 | 8.04E−05 | SM 18:0 | 8.04E−05 |
| 6 | GM3 18:0 | 4.64E−02 | APC 34:2 | 3.27E−03 |
| 7 | LPC 16:1 | 1.52E−04 | GM3 18:0 | 4.64E−02 |
| 8 | DG 18:1 20:0 | 1.81E−04 | DG 18:1 20:0 | 1.81E−04 |
| 9 | Cer 18:1 | 1.62E−04 | PI 36:1 | 1.70E−04 |
| 10 | PI 36:1 | 1.70E−04 | Cer 18:1 | 1.62E−02 |
| 11 | PC 34:3 | 6.41E−04 | LPC 16:1 | 1.52E−04 |
| 12 | LPC 14:0 | 1.03E−05 | PC 34:3 | 6.41E−04 |
| 13 | PI 36:3 | 2.50E−04 | PI 36:3 | 2.50E−04 |
| 14 | modPC 745.5/6.35 | 7.35E−03 | APC 36:0 | 7.31E−01 |
| 15 | APC 36:0 | 7.31E−01 | LPC 14:0 | 1.03E−05 |
| 16 | PI 38:2 | 1.24E−03 | modPC 745.5/6.35 | 7.35E−03 |
| 17 | SM 18:1 | 2.25E−03 | PI 38:2 | 1.24E−03 |
| 18 | Cer 18:0 | 7.72E−03 | SM 18:1 | 2.25E−03 |
| 19 | PG 18:1 18:1 | 1.03E−01 | modPC 622.4/4.54 | 9.84E−01 |
| 20 | modCer 910.8/8.98 | 4.87E−02 | modCer 703.6/5.87 | 8.08E−01 |
| 21 | modPC 622.4/4.54 | 9.84E−01 | LDL | |
| 22 | modPC 736.5/5.38 | 9.46E−03 | PG 18:1 18:1 | 1.03E−01 |
| 23 | modPC 608.4/5.33 | 2.17E−03 | modPC 736.5/5.38 | 9.46E−03 |
| 24 | modPC 703.6/5.87 | 8.08E−01 | modPC 608.4/5.33 | 2.17E−03 |
| 25 | DHC 22:0 | 3.34E−01 | modPC 743.5/5.91 | 2.73E−02 |
| 26 | LPC 18:1 | 2.48E−04 | THC 18:0 | 2.09E−01 |
| 27 | THC 18:0 | 2.09E−01 | PI 34:0 | 5.68E−03 |
| 28 | modPC 743.5/5.91 | 2.73E−02 | DHC 22:0 | 3.34E−01 |
| 29 | modPC 694.4/6.20 | 5.77E−02 | DG 16:0 20:0 | 2.41E−03 |
| 30 | modPC 692.4/5.05 | 5.38E−02 | total_cholesterol | |
| 31 | TG 16:1 16:1 16:1 | 1.09E−03 | TG 16:1 16:1 16:1 | 1.09E−03 |
| 32 | PI 34:0 | 5.68E−03 | smoker_cont | |
| 33 | DG 16:0 20:0 | 2.41E−03 | SM 22:0 | 1.20E−01 |
| 34 | SM 22:0 | 1.20E−01 | hist_of_CAD | |
| 35 | modPC 690.4/6.00 | 1.25E−01 | modPC 692.4/5.52 | 4.43E−05 |
| 36 | LPC 18:2 | 2.16E−03 | Cer 18:0 | 7.72E−03 |
| 37 | modPC 678.4/5.51 | 1.21E−05 | LPC 18:1 | 2.48E−04 |
| 38 | modPC 692.4/5.52 | 4.43E−05 | modPC 694.4/6.20 | 5.77E−02 |
| 39 | modPC 878.6/5.98 | 2.33E−01 | TG 14:0 16:1 18:1 | 1.09E−03 |
| 40 | TG 14:0 16:1 18:1 | 1.09E−03 | age | |
| 41 | PE 32:0 | 2.18E−01 | modPC 690.4/6.00 | 1.25E−01 |
| 42 | PI 38:3 | 3.38E−02 | PE 36:0 | 9.16E−01 |
| 43 | TG 14:1 18:0 18:2 | 6.67E−03 | modPC 692.4/5.05 | 5.38E−02 |
| 44 | modPC 580.4/4.84 | 5.75E−03 | PE 32:0 | 2.18E−01 |
| 45 | PC 40:6 | 2.44E−01 | SM 22:1 | 1.66E−01 |
| 46 | modCer 886.8/9.06 | 1.48E−01 | modPC 678.4/5.51 | 1.21E−05 |
| 47 | modPC 818.6/6.10 | 1.34E−01 | hypertension | |
| 48 | THC 18:1 | 9.22E−01 | LPC 18:2 | 2.16E−03 |
| 49 | DHC 16:0 | 9.13E−02 | sex | |
| 50 | PC 32:0 | 6.50E−01 | modCer 910.8/8.98 | 4.87E−02 |
| 51 | PE 36:0 | 9.16E−01 | DHC 16:0 | 9.13E−02 |
| 52 | TG 14:0 16:1 18:2 | 1.12E−03 | TG 14:0 16:1 18:2 | 1.12E−03 |
| 53 | CE 14:0 | 1.46E−03 | CE 14:0 | 1.46E−03 |
| 54 | modPC 769.5/6.25 | 1.53E−01 | PI 40:4 | 1.54E−02 |
| 55 | MHC 20:0 | 1.34E−01 | TG 14:1 18:0 18:2 | 6.67E−03 |
| 56 | APC 36:4 | 1.46E−01 | APC 36:5 | 2.77E−01 |
| 57 | PG 16:0 18:1 | 2.88E−01 | modPC 878.6/5.98 | 2.33E−01 |
| 58 | modCer 875.7/9.23 | 3.49E−02 | modPC 769.5/6.25 | 1.53E−01 |
| 59 | APC 36:5 | 2.77E−01 | modCer 798.7/7.29 | 4.18E−01 |
| 60 | PI 36:4 | 5.64E−03 | PC 40:6 | 2.44E−01 |
| 61 | DG 18:1 20:3 | 8.34E−02 | APC 36:4 | 1.46E−01 |
| 62 | modCer 614.6/5.72 | 6.15E−02 | PI 38:3 | 3.38E−02 |
| 63 | TG 16:1 18:1 18:1 | 1.27E−01 | modCer 875.7/9.23 | 3.49E−02 |
| 64 | modPC 816.6/5.58 | 9.25E−01 | PG 16:0 18:1 | 2.88E−01 |
| 65 | PI 40:4 | 1.54E−02 | modPC 580.4/4.84 | 5.75E−03 |
| 66 | modPC 704.5/3.81 | 7.74E−01 | TG 16:1 18:1 18:1 | 1.27E−01 |
| 67 | modPC 692.4/6.10 | 6.80E−02 | PI 40:6 | 1.43E−01 |
| 68 | PI 40:6 | 1.43E−01 | THC 18:1 | 9.22E−01 |
| 69 | modPC 881.6/6.05 | 5.98E−02 | modPC 818.6/6.10 | 1.34E−01 |
| 70 | PS 36:2 | 4.61E−02 | modPC 594.4/3.26 | 5.85E−01 |
| 71 | modPC 566.4/5.10 | 1.99E−01 | modCer 886.8/9.06 | 1.48E−01 |
| 72 | SM 22:1 | 1.66E−01 | PC 32:0 | 6.50E−01 |
| 73 | modCer 798.7/7.29 | 4.18E−01 | PI 36:4 | 5.64E−03 |
| 74 | PS 38:5 | 4.99E−01 | PI 32:0 | 6.15E−02 |
| 75 | DHC 24:1 | 2.82E−01 | modPC 881.6/6.05 | 5.98E−02 |
| 76 | CE 15:0 | 2.84E−01 | TG 17:0 18:1 18:1 | 3.97E−01 |
| 77 | PC 30:2 | 1.53E−01 | DG 18:1 20:3 | 8.34E−02 |
| 78 | modPC 818.6/6.48 | 8.55E−01 | PE 34:1 | 1.55E−01 |
| 79 | LPC 20:5 | 1.21E−02 | MHC 20:0 | 1.34E−01 |
| 80 | PE 34:1 | 1.55E−01 | modPC 704.5/3.81 | 7.74E−01 |

TABLE 13-continued

Ranked list of analytes based on recursive feature elimination of stable CAD vs unstable CAD
Stable vs Unstable

| # | Analyte (Lipids Only) | Asymp. Sig. (2-tailed) | Analyte (Lipids and Traditional risk Factors) | Asymp. Sig. (2-tailed) |
|---|---|---|---|---|
| 81 | PE 38:2 | 4.68E−01 | modPC 816.6/5.58 | 9.25E−01 |
| 82 | oddPC 35:0 | 4.64E−02 | CE 17:1 | 4.96E−02 |
| 83 | oddPC 37:5 | 1.34E−01 | PE 38:2 | 4.68E−01 |
| 84 | oddPC 37:4 | 2.89E−01 | LPC 20:3 | 2.47E−02 |
| 85 | TG 14:1 18:1 18:1 | 1.81E−02 | TG 14:1 18:1 18:1 | 1.81E−02 |
| 86 | THC 24:0 | 3.56E−01 | oddPC 37:4 | 2.89E−01 |
| 87 | GM3 20:0 | 4.46E−01 | HDL | |
| 88 | PS 40:6 | 3.59E−01 | oddPC 35:0 | 4.64E−02 |
| 89 | CE 22:2 | 3.45E−01 | modPC 818.6/6.48 | 8.55E−01 |
| 90 | TG 14:0 18:2 18:2 | 4.17E−02 | CE 15:0 | 2.84E−01 |
| 91 | PI 32:0 | 6.15E−01 | modPC 692.4/6.10 | 6.80E−02 |
| 92 | DG 16:0 22:6 | 5.30E−01 | TG 16:0 16:1 18:1 | 3.89E−02 |
| 93 | TG 16:1 16:1 18:0 | 3.63E−03 | oddPC 37:5 | 1.34E−01 |
| 94 | PE 34:2 | 5.44E−01 | PG 18:0 18:1 | 2.63E−01 |
| 95 | DG 16:0 18:2 | 3.90E−01 | modCer 614.6/5.72 | 6.15E−02 |
| 96 | PI 38:5 | 3.88E−03 | TG 14:0 18:2 18:2 | 4.17E−02 |
| 97 | TG 17:0 18:1 18:1 | 3.97E−01 | TG 16:1 16:1 18:0 | 3.63E−03 |
| 98 | CE 16:2 | 1.77E−02 | PS 38:4 | 3.79E−01 |
| 99 | LPC 20:3 | 2.47E−02 | oddPC 33:1 | 5.71E−02 |
| 100 | CE 22:5 | 3.43E−01 | THC 24:0 | 3.56E−01 |
| 101 | PE 36:5 | 4.31E−02 | PC 36:5 | 4.27E−02 |
| 102 | modPC 594.4/3.26 | 5.85E−02 | DG 16:0 18:2 | 3.90E−01 |
| 103 | modPC 706.5/3.79 | 7.41E−01 | PI 38:6 | 4.05E−02 |
| 104 | CE 17:1 | 4.96E−02 | PS 36:2 | 4.61E−01 |
| 105 | PI 38:6 | 4.05E−02 | PE 34:2 | 5.44E−01 |
| 106 | PC 36:2 | 3.25E−02 | modPC 608.4/3.84 | 5.85E−02 |
| 107 | modPC 828.6/6.03 | 9.12E−01 | CE 16:2 | 1.77E−02 |
| 108 | PG 18:0 18:1 | 2.63E−01 | DHC 24:1 | 2.82E−01 |
| 109 | DHC 20:0 | 5.94E−01 | PC 36:2 | 3.25E−02 |
| 110 | CE 24:5 | 7.31E−01 | PC 40:5 | 7.11E−01 |
| 111 | modCer 632.6/9.22 | 9.74E−01 | TG 14:0 18:0 18:1 | 2.47E−03 |
| 112 | oddPC 35:3 | 1.10E−01 | modPC 592.4/5.10 | 4.13E−02 |
| 113 | LPC 20:0 | 4.38E−02 | PG 16:1 18:1 | 6.56E−01 |
| 114 | CE 22:3 | 5.33E−01 | PE 36:5 | 4.31E−02 |
| 115 | modPC 510.3/4.00 | 9.00E−01 | PS 38:5 | 4.99E−01 |
| 116 | DG 18:1 20:4 | 8.42E−01 | LPC 20:1 | 6.72E−01 |
| 117 | APC 36:2 | 3.28E−01 | modPC 828.6/6.03 | 9.12E−01 |
| 118 | PC 36:4 | 7.40E−01 | PI 38:5 | 3.88E−03 |
| 119 | TG 17:0 18:1 14:0 | 8.41E−02 | gluc | |
| 120 | CE 22:6 | 2.95E−01 | PI 36:0 | 1.58E−01 |
| 121 | modPC 538.3/4.10 | 3.18E−02 | DG 16:0 22:6 | 5.30E−01 |
| 122 | APC 34:0 | 5.32E−01 | modPC 650.4/3.94 | 4.40E−01 |
| 123 | modCer 766.6/7.17 | 3.36E−01 | CE 22:5 | 3.43E−01 |
| 124 | modPC 801.6/6.70 | 2.61E−01 | TG 18:0 18:0 18:0 | 2.81E−02 |
| 125 | PC 40:5 | 7.11E−01 | COH | 3.23E−01 |
| 126 | modPC 843.6/7.10 | 9.24E−01 | PC 38:6 | 5.15E−01 |
| 127 | modCE 682.7/8.76 | 1.10E−01 | BMI | |
| 128 | PC 38:6 | 5.15E−01 | APC 36:3 | 1.20E−01 |
| 129 | PC 32:1 | 2.78E−01 | oddPC 35:3 | 1.10E−01 |
| 130 | TG 16:1 18:1 18:2 | 4.22E−01 | oddPC 31:0 | 2.75E−02 |
| 131 | PG 16:1 18:1 | 6.56E−01 | APC 32:1 | 5.20E−01 |
| 132 | modCer 921.8/9.05 | 8.05E−01 | diabetes | |
| 133 | BMP 18:1 18:1 | 3.18E−02 | modPC 590.4/4.80 | 7.35E−01 |
| 134 | modPC 608.4/3.84 | 5.85E−02 | TG 17:0 18:1 14:0 | 8.41E−02 |
| 135 | PC 38:4 | 9.71E−01 | CE 20:1 | 8.64E−01 |
| 136 | THC 20:0 | 6.53E−01 | THC 22:0 | 4.78E−01 |
| 137 | PC 34:2 | 4.58E−01 | TG 17:0 18:1 16:1 | 2.71E−01 |
| 138 | modPC 650.4/3.94 | 4.40E−01 | CE 20:2 | 4.58E−01 |
| 139 | TG 18:0 18:0 18:0 | 2.81E−02 | PE 40:7 | 8.07E−01 |
| 140 | modPC 703.5/4.09 | 4.39E−01 | MHC 18:1 | 3.37E−01 |
| 141 | PI 34:1 | 6.27E−03 | PC 30:2 | 1.53E−01 |
| 142 | PS 38:4 | 3.79E−01 | CE 24:2 | 5.17E−01 |
| 143 | modPC 720.5/4.52 | 9.00E−01 | modPC 843.6/7.10 | 9.24E−01 |
| 144 | modPC 773.6/6.47 | 3.36E−01 | modPC 566.4/5.10 | 1.99E−01 |
| 145 | PE 38:1 | 5.32E−01 | modPC 678.4/4.37 | 7.35E−01 |
| 146 | DG 16:0 16:0 | 6.99E−01 | APC 36:2 | 3.28E−01 |
| 147 | DHC 24:0 | 8.55E−01 | GM3 16:0 | 7.71E−01 |
| 148 | TG 17:0 16:0 18:0 | 1.31E−01 | GM3 20:0 | 4.46E−01 |
| 149 | modPC 552.4/3.90 | 5.30E−02 | CE 24:3 | 9.64E−01 |
| 150 | THC 22:0 | 4.78E−01 | DG 18:2 18:2 | 1.01E−01 |
| 151 | oddPC 31:0 | 2.75E−02 | THC 20:0 | 6.53E−01 |
| 152 | GM3 24:1 | 3.71E−01 | CE 24:4 | 7.63E−01 |
| 153 | DG 18:0 18:0 | 6.48E−01 | modPC 720.5/4.52 | 9.00E−01 |
| 154 | CE 20:1 | 8.64E−01 | modPC 706.5/3.79 | 7.41E−01 |
| 155 | modPC 678.4/4.37 | 7.35E−01 | modPC 773.6/6.47 | 3.36E−01 |
| 156 | PE 36:3 | 3.68E−01 | GM3 24:1 | 3.71E−01 |
| 157 | DHC 18:0 | 5.33E−01 | PC 36:4 | 7.40E−01 |
| 158 | TG 16:0 16:1 18:1 | 3.89E−02 | MHC 16:0 | 5.71E−01 |
| 159 | oddPC 33:1 | 5.71E−02 | APC 34:1 | 8.95E−01 |
| 160 | modPC 590.4/4.80 | 7.35E−01 | modPC 510.3/4.00 | 9.00E−01 |
| 161 | modPC 592.4/5.10 | 4.13E−02 | modPC 650.4/3.24 | 9.71E−01 |
| 162 | modPC 610.4/2.03 | 4.95E−01 | trigs | |
| 163 | APC 36:3 | 1.20E−01 | CE 24:5 | 7.31E−01 |
| 164 | TG 14:0 18:0 18:1 | 2.47E−03 | APC 38:3 | 2.46E−01 |
| 165 | MHC 16:0 | 5.71E−01 | modPC 552.4/3.90 | 5.30E−02 |
| 166 | APC 34:1 | 8.95E−01 | TG 18:1 18:1 20:4 | 2.98E−01 |
| 167 | DG 14:0 16:0 | 2.33E−01 | TG 14:1 16:1 18:0 | 3.68E−03 |
| 168 | DG 18:1 18:2 | 3.38E−01 | PE 38:6 | 2.70E−01 |
| 169 | DG 14:0 18:2 | 4.42E−02 | TG 18:1 18:1 18:2 | 1.92E−01 |
| 170 | APC 36:1 | 9.53E−01 | modPC 610.4/2.03 | 4.95E−01 |
| 171 | DG 18:0 18:1 | 3.34E−01 | modPC 538.3/4.10 | 3.18E−02 |
| 172 | DG 16:0 22:5 | 8.90E−01 | TG 18:1 14:0 16:0 | 1.99E−03 |
| 173 | TG 16:1 16:1 18:1 | 4.51E−02 | PC 38:4 | 9.71E−01 |
| 174 | DG 16:1 18:1 | 1.09E−01 | PS 38:3 | 7.29E−01 |
| 175 | DG 18:0 18:2 | 8.39E−01 | CE 24:6 | 9.29E−01 |
| 176 | DG 14:0 18:1 | 1.12E−02 | TG 16:0 18:1 18:1 | 9.46E−01 |
| 177 | DG 16:0 18:1 | 9.74E−01 | modCE 588.5/7.94 | 8.39E−01 |
| 178 | modPC 666.4/2.99 | 9.58E−01 | DG 16:0 20:4 | 6.53E−01 |
| 179 | DG 16:0 20:3 | 3.85E−02 | PS 36:1 | 7.08E−01 |
| 180 | DG 16:0 20:4 | 6.53E−01 | CE 22:4 | 6.39E−01 |
| 181 | DG 18:1 18:3 | 3.03E−01 | modCE 790.8/6.57 | 6.60E−01 |
| 182 | CE 20:4 | 5.68E−01 | CE 22:0 | 4.39E−01 |
| 183 | CE 18:3 | 1.89E−02 | DG 16:0 18:0 | 1.14E−01 |
| 184 | TG 17:0 18:1 16:1 | 2.71E−01 | CE 22:1 | 7.63E−01 |
| 185 | Cer 22:0 | 8.16E−01 | APC 32:0 | 5.77E−01 |
| 186 | CE 20:5 | 3.88E−01 | PS 40:5 | 6.08E−01 |
| 187 | CE 18:0 | 7.08E−01 | CE 22:2 | 3.45E−01 |
| 188 | CE 18:2 | 9.25E−01 | DG 14:1 16:0 | 8.10E−03 |
| 189 | COH | 3.23E−01 | APC 36:1 | 9.53E−01 |
| 190 | TG 18:1 18:1 22:6 | 4.70E−01 | CE 24:0 | 2.63E−01 |
| 191 | TG 17:0 18:2 16:0 | 2.23E−01 | PS 40:6 | 3.59E−01 |
| 192 | CE 16:0 | 9.32E−01 | DG 18:1 18:3 | 3.03E−01 |
| 193 | CE 16:1 | 5.30E−02 | CE 18:2 | 9.25E−01 |
| 194 | CE 24:4 | 7.63E−01 | TG 17:0 16:0 16:1 | 7.84E−02 |
| 195 | modCE 790.8/6.57 | 6.60E−01 | modPC 690.4/4:90 | 1.94E−01 |
| 196 | CE 24:1 | 3.70E−01 | CE 22:3 | 5.33E−01 |
| 197 | CE 24:2 | 5.17E−01 | modCE 558.5/7.74 | 5.22E−01 |
| 198 | CE 24:3 | 9.64E−01 | DG 14:0 16:0 | 2.33E−01 |
| 199 | modCE 588.5/7.94 | 8.39E−01 | DG 14:0 18:2 | 4.42E−02 |
| 200 | Cer 16:0 | 5.66E−01 | DG 16:0 16:0 | 6.99E−01 |
| 201 | LPAF 16:0 | 1.99E−01 | TG 18:0 18:1 16:0 | 2.36E−01 |
| 202 | CE 22:4 | 6.39E−01 | TG 16:0 16:0 18:1 | 3.92E−01 |
| 203 | CE 20:2 | 4.58E−01 | TG 18:1 18:1 18:1 | 9.93E−01 |
| 204 | modCer 651.6/7.56 | 4.61E−01 | TG 18:1 18:1 22:6 | 4.70E−01 |
| 205 | CE 24:6 | 9.29E−01 | modPC 690.4/4.11 | 3.81E−01 |
| 206 | CE 22:0 | 4.39E−01 | Cer 20:0 | 4.01E−01 |
| 207 | TG 18:0 18:0 18:1 | 3.36E−01 | TG 14:1 16:0 18:1 | 3.16E−01 |
| 208 | TG 16:0 16:0 18:1 | 3.92E−01 | CE 16:1 | 5.30E−02 |
| 209 | Cer 24:1 | 6.78E−01 | PE 36:3 | 3.68E−01 |
| 210 | TG 16:0 16:0 18:2 | 9.77E−01 | TG 14:0 16:0 18:2 | 5.43E−03 |
| 211 | TG 18:0 18:1 18:1 | 4.80E−01 | oddPC 37:6 | 6.50E−01 |
| 212 | TG 15:0 18:1 18:1 | 6.37E−01 | TG 16:0 16:0 18:2 | 9.77E−01 |
| 213 | TG 16:0 16:0 18:0 | 1.13E−01 | TG 16:0 18:0 18:0 | 1.13E−01 |
| 214 | TG 14:1 16:1 18:0 | 3.68E−03 | TG 18:0 18:2 18:2 | 9.04E−01 |
| 215 | TG 14:1 16:0 18:1 | 3.16E−01 | TG 18:1 18:2 18:2 | 9.51E−01 |
| 216 | DG 18:0 20:4 | 8.61E−01 | DG 18:0 20:4 | 8.61E−01 |
| 217 | TG 17:0 16:0 16:1 | 7.84E−02 | TG 18:0 18:0 18:1 | 3.36E−01 |
| 218 | TG 15:0 18:1 16:0 | 5.94E−01 | TG 16:0 16:0 16:0 | 6.62E−02 |

TABLE 13-continued

Ranked list of analytes based on recursive feature elimination of stable CAD vs unstable CAD Stable vs Unstable

| | Lipids Only | | Lipids and Traditional risk Factors | |
|---|---|---|---|---|
| # | Analyte | Asymp. Sig. (2-tailed) | Analyte | Asymp. Sig. (2-tailed) |
| 219 | TG 16:0 16:0 16:0 | 6.62E-02 | TG 18:0 18:1 18:1 | 4.80E-01 |
| 220 | modCE 558.5/7.74 | 5.22E-01 | DG 16:1 18:1 | 1.09E-01 |
| 221 | CE 17:0 | 6.22E-01 | oddPC 31:1 | 1.95E-01 |
| 222 | TG 18:1 18:1 18:1 | 9.93E-01 | DG 18:1 18:1 | 9.38E-01 |
| 223 | TG 18:1 18:1 18:2 | 1.92E-01 | LPC 20:2 | 8.60E-03 |
| 224 | TG 18:2 18:2 20:4 | 7.76E-01 | CE 20:3 | 6.51E-01 |
| 225 | oddPC 37:3 | 5.99E-01 | DG 14:0 18:1 | 1.12E-02 |
| 226 | CE 22:1 | 7.63E-01 | DG 16:0 20:3 | 3.85E-02 |
| 227 | TG 16:0 18:1 18:2 | 1.94E-01 | TG 16:0 18:0 18:1 | 9.77E-01 |
| 228 | PE 38:5 | 9.03E-01 | TG 15:0 18:1 18:1 | 6.37E-01 |
| 229 | PI 32:1 | 3.30E-02 | DG 18:1 18:2 | 3.38E-01 |
| 230 | TG 18:0 18:2 18:2 | 9.04E-01 | APC 38:5 | 7.71E-01 |
| 231 | TG 18:2 18:2 18:2 | 9.77E-01 | CE 18:1 | 5.49E-01 |
| 232 | TG 16:0 18:0 18:1 | 9.77E-01 | CE 17:0 | 6.22E-01 |
| 233 | oddPC 31:1 | 1.95E-01 | CE 18:3 | 1.89E-02 |
| 234 | PC 44:12 | 8.13E-01 | DG 18:1 20:4 | 8.42E-01 |
| 235 | SM 20:1 | 9.32E-01 | CE 18:0 | 7.08E-01 |
| 236 | CE 24:0 | 2.63E-01 | CE 20:5 | 3.88E-01 |
| 237 | oddPC 33:2 | 9.48E-01 | DG 16:0 22:5 | 8.90E-01 |
| 238 | modPC 536.3/3.50 | 4.33E-02 | GM3 22:0 | 8.74E-01 |
| 239 | PC 38:5 | 9.11E-01 | DG 14:0 14:0 | 2.75E-03 |
| 240 | PC 34:1 | 4.41E-01 | PC 34:1 | 4.41E-01 |
| 241 | TG 16:0 18:1 18:1 | 9.46E-01 | CE 22:6 | 2.95E-01 |
| 242 | PC 32:2 | 2.91E-01 | PC 32:1 | 2.78E-01 |
| 243 | PC 36:3 | 7.95E-02 | CE 16:0 | 9.32E-01 |
| 244 | Cer 24:0 | 5.51E-01 | PC 36:3 | 7.95E-02 |
| 245 | PC 34:0 | 8.94E-02 | DG 18:0 18:0 | 6.48E-01 |
| 246 | modPC 690.4/4.90 | 1.94E-01 | PC 32:2 | 2.91E-01 |
| 247 | APC 32:0 | 5.77E-01 | oddPC 35:4 | 8.37E-01 |
| 248 | APC 32:1 | 5.20E-01 | modCer 651.6/7.56 | 4.61E-01 |
| 249 | modPC 772.5/5.37 | 8.77E-01 | modCer 632.6/9.22 | 9.74E-01 |
| 250 | DG 14:1 16:0 | 8.10E-03 | modCer 883.8/7.75 | 7.11E-01 |
| 251 | LPAF 18:0 | 7.62E-01 | modCer 769.6/8.01 | 4.71E-01 |
| 252 | oddPC 37:2 | 6.59E-01 | modCer 766.6/7.17 | 3.36E-01 |
| 253 | oddPC 35:2 | 8.93E-01 | modCer 666.4/2.99 | 9.58E-01 |
| 254 | CE 20:3 | 6.51E-01 | oddPC 37:2 | 6.59E-01 |
| 255 | oddPC 33:0 | 5.37E-01 | oddPC 37:3 | 5.99E-01 |
| 256 | PS 38:3 | 7.29E-01 | LPAF 18:0 | 7.62E-01 |
| 257 | oddPC 37:6 | 6.50E-01 | modCer 564.4/4.70 | 2.04E-01 |
| 258 | oddPC 35:1 | 5.99E-01 | APC 34:0 | 5.32E-01 |
| 259 | LPC 18:0 | 4.22E-01 | modCE 682.7/8.76 | 1.10E-01 |
| 260 | SM 15:0 | 2.13E-01 | CE 24:1 | 3.70E-01 |
| 261 | SM 16:1 | 2.54E-01 | oddPC 33:2 | 9.48E-01 |
| 262 | modCer 769.6/8.01 | 4.71E-01 | DG 18:0 18:1 | 3.34E-01 |
| 263 | THC 16:0 | 3.90E-01 | SM 15:0 | 2.13E-01 |
| 264 | TG 18:1 14:0 16:0 | 1.99E-03 | APC 38:4 | 8.74E-01 |
| 265 | MHC 24:0 | 2.85E-01 | oddPC 35:2 | 8.93E-01 |
| 266 | PC 36:5 | 4.27E-02 | LPC 20:5 | 1.21E-02 |
| 267 | Cer 20:0 | 4.01E-01 | DHC 20:0 | 5.94E-01 |
| 268 | TG 18:1 18:1 20:4 | 2.98E-01 | MHC 24:1 | 6.11E-01 |
| 269 | GM3 16:0 | 7.71E-01 | MHC 18:0 | 6.61E-01 |
| 270 | MHC 22:0 | 6.53E-01 | Cer 24:0 | 5.51E-01 |
| 271 | MHC 18:0 | 6.61E-01 | DHC 18:0 | 5.33E-01 |
| 272 | modCer 576.5/7.68 | 3.36E-01 | Cer 24:1 | 6.78E-01 |
| 273 | SM 24:0 | 6.11E-01 | MHC 24:0 | 2.85E-01 |
| 274 | SM 24:2 | 4.68E-01 | Cer 22:0 | 8.16E-01 |
| 275 | SM 16:0 | 2.27E-01 | TG 18:2 18:2 18:2 | 9.77E-01 |
| 276 | oddPC 35:4 | 8.37E-01 | TG 16:1 16:1 18:1 | 4.51E-02 |
| 277 | modPC 633.4/4.51 | 9.17E-01 | PC 34:2 | 4.58E-01 |
| 278 | modCer 883.8/7.75 | 7.11E-01 | TG 17:0 16:0 18:0 | 1.31E-01 |
| 279 | GM3 22:0 | 8.74E-01 | MHC 22:0 | 6.53E-01 |
| 280 | THC 24:1 | 8.12E-01 | modPC 506.3/3.50 | 3.35E-01 |
| 281 | MHC 18:1 | 3.37E-01 | modCer 576.5/7.68 | 3.36E-01 |
| 282 | SM 14:0 | 8.48E-01 | SM 16:0 | 2.27E-01 |
| 283 | GM3 24:0 | 8.58E-01 | SM 16:1 | 2.54E-01 |
| 284 | TG 14:0 16:0 18:2 | 5.43E-03 | SM 14:0 | 8.48E-01 |
| 285 | DG 14:0 14:0 | 2.75E-03 | SM 24:0 | 6.11E-01 |
| 286 | modPC 508.3/3.30 | 8.18E-01 | SM 24:1 | 7.49E-01 |
| 287 | PE 36:2 | 3.68E-01 | SM 20:1 | 9.32E-01 |
| 288 | APC 38:3 | 2.46E-01 | GM3 24:0 | 8.58E-01 |
| 289 | PE38:4 | 3.99E-01 | DG 18:0 18:2 | 8.39E-01 |
| 290 | PE 38:6 | 2.70E-01 | THC 16:0 | 3.90E-01 |
| 291 | PE 36:1 | 5.77E-01 | DHC 24:0 | 8.55E-01 |
| 292 | DG 18:0 16:1 | 5.30E-01 | PC 34:0 | 8.94E-02 |
| 293 | PC 40:7 | 9.16E-01 | THC 24:1 | 8.12E-01 |
| 294 | modPC 788.6/5.19 | 3.59E-01 | modPC 536.3/3.50 | 4.33E-02 |
| 295 | modPC 764.5/6.52 | 2.97E-01 | PC 38:5 | 9.11E-01 |
| 296 | SM 24:1 | 7.49E-01 | BMP 18:1 18:1 | 3.18E-01 |
| 297 | modPC 866.6/7.24 | 3.19E-01 | APC 38:2 | 9.98E-01 |
| 298 | LPC 20:2 | 8.60E-03 | modPC 866.6/7.24 | 3.19E-01 |
| 299 | PI 38:4 | 1.15E-01 | PE 36:4 | 7.05E-01 |
| 300 | PI 36:0 | 1.58E-01 | LPC 20:4 | 6.94E-01 |
| 301 | PI 36:2 | 9.61E-01 | PE 32:1 | 3.30E-01 |
| 302 | PS 40:5 | 6.08E-01 | PC 44:12 | 8.13E-01 |
| 303 | PS 36:1 | 7.08E-01 | TG 16:0 18:2 18:2 | 4.96E-01 |
| 304 | PI 40:5 | 2.13E-01 | PC 40:7 | 9.16E-01 |
| 305 | MHC 24:1 | 6.11E-01 | SM 24:2 | 4.68E-01 |
| 306 | PE 40:7 | 8.07E-01 | TG 17:0 18:2 16:0 | 2.23E-01 |
| 307 | DG 18:1 18:1 | 9.38E-01 | modPC 788.6/5.19 | 3.59E-01 |
| 308 | PE 38:3 | 6.28E-01 | modPC 772.5/5.37 | 8.77E-01 |
| 309 | DG 16:0 18:0 | 1.14E-01 | PI 40:5 | 2.13E-01 |
| 310 | TG 16:0 18:2 18:2 | 4.96E-01 | PI 34:1 | 6.27E-03 |
| 311 | PE 40:6 | 3.81E-01 | PE 40:6 | 3.81E-01 |
| 312 | LPAF 18:1 | 9.35E-01 | PE 38:1 | 5.32E-01 |
| 313 | LPC 22:6 | 9.87E-01 | Cer 16:0 | 5.66E-01 |
| 314 | LPC 20:1 | 6.72E-01 | PI 38:4 | 1.15E-01 |
| 315 | modPC 512.3/1.70 | 8.59E-01 | PI 36:2 | 9.61E-01 |
| 316 | PE 36:4 | 7.05E-01 | TG 16:1 18:1 18:2 | 4.22E-01 |
| 317 | modPC 506.3/3.50 | 3.35E-01 | LPC 18:0 | 4.22E-01 |
| 318 | LPC 20:4 | 6.94E-01 | PE 36:1 | 5.77E-01 |
| 319 | APC 38:4 | 8.74E-01 | PE 36:2 | 3.68E-01 |
| 320 | APC 38:5 | 7.71E-01 | PE 38:3 | 6.28E-01 |
| 321 | APC 38:6 | 9.90E-02 | PE38:4 | 3.99E-01 |
| 322 | LPC 15:0 | 2.48E-01 | PE 38:5 | 9.03E-01 |
| 323 | APC 38:2 | 9.98E-01 | modPC 508.3/3.30 | 8.18E-01 |
| 324 | PE 32:1 | 3.30E-01 | LPC 20:0 | 4.38E-01 |
| 325 | modPC 678.4/4.94 | 8.90E-01 | CE 20:4 | 5.68E-01 |
| 326 | LPC 16:0 | 4.34E-01 | DG 18:0 16:1 | 5.30E-02 |
| 327 | DG 18:2 18:2 | 1.01E-01 | modPC 801.6/6.70 | 2.61E-01 |
| 328 | TG 17:0 18:1 16:0 | 2.36E-01 | LPAF 18:1 | 9.35E-01 |
| 329 | modPC 564.4/4.70 | 2.04E-01 | LPAF 16:0 | 1.99E-01 |
| 330 | modPC 690.4/4.11 | 3.81E-01 | oddPC 33:0 | 5.37E-01 |
| 331 | modPC 664.4/4.22 | 8.71E-01 | PI 32:1 | 3.30E-02 |
| 332 | modPC 636.4/3.37 | 7.68E-01 | TG 16:0 18:1 18:2 | 1.94E-01 |
| 333 | CE 18:1 | 5.49E-01 | APC 38:6 | 9.90E-02 |
| 334 | TG 18:1 18:2 18:2 | 9.51E-01 | LPC 15:0 | 2.48E-01 |
| 335 | modPC 650.4/4.44 | 7.57E-01 | modPC 764.5/6.52 | 2.97E-01 |
| 336 | modPC 650.4/3.24 | 9.71E-01 | LPC 16:0 | 4.34E-01 |
| 337 | modPC 645.4/4.49 | 5.99E-01 | modPC 703.5/4.09 | 4.39E-01 |
| 338 | | | modPC 678.4/4.94 | 8.90E-01 |
| 339 | | | modPC 664.4/4.22 | 8.71E-01 |
| 340 | | | modPC 650.4/4.44 | 7.57E-01 |
| 341 | | | modCer 921.8/9.05 | 8.05E-01 |
| 342 | | | TG 18:2 18:2 20:4 | 7.76E-01 |
| 343 | | | DG 16:0 18:1 | 9.74E-01 |
| 344 | | | oddPC 35:1 | 5.99E-01 |
| 345 | | | TG 15:0 18:1 16:0 | 5.94E-01 |
| 346 | | | LPC 22:6 | 9.87E-01 |
| 347 | | | modPC 512.3/1.70 | 8.59E-01 |
| 348 | | | modPC 645.4/4.49 | 5.99E-01 |
| 349 | | | modPC 636.4/3.37 | 7.68E-01 |
| 350 | | | modPC 633.4/4.51 | 9.17E-01 |

TABLE 14

Ranked list of analytes based on recursive feature elimination of control vs CAD groups
Control vs CAD

| # | Analyte (Lipids Only) | Asymp. Sig. (2-tailed) | Analyte (Lipids and Traditional risk Factors) | Asymp. Sig. (2-tailed) |
|---|---|---|---|---|
| 1 | modPC 580.4/4.84 | 8.09E−20 | modPC 580.4/4.84 | 8.09E−20 |
| 2 | modPC 608.4/5.33 | 1.03E−16 | hypertension | |
| 3 | modPC 552.4/3.90 | 7.59E−17 | modPC 608.4/5.33 | 1.03E−16 |
| 4 | PS 40:6 | 1.33E−08 | PS 40:6 | 1.33E−08 |
| 5 | LPC 20:0 | 3.11E−16 | modPC 552.4/3.90 | 7.59E−17 |
| 6 | PS 40:5 | 1.93E−07 | LPC 20:0 | 3.11E−16 |
| 7 | PI 34:0 | 6.32E−10 | PS 40:5 | 1.93E−07 |
| 8 | Cer 20:0 | 1.30E−03 | PI 34:0 | 6.32E−10 |
| 9 | modPC 745.5/6.35 | 8.37E−13 | Cer 20:0 | 1.30E−03 |
| 10 | APC 34:2 | 2.05E−13 | modPC 745.5/6.35 | 8.37E−13 |
| 11 | modPC 678.4/5.51 | 9.51E−10 | modPC 678.4/5.51 | 9.51E−10 |
| 12 | Cer 18:0 | 1.31E−08 | Cer 18:0 | 1.31E−08 |
| 13 | PI 36:0 | 6.85E−06 | APC 34:2 | 2.05E−13 |
| 14 | modPC 752.5/5.58 | 2.07E−08 | smoker_cont | |
| 15 | modPC 878.6/5.98 | 2.22E−07 | modPC 752.5/5.58 | 2.07E−08 |
| 16 | LPC 20:3 | 3.85E−01 | modPC 881.6/6.05 | 9.82E−10 |
| 17 | modPC 692.4/5.52 | 4.67E−09 | PI 36:0 | 6.85E−06 |
| 18 | modPC 690.4/6.00 | 5.85E−08 | LPC 20:3 | 3.85E−01 |
| 19 | APC 38:6 | 2.12E−08 | modPC 878.6/5.98 | 2.22E−07 |
| 20 | oddPC 37:3 | 3.50E−01 | modPC 692.4/5.52 | 4.67E−09 |
| 21 | LPC 20:4 | 2.89E−01 | HDL | |
| 22 | CE 20:3 | 3.81E−04 | modPC 690.4/6.00 | 5.85E−08 |
| 23 | modPC 692.4/6.10 | 1.31E−09 | APC 38:6 | 2.12E−08 |
| 24 | modPC 881.6/6.05 | 9.82E−10 | modPC 866.6/7.24 | 6.08E−12 |
| 25 | modPC 736.5/5.38 | 8.95E−09 | trigs | |
| 26 | modCer 766.5/7.17 | 1.29E−10 | LPC 20:4 | 2.89E−01 |
| 27 | modCer 576.5/7.68 | 7.03E−03 | age | |
| 28 | modPC 866.6/7.24 | 6.08E−12 | gluc | |
| 29 | modPC 633.4/4.51 | 1.12E−07 | modPC 736.5/5.38 | 8.95E−09 |
| 30 | modPC 694.4/6.20 | 1.27E−07 | modPC 692.4/6.10 | 1.31E−09 |
| 31 | modPC 566.4/5.10 | 4.47E−10 | modCer 576.5/7.68 | 7.03E−03 |
| 32 | CE 20:1 | 8.86E−07 | modCer 766.5/7.17 | 1.29E−10 |
| 33 | LPC 22:6 | 1.40E−01 | CE 22:4 | 1.87E−02 |
| 34 | PE 32:0 | 6.27E−02 | DG 18:1 20:0 | 2.24E−04 |
| 35 | DG 18:1 20:0 | 2.24E−04 | oddPC 37:3 | 3.50E−01 |
| 36 | PS 38:5 | 4.80E−06 | PI 32:0 | 1.46E−07 |
| 37 | PI 32:0 | 1.46E−07 | modPC 694.4/6.20 | 1.27E−07 |
| 38 | CE 22:4 | 1.87E−02 | CE 20:3 | 3.81E−04 |
| 39 | modPC 720.5/4.52 | 5.16E−02 | PS 38:5 | 4.80E−06 |
| 40 | CE 22:2 | 1.46E−06 | modPC 720.5/4.52 | 5.16E−02 |
| 41 | APC 36:3 | 6.57E−08 | CE 24:3 | 3.62E−02 |
| 42 | CE 24:3 | 3.62E−02 | PE 32:0 | 6.27E−02 |
| 43 | modPC 706.5/3.79 | 5.96E−01 | hist_of_CAD | |
| 44 | Cer 18:1 | 6.00E−02 | APC 36:3 | 6.57E−08 |
| 45 | PI 36:1 | 1.46E−08 | DG 16:0 20:0 | 2.01E−03 |
| 46 | DG 18:1 20:4 | 7.00E−04 | modPC 566.4/5.10 | 4.47E−10 |
| 47 | Cer 16:0 | 1.83E−01 | CE 20:1 | 8.86E−07 |
| 48 | modPC 692.4/5.05 | 3.93E−06 | LPC 14:0 | 4.46E−09 |
| 49 | PC 38:4 | 1.84E−01 | modPC 633.4/4.51 | 1.12E−07 |
| 50 | CE 22:0 | 4.68E−06 | modPC 706.5/3.79 | 5.96E−01 |
| 51 | CE 17:1 | 2.32E−01 | LPC 22:6 | 1.40E−01 |
| 52 | PE 36:0 | 1.62E−02 | modPC 692.4/5.05 | 3.93E−06 |
| 53 | THC 24:0 | 3.72E−08 | modCer 798.7/7.29 | 1.63E−08 |
| 54 | GM3 24:1 | 2.32E−01 | TG 14:0 18:2 18:2 | 2.22E−05 |
| 55 | DG 16:0 20:0 | 2.01E−03 | CE 22:2 | 1.46E−06 |
| 56 | SM 22:0 | 1.84E−07 | PI 36:1 | 1.46E−08 |
| 57 | modCer 614.6/5.72 | 1.43E−05 | CRP | |
| 58 | GM3 18:0 | 1.27E−07 | PC 38:4 | 1.84E−01 |
| 59 | PC 34:2 | 6.10E−05 | Cer 18:1 | 6.00E−02 |
| 60 | modPC 678.4/4.94 | 2.04E−04 | PG 16:1 18:1 | 2.62E−02 |
| 61 | modPC 538.3/4.10 | 1.54E−11 | THC 24:0 | 3.72E−08 |
| 62 | APC 36:2 | 2.90E−08 | CE 22:0 | 4.68E−06 |
| 63 | SM 24:0 | 3.64E−09 | PC 34:2 | 6.10E−05 |
| 64 | modCer 798.7/7.29 | 1.63E−08 | sex | |
| 65 | modPC 704.5/3.81 | 1.63E−01 | APC 32:1 | 8.37E−05 |
| 66 | PG 16:1 18:1 | 2.62E−02 | PI 40:6 | 2.36E−04 |
| 67 | APC 32:1 | 8.37E−05 | modPC 678.4/4.94 | 2.04E−04 |
| 68 | TG 14:0 18:2 18:2 | 2.22E−05 | SM 14:0 | 3.96E−06 |
| 69 | DG 18:1 18:3 | 4.01E−01 | SM 24:2 | 7.53E−01 |
| 70 | SM 14:0 | 3.96E−06 | PE 36:0 | 1.62E−02 |
| 71 | LPC 14:0 | 4.46E−09 | modPC 538.3/4.10 | 1.54E−11 |
| 72 | PI 40:6 | 2.36E−04 | modPC 818.6/6.48 | 8.67E−06 |
| 73 | PI 36:2 | 2.12E−08 | CE 17:1 | 2.32E−01 |
| 74 | SM 24:2 | 7.53E−01 | total_cholesterol | |
| 75 | PI 38:6 | 1.65E−06 | BMI | |
| 76 | APC 38:2 | 3.63E−06 | modPC 512.3/1.70 | 1.84E−04 |
| 77 | Cer 24:0 | 8.83E−05 | SM 24:0 | 3.64E−09 |
| 78 | MHC 22:0 | 3.29E−10 | DG 18:1 20:4 | 7.00E−04 |
| 79 | TG 16:0 16:0 16:0 | 1.71E−01 | GM3 18:0 | 1.27E−07 |
| 80 | modPC 828.6/6.03 | 1.37E−06 | TG 14:0 16:0 18:2 | 3.95E−03 |
| 81 | modPC 818.6/6.48 | 8.67E−06 | LDL | |
| 82 | COH | 6.13E−06 | oddPC 37:6 | 2.97E−04 |
| 83 | PS 38:4 | 1.03E−04 | modPC 816.6/5.58 | 1.47E−01 |
| 84 | modPC 816.6/5.58 | 1.47E−01 | oddPC 37:4 | 9.35E−01 |
| 85 | modPC 590.4/4.80 | 2.70E−07 | PI 36:2 | 2.12E−08 |
| 86 | DG 18:1 18:2 | 3.86E−02 | COH | 6.13E−06 |
| 87 | modPC 512.3/1.70 | 1.84E−04 | modPC 818.6/6.48 | 9.05E−04 |
| 88 | modCer 632.6/9.22 | 1.65E−03 | modPC 590.4/4.80 | 2.70E−07 |
| 89 | APC 36:5 | 1.09E−05 | SM 22:0 | 1.84E−07 |
| 90 | DG 16:0 20:4 | 3.13E−03 | GM3 20:0 | 8.90E−02 |
| 91 | Cer 24:1 | 3.58E−02 | PI 38:6 | 1.65E−06 |
| 92 | TG 17:0 18:1 14:0 | 2.40E−01 | PC 34:0 | 6.12E−08 |
| 93 | LPC 18:2 | 5.85E−08 | APC 38:2 | 3.63E−06 |
| 94 | oddPC 37:4 | 9.35E−01 | modCer 614.6/5.72 | 1.43E−05 |
| 95 | LPC 20:2 | 4.26E−05 | PE 36:2 | 3.06E−02 |
| 96 | PC 34:0 | 6.12E−08 | APC 36:2 | 2.90E−08 |
| 97 | modPC 769.5/6.25 | 3.34E−05 | LPC 18:2 | 5.85E−08 |
| 98 | PE 36:3 | 1.09E−02 | modPC 828.6/6.03 | 1.37E−06 |
| 99 | TG 14:0 16:0 18:2 | 3.95E−03 | TG 18:1 14:0 16:0 | 6.68E−03 |
| 100 | PG 18:1 18:1 | 1.61E−01 | modCer 632.6/9.22 | 1.65E−03 |
| 101 | SM 16:0 | 4.18E−07 | PS 38:4 | 1.03E−04 |
| 102 | modPC 690.4/4.90 | 3.69E−06 | APC 36:5 | 1.09E−05 |
| 103 | TG 14:0 18:0 18:1 | 1.14E−02 | PC 36:2 | 1.93E−07 |
| 104 | DG 14:0 14:0 | 3.42E−02 | GM3 22:0 | 3.69E−03 |
| 105 | DHC 24:1 | 5.91E−05 | CE 18:1 | 5.57E−01 |
| 106 | TG 16:0 16:0 18:0 | 3.31E−01 | MHC 16:0 | 1.72E−05 |
| 107 | TG 16:1 16:1 18:0 | 3.89E−03 | CE 18:3 | 4.06E−02 |
| 108 | GM3 20:0 | 8.90E−02 | PI 40:5 | 3.70E−03 |
| 109 | DHC 18:0 | 1.48E−01 | TG 18:1 18:1 18:2 | 6.44E−01 |
| 110 | DG 16:0 18:0 | 2.70E−01 | CE 20:2 | 4.11E−01 |
| 111 | DG 16:0 22:6 | 9.07E−01 | PI 38:4 | 4.81E−03 |
| 112 | TG 18:1 18:1 20:4 | 8.39E−01 | SM 16:1 | 2.89E−04 |
| 113 | PI 40:4 | 7.28E−02 | CE 18:0 | 5.23E−05 |
| 114 | PI 40:5 | 3.70E−03 | CE 20:5 | 1.27E−01 |
| 115 | APC 36:0 | 4.44E−04 | PE 40:6 | 4.98E−01 |
| 116 | TG 14:0 16:1 18:2 | 2.00E−03 | PI 38:2 | 6.25E−01 |
| 117 | SM 16:1 | 2.89E−04 | PI 36:4 | 2.11E−01 |
| 118 | PC 36:5 | 6.15E−03 | PS 38:3 | 5.49E−04 |
| 119 | GM3 16:0 | 8.99E−03 | CE 15:0 | 1.99E−01 |
| 120 | PI 38:4 | 4.81E−03 | CE 14:0 | 4.40E−01 |
| 121 | MHC 18:1 | 1.77E−01 | PE 36:1 | 7.00E−02 |
| 122 | DG 14:0 18:1 | 5.57E−01 | TG 16:0 16:1 18:1 | 8.32E−01 |
| 123 | PE 40:7 | 5.89E−02 | PI 38:3 | 3.08E−03 |
| 124 | PI 34:1 | 6.81E−05 | PS 36:2 | 4.37E−04 |
| 125 | DG 14:0 16:0 | 1.00E+00 | TG 16:1 16:1 18:1 | 9.23E−01 |
| 126 | PI 36:4 | 2.11E−04 | CE 17:0 | 3.40E−02 |
| 127 | DHC 16:0 | 1.78E−03 | CE 16:2 | 9.71E−02 |
| 128 | PI 32:1 | 3.81E−01 | PS 36:1 | 1.86E−02 |
| 129 | PE 40:6 | 4.98E−01 | CE 16:1 | 6.66E−02 |
| 130 | PS 36:1 | 1.86E−02 | TG 14:1 16:1 18:0 | 1.54E−01 |
| 131 | modPC 650.4/4.44 | 1.16E−01 | PE 38:1 | 1.80E−01 |
| 132 | DG 16:0 18:1 | 7.98E−04 | modCE 558.5/7.74 | 7.20E−01 |
| 133 | DG 16:0 18:2 | 4.88E−02 | PE 36:1 | 1.52E−01 |
| 134 | TG 16:0 18:1 18:1 | 2.16E−02 | PI 40:4 | 7.28E−02 |
| 135 | DG 18:0 18:2 | 1.06E−01 | CE 24:0 | 2.36E−04 |
| 136 | DG 14:0 18:2 | 1.02E−01 | PE 38:3 | 2.73E−01 |
| 137 | DG 18:1 18:1 | 3.85E−04 | modCE 682.7/8.76 | 1.05E−01 |
| 138 | CE 16:0 | 1.52E−01 | TG 18:2 18:2 20:4 | 8.59E−03 |

TABLE 14-continued

Ranked list of analytes based on recursive feature elimination of control vs CAD groups
Control vs CAD

| # | Lipids Only Analyte | Asymp. Sig. (2-tailed) | Lipids and Traditional risk Factors Analyte | Asymp. Sig. (2-tailed) | # | Lipids Only Analyte | Asymp. Sig. (2-tailed) | Lipids and Traditional risk Factors Analyte | Asymp. Sig. (2-tailed) |
|---|---|---|---|---|---|---|---|---|---|
| 139 | TG 16:1 18:1 18:2 | 5.72E-01 | modCE 790.8/6.57 | 7.29E-01 | 208 | oddPC 37:5 | 4.77E-03 | TG 16:0 18:0 18:1 | 3.35E-02 |
| 140 | CE 14:0 | 4.40E-01 | PE38:4 | 3.79E-01 | 209 | TG 16:0 18:1 18:2 | 4.47E-01 | TG 14:1 18:1 18:1 | 2.69E-02 |
| 141 | CE 16:2 | 9.71E-02 | PE 38:5 | 8.47E-01 | 210 | PC 38:5 | 4.96E-02 | modPC 594.4/3.26 | 6.48E-01 |
| 142 | CE 18:2 | 4.18E-01 | modCE 588.5/7.94 | 1.39E-01 | 211 | PG 18:0 18:1 | 6.13E-01 | modCer 886.8/9.06 | 2.15E-03 |
| 143 | TG 16:0 18:0 18:1 | 3.35E-02 | THC 16:0 | 3.96E-04 | 212 | PC 36:2 | 1.93E-07 | PC 32:2 | 2.26E-04 |
| 144 | CE 17:0 | 3.40E-02 | CE 22:1 | 3.67E-03 | 213 | modCer 886.8/9.06 | 2.15E-03 | PC 32:1 | 2.82E-01 |
| 145 | CE 18:3 | 4.06E-01 | CE 24:6 | 6.18E-01 | 214 | modCer 910.8/8.98 | 2.41E-01 | APC 32:0 | 1.91E-02 |
| 146 | TG 18:1 18:1 18:1 | 7.49E-02 | PI 38:5 | 2.13E-07 | 215 | modCer 875.7/9.23 | 5.21E-01 | DG 14:0 18:1 | 5.57E-01 |
| 147 | DG 16:0 22:5 | 3.31E-02 | CE 22:5 | 2.92E-01 | 216 | PE 36:4 | 5.06E-01 | modCer 921.8/9.05 | 6.07E-01 |
| 148 | TG 18:0 18:2 18:2 | 5.48E-02 | CE 22:3 | 5.45E-01 | 217 | PC 32:2 | 2.26E-04 | oddPC 31:0 | 2.02E-03 |
| 149 | TG 18:1 18:1 18:2 | 6.44E-01 | DG 16:0 18:1 | 7.98E-04 | 218 | PC 32:1 | 2.82E-01 | oddPC 37:2 | 1.71E-04 |
| 150 | PI 38:3 | 3.08E-03 | PI 34:1 | 6.81E-05 | 219 | modCer 921.8/9.05 | 6.07E-01 | PC 34:3 | 5.91E-06 |
| 151 | THC 20:0 | 6.00E-02 | TG 16:0 18:1 18:2 | 4.47E-01 | 220 | PC 38:6 | 1.01E-02 | SM 22:1 | 1.54E-05 |
| 152 | TG 18:0 18:0 18:0 | 1.49E-01 | CE 24:4 | 1.27E-01 | 221 | PC 40:7 | 2.57E-02 | DHC 18:1 | 2.94E-02 |
| 153 | TG 16:0 18:2 18:2 | 3.54E-02 | PI 36:3 | 1.40E-09 | 222 | oddPC 35:1 | 8.32E-01 | modCer 651.6/7.56 | 4.98E-05 |
| 154 | CE 18:0 | 5.23E-05 | TG 17:0 16:0 16:1 | 3.94E-01 | 223 | PE 38:5 | 8.47E-01 | modPC 608.4/3.84 | 9.87E-01 |
| 155 | CE 24:1 | 6.35E-03 | THC 18:0 | 1.31E-02 | 224 | oddPC 35:3 | 1.03E-03 | SM 24:1 | 5.29E-05 |
| 156 | modPC 703.5/4.09 | 1.23E-01 | TG 17:0 18:1 16:1 | 2.77E-01 | 225 | oddPC 35:2 | 2.74E-03 | TG 18:0 18:2 18:2 | 5.48E-02 |
| 157 | PI 36:3 | 1.40E-09 | TG 17:0 18:2 16:0 | 2.58E-01 | 226 | CE 24:0 | 2.36E-04 | modCer 883.8/7.75 | 1.30E-02 |
| 158 | CE 24:2 | 2.33E-03 | DG 18:1 20:3 | 1.87E-05 | 227 | PE 36:2 | 3.06E-02 | modCer 703.6/5.87 | 5.81E-01 |
| 159 | TG 17:0 18:1 16:1 | 2.77E-01 | TG 15:0 18:1 18:1 | 5.54E-01 | 228 | PC 34:3 | 5.91E-06 | modCer 769.6/8.01 | 6.38E-05 |
| 160 | modCE 790.8/6.57 | 7.29E-01 | TG 16:0 16:0 18:0 | 3.31E-01 | 229 | DG 14:1 16:0 | 4.28E-01 | oddPC 35:4 | 1.05E-01 |
| 161 | modCE 558.5/7.74 | 7.20E-01 | TG 14:0 16:1 18:2 | 2.00E-03 | 230 | PC 44:12 | 8.30E-01 | oddPC 35:3 | 1.03E-03 |
| 162 | modCE 588.5/7.94 | 1.39E-01 | TG 16:1 16:1 16:1 | 1.76E-03 | 231 | oddPC 31:1 | 9.66E-02 | oddPC 33:2 | 2.46E-04 |
| 163 | CE 22:6 | 4.71E-01 | DG 16:0 22:6 | 9.07E-01 | 232 | DHC 22:0 | 8.28E-05 | oddPC 33:1 | 9.87E-01 |
| 164 | CE 22:3 | 5.45E-01 | PC 32:0 | 6.40E-03 | 233 | PC 40:5 | 6.65E-01 | oddPC 35:0 | 3.74E-04 |
| 165 | CE 20:4 | 1.39E-01 | modPC 690.4/4.11 | 6.34E-02 | 234 | oddPC 33:1 | 9.87E-01 | oddPC 35:1 | 8.32E-01 |
| 166 | CE 20:2 | 4.11E-01 | TG 17:0 18:1 16:0 | 6.33E-01 | 235 | oddPC 33:0 | 5.09E-01 | oddPC 35:2 | 2.74E-03 |
| 167 | CE 24:6 | 6.18E-01 | Cer 24:0 | 8.83E-05 | 236 | PE 38:2 | 3.93E-01 | PE 38:6 | 6.74E-01 |
| 168 | CE 24:5 | 2.50E-02 | DG 16:0 22:5 | 3.31E-02 | 237 | modPC 772.5/5.37 | 5.97E-01 | PC 36:5 | 6.15E-03 |
| 169 | CE 22:5 | 2.92E-01 | TG 14:1 18:0 18:2 | 5.69E-03 | 238 | modCer 703.6/5.87 | 5.81E-01 | modPC 801.6/6.70 | 1.63E-05 |
| 170 | TG 18:1 14:0 16:0 | 6.68E-03 | TG 15:0 18:1 16:0 | 7.02E-01 | 239 | THC 16:0 | 3.96E-04 | PC 38:5 | 4.96E-02 |
| 171 | DG 16:0 20:3 | 6.49E-04 | TG 16:0 16:0 16:0 | 1.71E-01 | 240 | DHC 20:0 | 2.85E-01 | PC 36:4 | 9.22E-02 |
| 172 | TG 14:1 16:0 18:1 | 5.58E-01 | TG 16:0 16:0 18:2 | 6.94E-01 | 241 | PC 40:6 | 7.35E-01 | TG 17:0 16:0 18:0 | 8.68E-01 |
| 173 | TG 14:1 16:1 18:0 | 1.54E-01 | CE 24:1 | 6.35E-03 | 242 | TG 18:1 18:1 22:6 | 3.28E-01 | PC 44:12 | 8.30E-01 |
| 174 | TG 16:1 16:1 16:1 | 1.76E-03 | TG 17:0 18:1 14:0 | 2.40E-01 | 243 | THC 22:0 | 1.65E-02 | APC 38:3 | 3.73E-03 |
| 175 | PI 38:2 | 6.25E-04 | TG 18:1 18:1 22:6 | 3.28E-01 | 244 | THC 18:1 | 1.52E-01 | PC 40:6 | 7.35E-01 |
| 176 | LPAF 16:0 | 1.37E-05 | TG 16:1 16:1 18:0 | 3.89E-03 | 245 | THC 18:0 | 1.31E-02 | PC 40:5 | 6.65E-01 |
| 177 | TG 14:1 18:0 18:2 | 5.69E-03 | TG 14:1 16:0 18:1 | 5.58E-01 | 246 | SM 24:1 | 5.29E-05 | MHC 18:1 | 1.77E-01 |
| 178 | TG 15:0 18:1 16:0 | 7.02E-01 | TG 14:0 16:1 18:1 | 1.74E-03 | 247 | MHC 18:0 | 2.44E-01 | MHC 24:0 | 2.30E-09 |
| 179 | TG 17:0 16:0 16:1 | 3.94E-01 | TG 16:0 16:0 18:1 | 5.44E-01 | 248 | PE 38:1 | 1.80E-01 | DHC 16:0 | 1.78E-03 |
| 180 | DG 18:0 18:0 | 1.73E-01 | TG 18:1 18:1 20:4 | 8.39E-01 | 249 | MHC 16:0 | 1.72E-05 | MHC 20:0 | 2.35E-06 |
| 181 | modPC 843.6/7.10 | 2.76E-05 | PE 40:7 | 5.89E-01 | 250 | DHC 18:1 | 2.94E-02 | MHC 24:1 | 1.94E-04 |
| 182 | modCer 883.8/7.75 | 1.30E-02 | TG 14:0 18:0 18:1 | 1.14E-02 | 251 | PS 38:3 | 5.49E-04 | DHC 20:0 | 2.85E-01 |
| 183 | DG 18:0 18:1 | 2.76E-02 | modPC 743.5/5.91 | 9.86E-02 | 252 | MHC 20:0 | 2.35E-06 | GM3 16:0 | 8.99E-03 |
| 184 | modPC 818.6/6.48 | 9.05E-04 | DG 16:0 18:2 | 4.88E-02 | 253 | MHC 24:0 | 2.30E-09 | CE 20:4 | 1.39E-01 |
| 185 | DG 18:2 18:2 | 6.66E-01 | DG 16:0 16:0 | 1.46E-03 | 254 | THC 24:1 | 5.40E-03 | DHC 18:0 | 1.48E-01 |
| 186 | TG 18:0 18:1 18:1 | 4.75E-01 | CE 18:2 | 4.18E-01 | 255 | DG 16:0 16:0 | 1.46E-03 | DG 16:0 20:4 | 3.13E-03 |
| 187 | DG 18:0 20:4 | 5.68E-01 | DG 16:1 18:1 | 2.43E-03 | 256 | LPC 16:1 | 2.41E-03 | PC 40:7 | 2.57E-02 |
| 188 | TG 14:1 18:1 18:1 | 2.69E-02 | modCer 875.7/9.23 | 5.21E-01 | 257 | CE 22:1 | 3.67E-03 | CE 24:2 | 2.33E-03 |
| 189 | TG 16:1 18:1 18:1 | 9.50E-02 | PC 30:2 | 8.33E-03 | 258 | PI 38:5 | 2.13E-07 | diabetes | |
| 190 | PC 30:2 | 8.33E-03 | DG 14:0.16:0 | 1.00E+00 | 259 | SM 18:0 | 1.82E-01 | DG 14:0 18:2 | 1.02E-01 |
| 191 | TG 17:0 16:0 18:0 | 8.68E-01 | TG 18:0 18:0 18:0 | 1.49E-01 | 260 | modCer 769.6/8.01 | 6.38E-05 | LPC 18:1 | 1.48E-04 |
| 192 | TG 18:2 18:2 20:4 | 8.59E-03 | DG 14:1 16:0 | 4.28E-01 | 261 | DHC 24:0 | 7.02E-06 | APC 36:1 | 1.25E-03 |
| 193 | TG 17:0 18:1 18:1 | 1.09E-01 | PG 18:1 18:1 | 1.61E-01 | 262 | modCer 731.6/6.22 | 2.45E-02 | Cer 16:0 | 1.83E-01 |
| 194 | TG 18:2 18:2 18:2 | 1.11E-01 | TG 18:0 18:1 18:1 | 4.75E-01 | 263 | GM3 22:0 | 1.10E-05 | Cer 22:0 | 6.49E-02 |
| 195 | DG 16:1 18:1 | 2.43E-03 | TG 18:0 18:0 18:1 | 8.21E-01 | 264 | SM 15:0 | 1.50E-05 | GM3 24:0 | 1.10E-05 |
| 196 | CE 18:1 | 5.57E-01 | TG 16:0 18:2 18:2 | 3.54E-01 | 265 | GM3 22:0 | 3.69E-03 | TG 18:1 18:1 18:1 | 7.49E-02 |
| 197 | TG 18:0 18:0 18:1 | 8.21E-01 | TG 16:1 18:1 18:1 | 9.50E-02 | 266 | BMP 18:1 18:1 | 6.66E-01 | TG 18:1 18:2 18:2 | 9.40E-02 |
| 198 | TG 16:0 16:0 18:1 | 5.44E-01 | TG 16:0 18:1 18:1 | 2.16E-01 | 267 | APC 34:1 | 8.82E-03 | GM3 24:1 | 2.32E-01 |
| 199 | TG 16:0 16:0 18:2 | 6.94E-01 | DG 18:1 18:2 | 3.86E-02 | 268 | SM 22:1 | 1.54E-05 | modPC 650.4/3.94 | 1.47E-01 |
| 200 | TG 16:0 16:1 18:1 | 8.32E-01 | TG 16:1 18:1 18:2 | 5.72E-01 | 269 | modPC 510.3/4.00 | 3.18E-06 | SM 20:1 | 6.46E-02 |
| 201 | TG 17:0 18:2 16:0 | 2.58E-01 | APC 38:4 | 1.20E-02 | 270 | SM 18:1 | 3.83E-01 | SM 16:0 | 4.18E-07 |
| 202 | TG 17:0 18:1 16:0 | 6.33E-01 | DG 18:1 18:1 | 3.85E-01 | 271 | APC 32:0 | 1.91E-02 | SM 18:1 | 3.83E-01 |
| 203 | TG 15:0 18:1 18:1 | 5.54E-01 | DG 16:0 20:3 | 6.49E-04 | 272 | modPC 773.6/6.47 | 4.27E-04 | DHC 22:0 | 8.28E-05 |
| 204 | modCE 682.7/8.76 | 1.05E-01 | TG 17:0 18:1 18:1 | 1.09E-01 | 273 | modPC 788.6/5.19 | 8.85E-01 | modPC 506.3/3.50 | 1.09E-06 |
| 205 | PC 34:1 | 4.14E-01 | DG 16:0 18:0 | 2.70E-01 | 274 | modPC 764.5/6.52 | 7.95E-01 | THC 18:1 | 1.52E-01 |
| 206 | DG 18:0 16:1 | 6.20E-02 | DG 18:0 16:1 | 6.20E-02 | 275 | oddPC 33:2 | 2.46E-04 | LPC 15:0 | 6.06E-06 |
| 207 | PC 32:0 | 6.40E-03 | DG 18:2 18:2 | 6.66E-01 | 276 | DG 18:1 20:3 | 1.87E-05 | DHC 24:0 | 7.02E-06 |

TABLE 14-continued

Ranked list of analytes based on recursive feature elimination of control vs CAD groups
Control vs CAD

| | Lipids Only | | Lipids and Traditional risk Factors | |
|---|---|---|---|---|
| # | Analyte | Asymp. Sig. (2-tailed) | Analyte | Asymp. Sig. (2-tailed) |
| 277 | TG 14:0 16:1 18:1 | 1.74E-03 | THC 24:1 | 5.40E-03 |
| 278 | APC 38:3 | 3.73E-03 | PC 34:1 | 4.14E-01 |
| 279 | modPC 650.4/3.94 | 1.47E-01 | THC 20:0 | 6.00E-02 |
| 280 | modPC 666.4/2.99 | 4.06E-01 | THC 22:0 | 1.65E-03 |
| 281 | modPC 536.3/3.50 | 9.52E-05 | modPC 690.4/4.90 | 3.69E-06 |
| 282 | modPC 650.4/3.24 | 3.58E-02 | DG 18:1 18:3 | 4.01E-01 |
| 283 | modPC 664.4/4.22 | 4.26E-01 | modPC 536.3/3.50 | 9.52E-05 |
| 284 | CE 20:5 | 1.27E-01 | CE 22:6 | 4.71E-01 |
| 285 | PC 36:4 | 9.22E-02 | modPC 703.5/4.09 | 1.23E-01 |
| 286 | oddPC 35:4 | 1.05E-01 | modPC 764.5/6.52 | 7.95E-01 |
| 287 | modPC 690.4/4.11 | 6.34E-02 | PG 16:0 18:1 | 5.63E-01 |
| 288 | LPC 18:0 | 8.07E-07 | PI 32:1 | 3.81E-01 |
| 289 | PE 36:1 | 7.00E-02 | DHC 24:1 | 5.91E-05 |
| 290 | PE 38:6 | 6.74E-01 | modPC 610.4/2.03 | 4.62E-01 |
| 291 | TG 18:1 18:2 18:2 | 9.40E-02 | modPC 645.4/4.49 | 1.12E-05 |
| 292 | oddPC 37:2 | 1.71E-04 | SM 18:0 | 1.82E-01 |
| 293 | PE 38:3 | 2.73E-01 | PE 36:5 | 3.27E-02 |
| 294 | modPC 31:0 | 2.02E-03 | modPC 636.4/3.37 | 3.06E-01 |
| 295 | oddPC 37:6 | 2.97E-04 | PE 34:2 | 2.85E-01 |
| 296 | PE38:4 | 3.79E-01 | modPC 664.4/4.22 | 4.26E-01 |
| 297 | PG 16:0 18:1 | 5.63E-01 | modPC 650.4/4.44 | 1.16E-01 |
| 298 | PC 36:3 | 1.35E-01 | TG 18:2 18:2 18:2 | 1.11E-01 |
| 299 | oddPC 35:0 | 3.74E-01 | PE 32:1 | 6.92E-02 |
| 300 | modPC 608.4/3.84 | 9.87E-01 | modPC 769.5/6.25 | 3.34E-05 |
| 301 | PE 34:2 | 2.85E-01 | modPC 666.4/2.99 | 4.06E-01 |
| 302 | PE 36:5 | 3.27E-02 | PG 18:0 18:1 | 6.13E-01 |
| 303 | PE 32:1 | 6.92E-02 | modPC 622.4/4.54 | 6.84E-02 |
| 304 | TG 16:1 16:1 18:1 | 9.23E-01 | PE 36:4 | 5.06E-01 |
| 305 | LPC 16:0 | 4.68E-06 | modPC 678.4/4.37 | 1.16E-02 |
| 306 | LPC 18:1 | 1.48E-04 | PE 34:1 | 1.98E-01 |
| 307 | LPC 15:0 | 6.06E-06 | modPC 772.5/5.37 | 5.97E-01 |
| 308 | modCer 651.6/7.56 | 4.98E-05 | PC 38:6 | 1.01E-02 |
| 309 | modPC 743.5/5.91 | 9.86E-02 | PE 38:2 | 3.93E-01 |
| 310 | LPC 20:1 | 2.39E-05 | modPC 773.6/6.47 | 4.27E-04 |
| 311 | LPC 20:5 | 1.26E-02 | modPC 788.6/5.19 | 8.85E-01 |
| 312 | CE 15:0 | 1.99E-01 | modPC 704.5/3.81 | 1.63E-01 |
| 313 | modPC 678.4/4.37 | 1.16E-02 | BMP 18:1 18:1 | 6.66E-01 |
| 314 | CE 24:4 | 1.27E-01 | SM 15:0 | 1.50E-05 |
| 315 | SM 20:1 | 6.46E-02 | modCer 731.6/6.22 | 2.45E-02 |
| 316 | APC 34:0 | 1.20E-03 | APC 36:0 | 4.44E-04 |
| 317 | APC 38:4 | 1.20E-02 | oddPC 31:1 | 9.66E-02 |
| 318 | modPC 801.6/6.70 | 1.63E-05 | oddPC 33:0 | 5.09E-02 |
| 319 | APC 36:1 | 1.25E-03 | APC 38:5 | 7.35E-05 |
| 320 | APC 38:5 | 7.35E-05 | DG 18:0 18:1 | 2.76E-02 |
| 321 | MHC 24:1 | 1.94E-04 | LPC 16:0 | 4.68E-06 |
| 322 | modPC 594.4/3.26 | 6.48E-01 | LPAF 18:0 | 3.66E-05 |
| 323 | modPC 508.3/3.30 | 8.28E-05 | DG 14:0 14:0 | 3.42E-02 |
| 324 | Cer 22:0 | 6.49E-02 | LPC 16:1 | 2.41E-03 |
| 325 | modPC 592.4/5.10 | 5.49E-06 | oddPC 37:5 | 4.77E-03 |
| 326 | modPC 636.4/3.37 | 3.06E-01 | modCer 910.8/8.98 | 2.41E-01 |
| 327 | modPC 645.4/4.49 | 1.12E-05 | APC 34:1 | 8.82E-03 |
| 328 | modPC 610.4/2.03 | 4.62E-01 | modPC 843.6/7.10 | 2.76E-05 |
| 329 | CE 16:1 | 6.66E-02 | DG 18:0 18:0 | 1.73E-01 |
| 330 | LPAF 18:0 | 3.66E-05 | APC 36:4 | 4.05E-05 |
| 331 | modPC 506.3/3.50 | 1.09E-06 | Cer 24:1 | 3.58E-02 |
| 332 | PS 36:2 | 4.37E-04 | APC 34:0 | 1.20E-03 |
| 333 | LPAF 18:1 | 2.60E-03 | MHC 18:0 | 2.44E-02 |
| 334 | modPC 564.4/4.70 | 8.81E-09 | DG 18:0 18:2 | 1.06E-01 |
| 335 | modPC 622.4/4.54 | 6.84E-02 | MHC 22:0 | 3.29E-10 |
| 336 | PE 34:1 | 1.98E-01 | modPC 508.3/3.30 | 8.28E-05 |
| 337 | APC 36:4 | 4.05E-05 | modPC 510.3/4.00 | 3.18E-06 |
| 338 | | | PE 36:3 | 1.09E-02 |
| 339 | | | CE 24:5 | 2.50E-02 |
| 340 | | | modPC 564.4/4.70 | 8.81E-09 |
| 341 | | | modPC 592.4/5.10 | 5.49E-06 |
| 342 | | | DG 18:0 20:4 | 5.68E-01 |
| 343 | | | modPC 650.4/3.24 | 3.58E-02 |
| 344 | | | LPC 20:2 | 4.26E-03 |
| 345 | | | LPC 18:0 | 8.07E-07 |
| 346 | | | LPC 20:5 | 1.26E-02 |
| 347 | | | LPAF 16:0 | 1.37E-05 |
| 348 | | | LPAF 18:1 | 2.60E-03 |
| 349 | | | LPC 20:1 | 2.39E-05 |
| 350 | | | PC 36:3 | 1.35E-01 |

TABLE 15

Final conditions for precursor ion scan and MRM acquisition methods for lipid identification and quantification

| Lipid class | No. of species | Internal standard | (pmol/15 μL) | Parent ion | MRM type | DP | EP | CE | CXP |
|---|---|---|---|---|---|---|---|---|---|
| ceramide (Cer) | 7 | Cer17:0 | 100 | $[M+H]^+$ | $PIS^a$, 264.3 m/z | 50 | 10 | 35 | 12 |
| monohexosylceramide (MHC) | 7 | MHC 16:0 $d_3$ | 50 | $[M+H]^+$ | PIS, 264.3 m/z | 77 | 10 | 50 | 12 |
| dihexosylceramide (DHC) | 7 | DHC 16:0 $d_3$ | 50 | $[M+H]^+$ | PIS, 264.3 m/z | 100 | 10 | 65 | 12 |
| trihexosylcermide (THC) | 7 | THC 17:0 | 50 | $[M+H]^+$ | PIS, 264.3 m/z | 130 | 10 | 73 | 12 |
| $G_{M3}$ ganglioside (GM3) | 6 | THC 17:0 | 50 | $[M+H]^+$ | PIS, 264.3 m/z | 155 | 10 | 105 | 16 |
| modified ceramide (modCer) | 13 | acCer 17:0 18:1 | 100 | $[M+H]^+$ | PIS, 264.3 m/z | 70 | 10 | 50 | 16 |
| sphingomyelin (SM) | 12 | SM 12:0 | 200 | $[M+H]^+$ | PIS, 184.1 m/z | 65 | 10 | 35 | 12 |
| phosphatidylglycerol (PG) | 4 | PG 17:0 17:0 | 100 | $[M^+ NH_4]^+$ | $NL^b$, 189 Da | 60 | 10 | 25 | 12 |
| bis(monoacylglycerol)phosphate (BMP) | 1 | BMP 14:0/14:0 | 100 | $[M^+ NH_4]^+$ | PIS, 339.3 m/z | 65 | 10 | 35 | 12 |
| phosphatidylserine (PS) | 7 | PS 17:0 17:0 | 100 | $[M+H]^+$ | NL, 185 Da | 86 | 10 | 29 | 12 |
| phosphatidylethanolamine (PE) | 18 | PE 17:0 17:0 | 100 | $[M+H]^+$ | NL, 141 Da | 80 | 10 | 31 | 12 |
| phosphatidylinositol (PI) | 17 | PE 17:0 17:0 | 100 | $[M^+ NH_4]^+$ | PIS, 184.1 m/z | 51 | 10 | 43 | 14 |
| lysophosphatidylcholine (LPC) | 16 | LPC 13:0 | 100 | $[M+H]^+$ | PIS, 184.1 m/z | 90 | 10 | 38 | 12 |
| lysoplatelet activating factor (LPAF) | 7 | LPC 13:0 | 100 | $[M+H]^+$ | PIS, 285.2 m/z | 90 | 10 | 42 | 5 |
| phosphatidylcholine (PC) | 22 | PC 13:0 13:0 | 100 | $[M+H]^+$ | PIS, 184.1 m/z | 100 | 10 | 45 | 11 |
| odd chain phosphatidylcholine (oddPC) | 16 | PC 13:0 13:0 | 100 | $[M+H]^+$ | PIS, 184.1 m/z | 100 | 10 | 45 | 11 |
| alkylphosphatidylcholine (APC) | 18 | PC 13:0 13:0 | 100 | $[M+H]^+$ | PIS, 184.1 m/z | 100 | 10 | 45 | 11 |
| modified phosphatidylcholine (modPC) | 38 | PC 13:0 13:0 | 100 | $[M+H]^+$ | PIS, 184.1 m/z | 100 | 10 | 45 | 11 |
| free cholesterol (COH) | 1 | COH $d_7$ | 1000 | $[M^+ NH_4]^+$ | PIS, 369.3 m/z | 55 | 10 | 17 | 12 |
| cholesterol ester (CE) | 30 | CE 18:0 $d_6$ | 1000 | $[M^+ NH_4]^+$ | PIS, 369.3 m/z | 30 | 10 | 20 | 12 |
| modified cholesterol ester (modCE) | 4 | CE 18:0 $d_6$ | 1000 | $[M^+ NH_4]^+$ | PIS, 369.3 m/z | 55 | 10 | 20 | 12 |

TABLE 15-continued

Final conditions for precursor ion scan and MRM acquisition methods for lipid identification and quantification

| Lipid class | No. of species | Internal standard | (pmol/15 μL) | Parent ion | MRM type | DP | EP | CE | CXP |
|---|---|---|---|---|---|---|---|---|---|
| diacylglycerol (DG) | 27 | DAG 15:0 15:0 | 200 | $[M^+ NH_4]^+$ | NL, fatty acid | 55 | 10 | 30 | 22 |
| triaclyglycerol (TG) | 44 | TAG 17:0 17:0 17:0 | 100 | $[M^+ NH_4]^+$ | NL, fatty acid | 95 | 10 | 30 | 12 |

[a]NL, neutral loss scan;
[b]PIS, precursor ion scan;
[c]PC 13:0 13:0 was used as internal standard for species with m/z <700;
[d]DP, declustering potential;
[b]EP, entrance potential;
[c]CE, collision energy;
[d]CXP, exit potential.

TABLE 16

Final summary[a] of univariate analysis of plasma lipids in control, stable CAD and unstable CAD groups

| | | # of species | | % difference[b] | |
|---|---|---|---|---|---|
| Lipid class | total | control vs CAD p < 0.01[a] | stable vs unstable p < 0.01[a] | control vs CAD | stable vs unstable |
| ceramide (CER) | 7 | 2 | | −6.3 | 0.6 |
| monohexosylceramide (MHC) | 7 | 4 | | −24.9 | −4.6 |
| dihexosylceramide (DHC) | 7 | 2 | 1 | −12.8 | 8.1 |
| trihexosylcermide (THC) | 7 | 2 | | −13.6 | 2.0 |
| $G_{M3}$ Ganglioside (GM3) | 6 | 1 | | −9.3 | −3.2 |
| modified ceramides (modCer) | 13 | 5 | 1 | −9.4 | 2.1 |
| sphingomyelin (SM) | 12 | 4 | 1 | −9.3 | 2.9 |
| phosphatidylglycerol (PG) | 4 | | | −7.0 | −11.7 |
| bis(monoacylglycero)phosphate (BMP) | 1 | | | 2.6 | 6.4 |
| phosphatidylserine (PS) | 7 | 6 | | −27.4 | 23.9 |
| phosphatidylethanolamine (PE) | 18 | | | −2.3 | 5.5 |
| phosphatidylinositol (PI) | 17 | 7 | 9 | −20.4 | −13.8 |
| lysophosphatidylcholine (LPC) | 16 | 10 | 8 | −14.5 | −10.7 |
| lysoplatelet activating factor (LPAF) | 7 | 2 | | −12.1 | 1.5 |
| phosphatidylcholine (PC) | 22 | 9 | 3 | −7.2 | −3.5 |
| odd-chain phosphatidylcholine (oddPC) | 16 | 7 | | −8.5 | −2.5 |
| alkylphosphatidylcholine (APC) | 17 | 9 | 2 | −16.0 | −4.9 |
| modified phosphatidylcholine (modPC) | 39 | 15 | | −12.4 | 2.7 |
| free cholesterol (COH) | 1 | | | −16.7 | −3.9 |
| cholesterol esters (CE) | 30 | 4 | 1 | −0.6 | −2.0 |
| modified cholesterol esters (modCE) | 4 | | | 6.6 | 0.4 |
| diacylglycerol (DG) | 27 | 5 | 2 | 29.1 | −2.8 |
| triaclyglycerol (TG) | 44 | 1 | 2 | 2.1 | −7.3 |
| Total lipid species | 329 | 95 | 30 | | |

[a]table shows the number of lipids in each class with p < 0.01
[b]% difference between mean values for each lipid class, bold signifies p < 0.01 (Mann Whitney U test)

TABLE 17

| Model | features[1] | C-statistic[2] | % accuracy[2] |
|---|---|---|---|
| A. Logistic Regression Models of Stable CAD vs Unstable CAD | | | |
| Lipids | 4.4 | 72.9 (72.1-73.6) | 67.0 (66.3-67.6) |
| Risk Factors | 1.4 | 65.4 (65.0-65.8) | 68.5 (68.1-68.8) |
| Lipids and Risk Factors | 4.8 | 78.8 (78.1-79.4) | 71.0 (70.3-71.6) |
| B. Logistic Regression Models of Control vs CAD | | | |
| Lipids | 5.7 | 94.6 (94.4-94.8) | 87.3 (87.1-87.6) |
| Risk Factors | 4.2 | 95.6 (95.4-95.8) | 90.4 (90.1-90.7) |
| Lipids and Risk Factors | 5.5 | 98.2 (98.1-98.3) | 92.4 (92.1-92.6) |

[1]mean number of features in the model.
[2]mean value and 95% confidence intervals.

TABLE 18

Ranked Lipids in the Stable CAD vs Unstable CAD Logistic Model[1]

| features | % occurrence[2] | odds ratio[3] | 95% CI |
|---|---|---|---|
| modCer 731.6 | 61.0 | 1.77 | 1.75-1.79 |
| GM3 18:0 | 59.7 | 0.64 | 0.63-0.65 |
| PC34:5 | 59.3 | 0.61 | 0.60-0.61 |
| DHC 18:1 | 36.7 | 1.52 | 1.51-1.54 |
| APC 34:2 | 28.7 | 0.66 | 0.65-0.66 |
| SM 18:0 | 18.0 | 1.70 | 1.65-1.74 |
| Cer 18:1 | 15.7 | 1.47 | 1.45-1.49 |
| PI 36:1 | 14.0 | 0.63 | 0.61-0.64 |
| APC 36:0 | 13.7 | 1.42 | 1.40-1.43 |
| DG 18:1 20:0 | 13.3 | 0.65 | 0.63-0.66 |
| LPC 14:0 | 11.0 | 0.65 | 0.63-0.66 |
| LPC 16:1 | 10.0 | 0.62 | 0.60-0.63 |
| PC 24:0 | 7.3 | 1.46 | 1.41-1.50 |
| Cer 18:0 | 5.7 | 1.47 | 1.42-1.53 |

TABLE 18-continued

Ranked Lipids in the Stable CAD vs Unstable CAD Logistic Model[1]

| features | % occurrence[2] | odds ratio[3] | 95% CI |
|---|---|---|---|
| PI 36:3 | 5.3 | 0.64 | 0.61-0.66 |
| PI 38:2 | 4.7 | 0.64 | 0.61-0.67 |

[1]lipids only.
[2]indicates the frequency of occurrence within the model.
[3]indicates the risk associated with a change of 1 standard deviation.

TABLE 19

Ranked Risk Factors in the Stable CAD vs Unstable CAD Logistic Models[1]

| features | % occurrence[2] | odds ratio[3] | 95% CI |
|---|---|---|---|
| hsCRP | 100.0 | 1.71 | 1.69-1.72 |
| diabetes | 16.3 | 0.70 | 0.69-0.71 |
| smoker | 13.0 | 1.43 | 1.41-1.45 |
| HDL | 6.3 | 0.68 | 0.66-0.70 |
| SBP | 4.7 | 0.72 | 0.72-0.73 |
| BMI | 1.0 | 0.66 | 0.54-0.84 |
| cholesterol | 0.7 | 0.72 | 0.70-0.74 |
| age | 0.3 | 0.71 | |
| Hist of CAD | 0.3 | 0.72 | |
| sex | 0.3 | 1.36 | |
| TRIGs | 0.3 | 1.48 | |

[1]risk factors only.
[2]indicates the frequency of occurrence within the model.
[3]indicates the risk associated with a change of 1 standard deviation.

TABLE 20

Ranked Features in the Stable CAD vs Unstable CAD Logistic Model[1]

| features | % occurrence[2] | odds ratio[3] | 95% CI |
|---|---|---|---|
| hsCRP | 99.0 | 1.79 | 1.77-1.81 |
| PC 34:5 | 72.0 | 0.59 | 0.59-0.60 |
| DHC 18:1 | 49.7 | 1.53 | 1.52-1.55 |
| Cer 18:1 | 42.7 | 1.51 | 1.49-1.52 |
| modCer 731.6 | 37.7 | 1.70 | 1.67-1.72 |
| GM3 18:0 | 31.7 | 0.63 | 0.62-0.64 |
| LPC 16:1 | 20.7 | 0.60 | 0.59-0.62 |
| DG 18:1/20:0 | 17.0 | 0.64 | 0.63-0.65 |
| LPC 14:0 | 11.0 | 0.62 | 0.60-0.64 |
| LPC 18:1 | 10.3 | 0.65 | 0.63-0.66 |
| smoker | 10.3 | 1.46 | 1.44-1.48 |
| modPC.622.4/4.0 | 6.3 | 1.47 | 1.44-1.51 |
| LPC 18:2 | 5.7 | 0.65 | 0.64-0.66 |
| APC 34:2 | 5.7 | 0.67 | 0.66-0.68 |
| LPC 24:0 | 4.7 | 0.66 | 0.64-0.67 |
| PI 36:1 | 4.0 | 0.63 | 0.61-0.66 |

[1]lipids and risk factors combined.
[2]indicates the frequency of occurrence within the model.
[3]indicates the risk associated with a change of 1 standard deviation.

TABLE 21

Ranked Lipids in the Control vs CAD Logistic Model[1]

| features | % occurrence[2] | odds ratio[3] | 95% CI |
|---|---|---|---|
| LPC 22:0 | 100.0 | 0.40 | 0.40-0.40 |
| PS 40:6 | 96.7 | 0.56 | 0.56-0.56 |
| PI 34:0 | 42.0 | 0.61 | 0.60-0.61 |
| Cer 20:0 | 39.3 | 1.61 | 1.59-1.63 |
| Cer 18:0 | 39.0 | 1.72 | 1.70-1.74 |
| APC 34:2 | 28.0 | 0.58 | 0.57-0.59 |
| PC 34:5 | 22.7 | 0.59 | 0.58-0.60 |
| LPC 20:3 | 16.7 | 1.50 | 1.48-1.51 |
| PC 28:0 | 15.3 | 0.63 | 0.61-0.64 |
| modPC 692.4/5.8 | 15.3 | 0.62 | 0.60-0.63 |
| APC 30:0 | 14.7 | 0.63 | 0.61-0.64 |
| modPC 736.5/5.7 | 14.3 | 0.61 | 0.59-0.62 |
| LPC 20:4 | 14.0 | 1.51 | 1.49-1.53 |
| APC 38:6 | 13.3 | 0.62 | 0.60-0.63 |
| modPC 720.5.4.5 | 11.3 | 0.69 | 0.68-0.70 |
| PI 36:0 | 11.0 | 0.64 | 0.63-0.66 |

[1]lipids only.
[2]indicates the frequency of occurrence within the model.
[3]indicates the risk associated with a change of 1 standard deviation.

TABLE 22

Ranked Risk Factors in the Control vs CAD Logistic Model[1]

| features | % occurrence[2] | odds ratio[3] | 95% CI |
|---|---|---|---|
| hsCRP | 100.0 | 3.02 | 3.01-3.04 |
| age | 99.0 | 1.82 | 1.81-1.84 |
| TRIGs | 91.0 | 1.71 | 1.70-1.72 |
| SBP | 82.0 | 0.65 | 0.65-0.66 |
| HDL | 22.0 | 1.58 | 1.56-1.60 |
| sex | 17.0 | 0.70 | 0.69-0.70 |
| Hist of CAD | 8.7 | 1.44 | 1.42-1.45 |
| BMI | 1.0 | 0.67 | 0.65-0.68 |
| cholesterol | 0.0 | | |

[1]risk factors only.
[2]indicates the frequency of occurrence within the model.
[3]indicates the risk associated with a change of 1 standard deviation.

TABLE 23

Ranked Features in the Control vs CAD Logistic Model[1]

| features | % occurrence[2] | odds ratio[3] | 95% CI |
|---|---|---|---|
| hsCRP | 100.0 | 2.35 | 2.33-2.36 |
| LPC 22.0 | 99.7 | 0.47 | 0.47-0.47 |
| age | 97.0 | 1.76 | 1.74-1.77 |
| PS 40:6 | 94.7 | 0.60 | 0.59-0.60 |
| PC 34:5 | 37.7 | 0.63 | 0.62-0.63 |
| SBP | 18.7 | 0.65 | 0.65-0.66 |
| modPC 879.6/6.1 | 13.0 | 0.63 | 0.62-0.64 |
| APC 30:0 | 10.7 | 0.63 | 0.62-0.64 |
| APC 38:6 | 10.7 | 0.62 | 0.61-0.64 |
| Cer 18:0 | 10.3 | 1.61 | 1.59-1.63 |
| modPC 877.6/6.0 | 8.7 | 0.66 | 0.65-0.68 |
| modPC 736.5/5.7 | 8.3 | 0.61 | 0.60-0.62 |
| HDL | 7.3 | 1.57 | 1.54-1.60 |
| LPC 20:3 | 7.3 | 1.52 | 1.49-1.54 |
| PC 28:0 | 7.0 | 0.63 | 0.62-0.64 |
| Cer 20:0 | 4.0 | 1.52 | 1.47-1.58 |

[1]lipids and risk factors combined.
[2]indicates the frequency of occurrence within the model.
[3]indicates the risk associated with a change of 1 standard deviation.

TABLE 24

Ranked Features in the Stable CAD vs Unstable CAD Recursive Feature Elimination Models[1]

| | | % occurrence[3] # features in model | | | | |
|---|---|---|---|---|---|---|
| Feature | % change[2] | 1 | 2 | 4 | 8 | 16 |
| hsCRP | 243 | 38 | 82 | 97 | 100 | 100 |
| PC 34:5 | −11 | 40 | 61 | 76 | 87 | 95 |
| modCer 731.6 | 20 | 3 | 13 | 53 | 83 | 96 |

TABLE 24-continued

Ranked Features in the Stable CAD vs Unstable CAD Recursive Feature Elimination Models[1]

| Feature | % change[2] | % occurrence[3] # features in model | | | | |
|---|---|---|---|---|---|---|
| | | 1 | 2 | 4 | 8 | 16 |
| DHC 18:1 | 24 | 1 | 4 | 26 | 67 | 86 |
| GM3 18:0 | −11 | 0 | 2 | 19 | 62 | 88 |
| LPC 16:1 | −23 | 6 | 11 | 31 | 49 | 60 |
| Cer 18:1 | 4 | 0 | 3 | 18 | 47 | 67 |
| APC 34:2 | −19 | 0 | 0 | 4 | 41 | 72 |
| DG 18:1 20:0 | −40 | 3 | 7 | 23 | 37 | 53 |
| SM 18:0 | 16 | 1 | 2 | 9 | 26 | 56 |
| smoker | 101 | 0 | 0 | 3 | 16 | 49 |
| APC 36:0 | 13 | 0 | 0 | 0 | 6 | 35 |
| PC 24:0 | 16 | 0 | 0 | 0 | 3 | 29 |
| PI 36:1 | −24 | 1 | 1 | 3 | 11 | 24 |
| PC 34:3 | −20 | 1 | 1 | 1 | 6 | 23 |
| LPC 14:0 | −26 | 4 | 5 | 6 | 10 | 19 |

[1]lipids and risk factors combined.
[2]% difference of mean unstable CAD value relative to mean stable CAD value.
[3]indicates the frequency of occurrence within the models of each size as indicated.

TABLE 25

Ranked Features in the Control vs CAD Recursive Feature Elimination Models[1]

| Feature | % difference[2] | % occurrence[3] # features in model | | | | |
|---|---|---|---|---|---|---|
| | | 1 | 2 | 4 | 8 | 16 |
| LPC 22:0 | −48 | 55 | 100 | 100 | 100 | 100 |
| hsCRP | 260 | 45 | 99 | 100 | 100 | 100 |
| PS 40:6 | −54 | 0 | 1 | 80 | 99 | 100 |
| age | 19 | 0 | 0 | 28 | 91 | 100 |
| LPC 24:0 | −37 | 0 | 0 | 34 | 73 | 91 |
| PS 40:5 | −49 | 0 | 0 | 2 | 62 | 96 |
| LPC 20:0 | −42 | 0 | 0 | 5 | 18 | 66 |
| PI 34:0 | −43 | 0 | 0 | 3 | 14 | 53 |
| Cer 20:0 | 17 | 0 | 0 | 0 | 17 | 42 |
| HDL | −18 | 0 | 0 | 0 | 15 | 40 |
| Systolic BP | 11 | 0 | 0 | 0 | 9 | 38 |
| modPC 877.6/6.0 | 8 | 0 | 0 | 4 | 18 | 33 |
| PC 34:5 | 19 | 0 | 0 | 9 | 21 | 30 |
| LPC 20:3 | 19 | 0 | 0 | 0 | 8 | 34 |
| APC 38:6 | −23 | 0 | 0 | 3 | 14 | 28 |
| CE 22:4 | −15 | 0 | 0 | 0 | 4 | 30 |

[1]lipids and risk factors combined.
[2]% difference of mean CAD value relative to mean control value.
[3]indicates the frequency of occurrence within the models of each size as indicated.

TABLE 26

Lipid Species Affected by Statin Use

| Lipid species | % difference with statin use | p value[1] | % difference Control vs CAD[2] | % difference stable CAD vs unstable CAD[2] |
|---|---|---|---|---|
| Cer 18:1 | −4.6 | 4.13E-02 | 2.9 | 4.2 |
| DHC 18:1 | −14.7 | 3.59E-02 | −11.3 | 24.1 |
| GM3 16:0 | −14.2 | 3.15E-03 | −7.2 | 1.1 |
| PC 36:5 | 18.1 | 4.42E-02 | −19.2 | −10.1 |
| PC 36:4 | 20.7 | 1.33E-02 | 6.6 | 0.5 |
| PC 38:6 | 9.6 | 1.90E-02 | −11.2 | 2.6 |
| PC 38:5 | 15.1 | 9.18E-03 | −8.9 | −2.0 |
| PC 38:4 | 21.4 | 1.04E-02 | 4.3 | −0.9 |
| PC 40:6 | 15.4 | 2.89E-02 | −6.1 | 5.4 |
| PC 40:5 | 16.8 | 9.99E-03 | −5.3 | −1.8 |
| PC 37:5 | 23.0 | 4.27E-02 | −16.6 | −11.9 |
| APC 32:0 | −11.7 | 3.22E-02 | −7.2 | 1.0 |
| APC 34:1 | −14.5 | 3.71E-02 | −10.0 | −2.5 |
| APC 36:2 | −18.6 | 3.59E-02 | −27.1 | −8.1 |
| LPC 20:5 | 35.0 | 3.22E-02 | −14.7 | −18.1 |
| PI 36:2 | −27.1 | 1.86E-03 | −27.9 | −10.5 |
| PI 38:4 | 17.3 | 4.42E-02 | −13.0 | −9.8 |
| PS 38:4 | 51.5 | 4.27E-02 | −30.6 | 23.7 |
| DG 16:0 20:0 | 46.0 | 4.74E-02 | −45.2 | −36.0 |
| DG 18:1 20:3 | 76.2 | 8.08E-03 | 64.8 | −25.7 |
| DG 18:1 20:0 | 54.1 | 3.99E-02 | −41.6 | −39.9 |
| C22:3 | −18.8 | 2.94E-02 | −1.6 | 0.3 |
| C22:2 | −39.1 | 4.99E-03 | −27.5 | 4.2 |
| C22:1 | −22.4 | 1.63E-02 | −20.0 | −0.6 |
| C24:5 | −34.7 | 4.61E-04 | −7.3 | 20.0 |
| C24:4 | −27.5 | 5.96E-03 | −3.4 | 2.3 |
| C24:2 | −29.6 | 6.51E-03 | −14.7 | −3.0 |
| C24:1 | −19.9 | 3.34E-02 | −14.5 | 1.5 |

[1]p value calculated from Mann Whitney U test.
[2]bold numbers indicate significant differences (p < 0.01, from logistic regression adjusted for age and sex).

TABLE 27

Medication of stable and unstable CAD cohorts

| Medication | Stable % | Unstable % | Chi Square | p |
|---|---|---|---|---|
| clopidogrel[1] | 18 | 27 | 1.625 | 0.202 |
| aspirin[1] | 95 | 94 | 0.103 | 0.748 |
| statin[2] | 54 | 88 | 19.991 | 0.000 |
| beta blocker[3] | 59 | 65 | 0.612 | 0.434 |
| ACE inhibitor[3] | 43 | 56 | 2.328 | 0.127 |
| angiotensin-II blocker[3] | 23 | 6 | 1.076 | 0.300 |
| oral/sublingual nitrate[3] | 31 | 27 | 0.269 | 0.604 |
| Ca channel blocker[3] | 26 | 19 | 1.212 | 0.271 |
| heparin infusion[4] | 0 | 21 | 14.544 | 0.000 |
| low molecular weight heparin[4] | 0 | 11 | 7.236 | 0.007 |
| tirofiban[1] | 0 | 6 | 3.903 | 0.048 |
| frusemide[3] | 11 | 9 | 0.314 | 0.575 |
| sulfonylurea[5] | 15 | 14 | 0.040 | 0.842 |
| metformin[5] | 23 | 11 | 3.593 | 0.058 |

[1]antiplatelet,
[2]lipid lowering,
[3]antihypertensive,
[4]anticoagulant,
[5]anti-diabetic.

BIBLIOGRAPHY (AIHW) AIoHaW. Health system expenditure, on disease and injury in Australia, 2000-01. Health and Welfare Expenditure Series No. 19, 2004; HWE 26

Braunwald, Circulation 80:410-4, 1989

Bylesjö et al. *Journal of Chemometrics* 20:341-51, 2006

Cui and Thomas, *Journal of Chromatography B;* 877:2709-15, 2009

Damas and Aukrust *Scand Cardiovasc J* 40:262-6, 2006

Davis et al., *J. Biol. Chem.* 283: 6428-6437, 2008

Fahy et al., *J Lipid Res.* 50: S9-14, 2009

Fahy et al., *J Lipid Res.* 51(6): 1618, 2010

Fawcett T *Pattern Recogn Lett* 27:861-74, 2006

Folch et al. *J Biol Chem* 226:497-509, 1957

Heart Disease and Stroke Statistics-2006 Update, Dallas Tex.: American Heart Association, 2006 Available at http://www.americanheartorg/downloadable/heart/1198257493273HS_Stats%202008.pdf Murphy et al. *Chem Rev* 101:479-526, 2001
Naghavi et al. *Circulation* 108:1772-8, 2003
National Health Survey: Summary of Results, Australia, 2004-05, cat. no. 4364.0, ABS, Canberra, Vol: Australian Bureau of Statistics, 2006
Oei et al., *Circulation.* 111: 570-575, 2005
Ridker et al. Circulation 109:IV-6-19, 2004
Ridker et al. *JAMA: Journal of the American Medical Association* 297:611-9, 2007
Shearer et al. *PLoS ONE* 4:e5444, 2009
Stenlund et al. *Analytical Chemistry* 80:6898-906, 2008
White et al. *Cardiovascular Research* 75:813-20, 2007

What is claimed is:

1. A method of treatment or prophylaxis of a subject suspected of being vulnerable or non-vulnerable to plaque rupture, the method comprising:
   a) obtaining a lipid sample from the subject;
   b) determining the levels of a lipid analyte in the lipid sample selected from the list consisting of modCer 731.6 and DHC 18:1; wherein the level of the individual lipid analytes is different between vulnerable subjects and non-vulnerable subjects and wherein the level of the lipid analytes in the subject relative to a control identifies the subject as being vulnerable or non-vulnerable to plaque rupture; and
   c) providing therapeutic and/or behavioral modification to the subject based on whether the subject is determined to be vulnerable or non-vulnerable to plaque rupture.

2. The method of claim 1, further comprising comparing the level of the at least two lipid analytes in the sample to the respective levels of the same lipid analytes in at least one control sample selected from a first control sample from a subject that is vulnerable to plaque rupture and a second control sample from a subject that is non-vulnerable to plaque rupture, wherein a similarity in the respective levels of the at least two lipid analytes between the sample and the second control sample identifies the subject as being non-vulnerable to plaque rupture, and wherein a similarity in the respective levels of the at least two lipid analytes between the sample and the first control sample identifies the subject as being vulnerable to plaque rupture.

3. The method of claim 2, further comprising comparing the level of the at least two lipid analytes in the sample to the respective levels of the same lipid analytes in at least one sample from a healthy subject, wherein a similarity in the respective levels of the at least two lipid analytes between the sample and the sample(s) from the healthy subject identifies the subject as being healthy with respect to vulnerability to plaque rupture.

4. The method of claim 1, further comprising determining or determining and comparing the levels of 2, 3, 4, 5, 6, 7, 8, 9, 10, 11, 12, 13, 14, 15 or 16 lipid analytes listed in Table 1 wherein the level of an individual lipid analyte listed in Table 1 is different between subjects that are vulnerable to plaque rupture and subjects that are non-vulnerable to plaque rupture.

5. The method of claim 1, further comprising determining the levels of at least two further lipid analytes selected from the group consisting of GM3 18:0, PC34:5, APC 34:2, SM 18:0, Cer 18:1, PI 36:1, APC 36:0, DG 18:1 20:0, LPC 14:0, LPC 16:1, PC 24:0, Cer 18:0, PI 36:3, PI 38:2, modPC.622.4/40, LPC 18:2, LPC 24:0, PC 34:3, modPC 752.6/5.58, PI 34:0, modCer 703.6/5.87 and SM 22:1.

6. The method of claim 5, comprising determining the levels of at least four, six, eight or sixteen lipid analytes selected from the group consisting of, GM3 18:0, PC34:5, APC 34:2, SM 18:0, Cer 18:1, PI 36:1, APC 36:0, DG 18:1 20:0, LPC 14:0, LPC 16:1, PC 24:0, Cer 18:0, PI 36:3, PI 38:2, modPC.622.4/40, LPC 18:2 and LPC 24:0, PC 34:3, modPC 752.6/5.58, PI 34:0, modCer 703.6/5.87 and SM 22:1.

7. The method of claim 1, wherein the levels of lipid analytes are used in combination with one or more traditional risk factors selected from age, sex, smoker, diabetes, hypertension, coronary heart disease (CAD) family history, body mass index (BMI), total cholesterol, low-density lipoprotein (LDL), high-density lipoprotein (HDL), triglycerides, glucose and high-sensitivity C-reactive protein (hsCRP) to thereby identify the subject as being vulnerable or non-vulnerable to plaque rupture.

* * * * *